United States Patent
Okamura et al.

(10) Patent No.: US 9,174,036 B2
(45) Date of Patent: Nov. 3, 2015

(54) INTRODUCER ASSEMBLY

(75) Inventors: Ryo Okamura, Shizuoka (JP); Takayuki Mouri, Shizuoka (JP); Junko Kuniyasu, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 316 days.

(21) Appl. No.: 13/613,872

(22) Filed: Sep. 13, 2012

(65) Prior Publication Data

US 2013/0046241 A1     Feb. 21, 2013

Related U.S. Application Data

(63) Continuation of application No. PCT/JP2011/055927, filed on Mar. 14, 2011.

(30) Foreign Application Priority Data

| Mar. 15, 2010 | (JP) | ................................. 2010-057808 |
| Jun. 29, 2010 | (JP) | ................................. 2010-148158 |
| Dec. 28, 2010 | (JP) | ................................. 2010-291674 |
| Dec. 28, 2010 | (JP) | ................................. 2010-291703 |

(51) Int. Cl.
  *A61M 39/06*     (2006.01)
  *A61M 25/06*     (2006.01)
  (Continued)

(52) U.S. Cl.
  CPC ....... *A61M 39/0613* (2013.01); *A61M 25/0097* (2013.01); *A61M 25/0662* (2013.01);
  (Continued)

(58) Field of Classification Search
  CPC .......... A61M 25/002; A61M 25/0097; A61M 25/0662; A61M 2025/0681; A61M 39/06; A61M 39/0606; A61M 39/0613; A61M 2039/062; A61M 2039/0626; A61M 2039/0633; A61M 2039/064; A61M 2039/0646; A61M 2039/0653
  USPC ............. 604/164.01, 164.02, 164.08, 164.09, 604/164.1, 167.01, 167.02, 167.03, 167.04, 604/167.06, 171
  See application file for complete search history.

(56) References Cited

U.S. PATENT DOCUMENTS

| 5,114,408 A | * | 5/1992 | Fleischhaker et al. ... 604/167.04 |
| 5,591,137 A | | 1/1997 | Stevens |
| 6,106,487 A | | 8/2000 | Duane et al. |

(Continued)

FOREIGN PATENT DOCUMENTS

| EP | 0 658 357 A2 | 6/1995 |
| JP | 59-166163 A | 9/1984 |

(Continued)

OTHER PUBLICATIONS

International Search Report (PCT/ISA/210) issued on Apr. 5, 2011, by the Japanese Patent Office as the International Searching Authority for International Application No. PCT/JP2011/055927.

(Continued)

Primary Examiner — Andrew Gilbert
(74) Attorney, Agent, or Firm — Buchanan Ingersoll & Rooney PC

(57) ABSTRACT

An introducer assembly is composed of an introducer sheath and a dilator which have been previously integrated with each other to permit the hemostatic valve to exhibit its hemostatic function over an extended period of time without significantly adversely affecting the inherent function of the dilator tube. The introducer assembly includes a dilator tube passing through a passage of a hemostatic valve. The introducer assembly has a deforming member arranged between the hemostatic valve and a cap. As the cap is pushed toward the proximal end surface of a sheath hub for engagement with the sheath hub, the cap presses the hemostatic valve and applies a compressive force to the hemostatic valve in such a direction as to close the passage.

9 Claims, 39 Drawing Sheets

(51) Int. Cl.
*A61M 29/00* (2006.01)
*A61M 25/00* (2006.01)

(52) U.S. Cl.
CPC ............. *A61M29/00* (2013.01); *A61M 25/002* (2013.01); *A61M 2025/0681* (2013.01); *A61M 2039/064* (2013.01); *A61M 2039/0653* (2013.01)

(56) References Cited

U.S. PATENT DOCUMENTS

| | | | |
|---|---|---|---|
| 6,179,813 B1* | 1/2001 | Ballow et al. | 604/164.01 |
| 6,416,499 B2* | 7/2002 | Paul, Jr. | 604/256 |
| 6,458,103 B1* | 10/2002 | Albert et al. | 604/167.03 |
| 6,575,960 B2 | 6/2003 | Becker et al. | |
| 7,491,176 B2* | 2/2009 | Mann | 600/564 |
| 2008/0097386 A1* | 4/2008 | Osypka | 604/510 |
| 2010/0185153 A1* | 7/2010 | Sugiki et al. | 604/167.04 |

FOREIGN PATENT DOCUMENTS

| | | | |
|---|---|---|---|
| JP | 8-168532 A | | 7/1996 |
| JP | 2003-325671 A | | 11/2003 |
| JP | 2005-087574 A | | 4/2005 |
| JP | 2009/041522 A1 | | 4/2009 |
| WO | 2009/041522 A1 | | 4/2009 |
| WO | WO 2009/041522 A1 | | 4/2009 |

OTHER PUBLICATIONS

Chinese Office Action issued Jun. 4, 2014 by the Chinese Patent Office, in corresponding Chinese Patent Application No. 201180014165 (8 pages).

Extended European Search Report dated Apr. 29, 2014, issued by the European Patent Office in the corresponding European Application No. 11756233.0. (9 pages).

Japanese Office Action issued Nov. 28, 2014, by the Japan Patent Office, in corresponding Japanese Patent Application No. 2010-291674 (3 pages).

Japanese Office Action issued Jun. 2, 2015, by the Japan Patent Office, in corresponding Japanese Patent Application No. 2010-291703 (4 pages).

* cited by examiner

FIG. 5
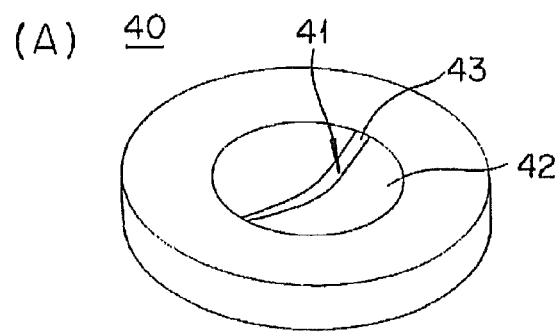
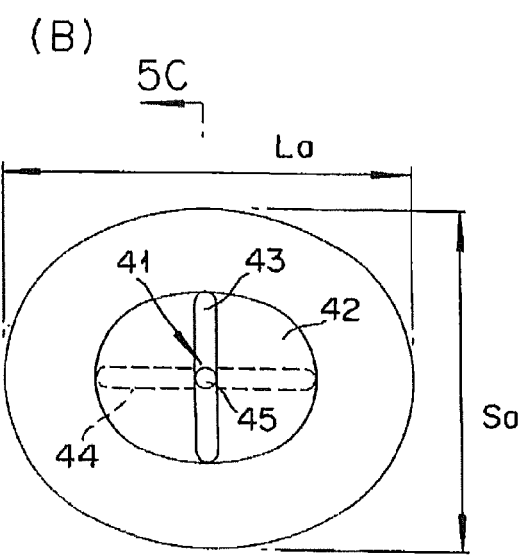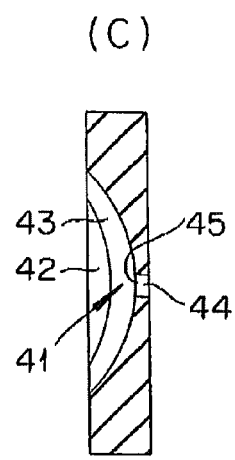

FIG. 6
(A) 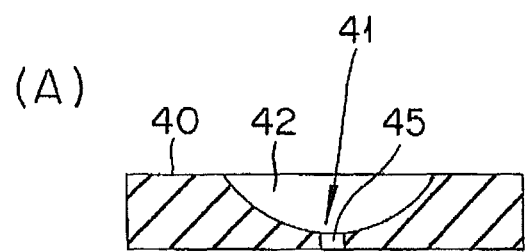
(B) 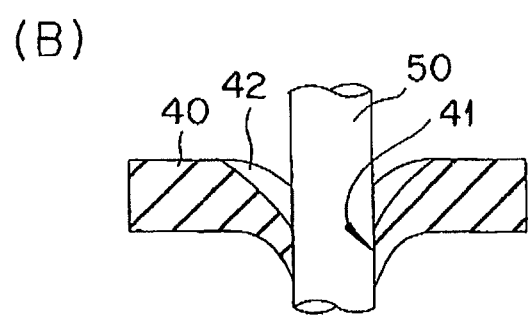
(C) 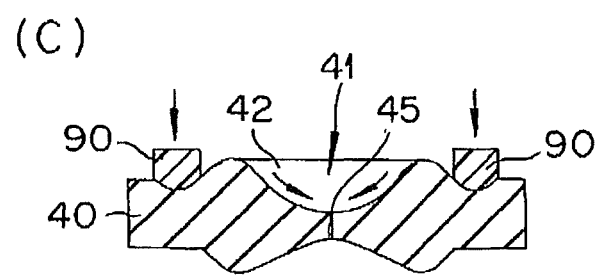

FIG. 7
(A)
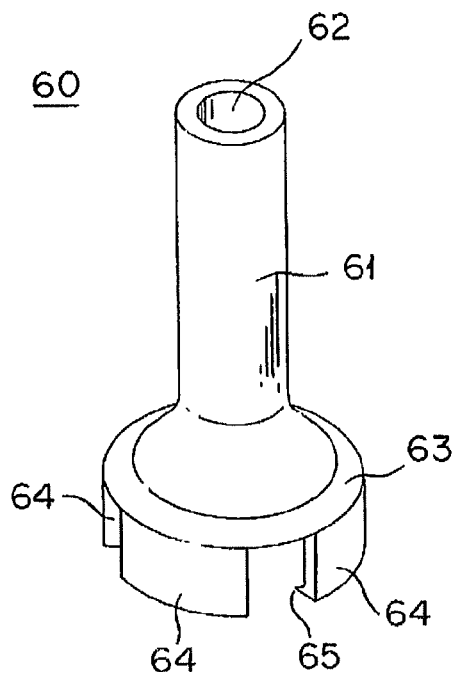
(B)
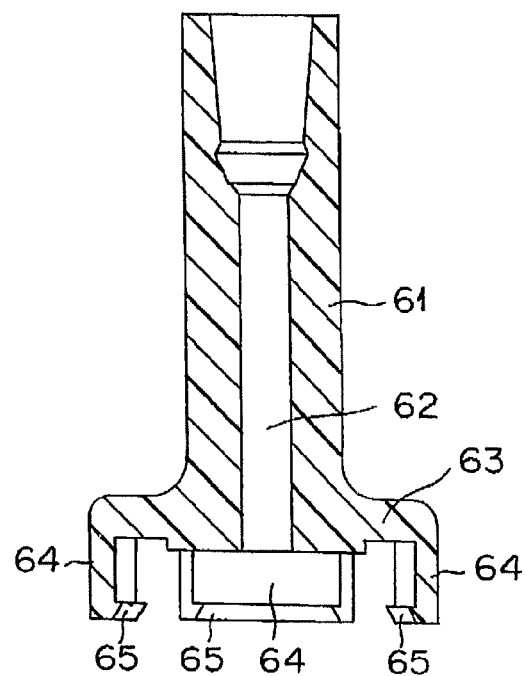

FIG. 8
(A)
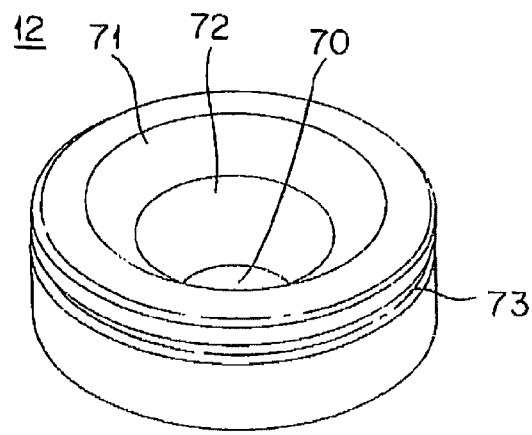
(B)
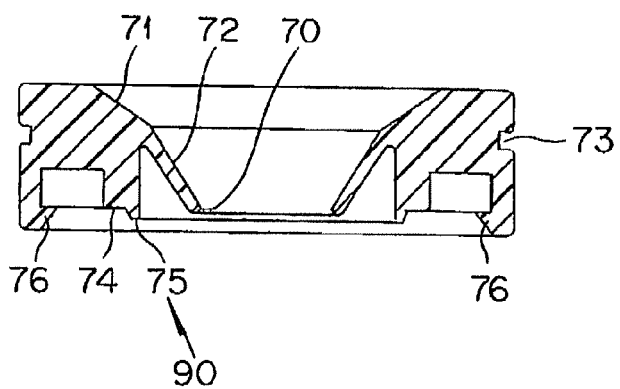

FIG. 15
(A)
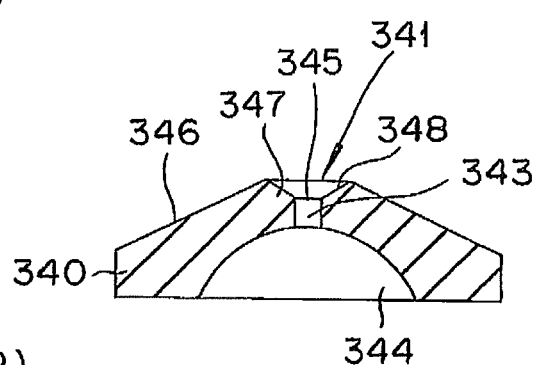
(B)
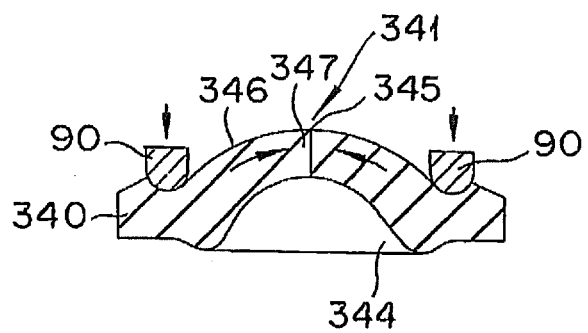

FIG. 21
(A)
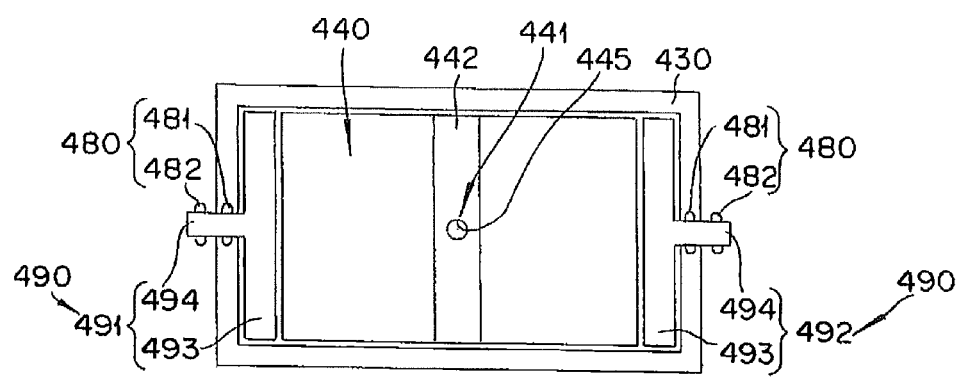
(B)
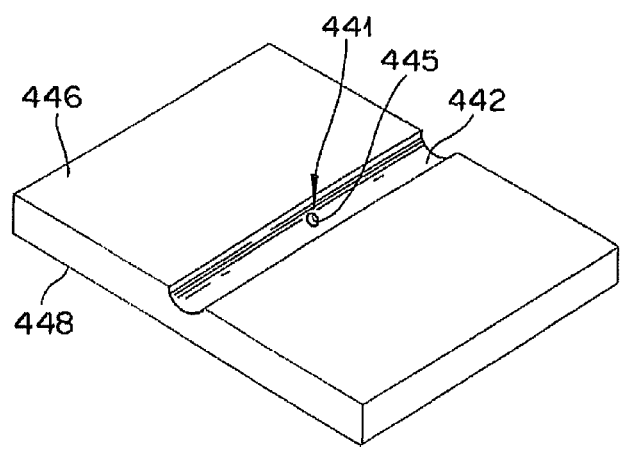

FIG. 22
(A)
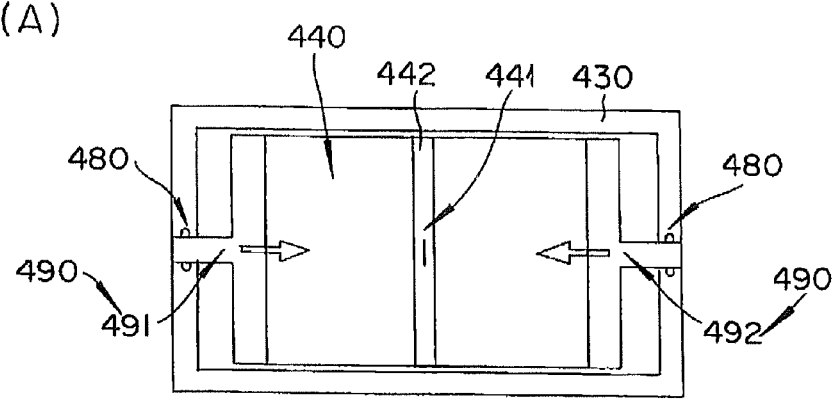
(B)
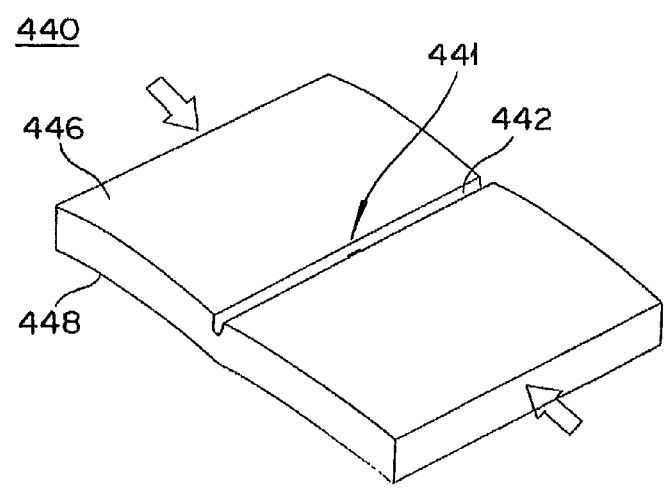

FIG. 27
(A)
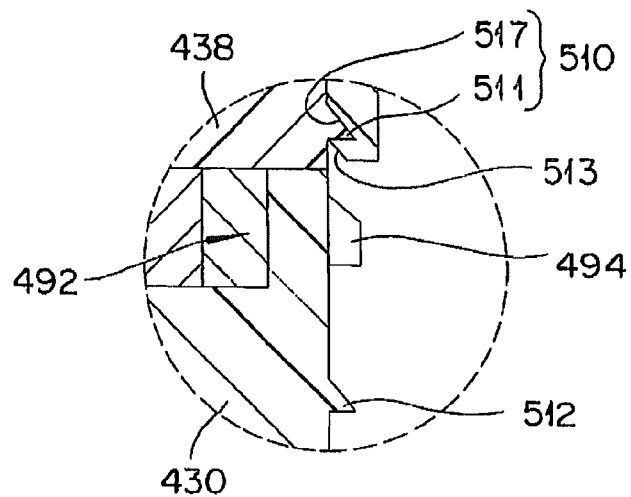
(B)
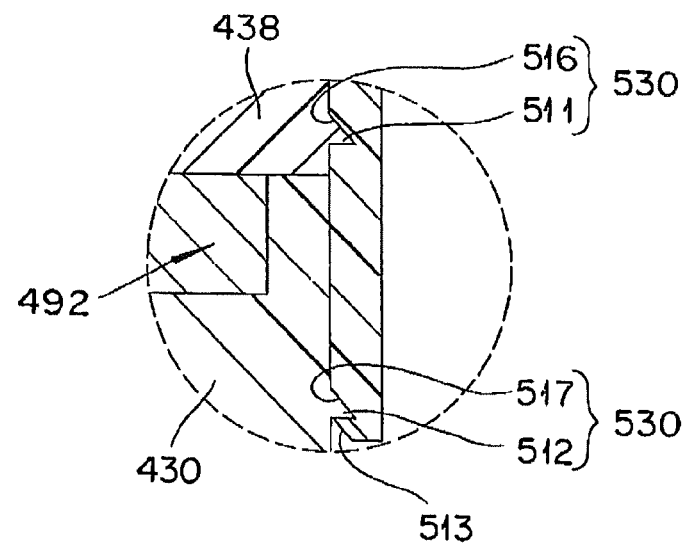

FIG. 38
(A)
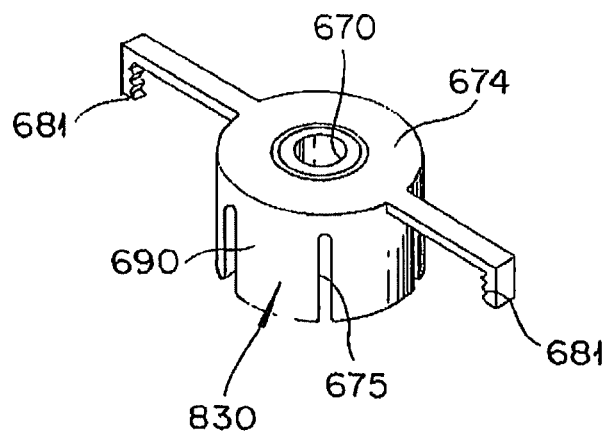
(B)
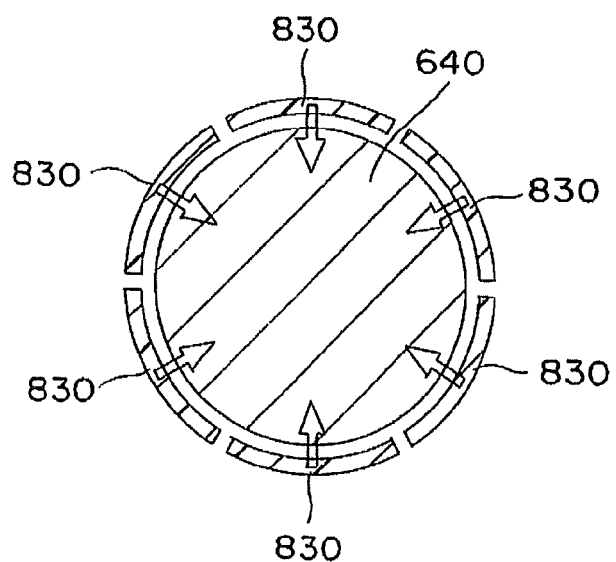

INTRODUCER ASSEMBLY

CROSS REFERENCES TO RELATED APPLICATIONS

This application is a continuation of International Application No. PCT/JP2011/055927 filed on Mar. 14, 2011, and claims priority to Japanese Application No. 2010-057808 filed on Mar. 15, 2010, Japanese Application No. 2010-148518 filed on Jun. 29, 2010, Japanese Application No. 2010-291703 filed on Dec. 28, 2010 and Japanese Application No. 2010-291674 filed on Dec. 28, 2010, the entire content of all five of which is incorporated herein by reference.

TECHNICAL FIELD

The present invention generally relates to an introducer assembly.

BACKGROUND DISCUSSION

It is common practice in modern medical treatment to perform treatment and testing of various kinds by using a medical instrument called a catheter which is a long thin tubular body. There are several methods for treating through use of a catheter as follows: administering drugs directly to the lesion owing to the length of the catheter; expanding a stenosis in the lumen with the help of a catheter having a balloon capable of inflation under pressure which is attached to the distal end of the catheter; opening a stenosis with the help of a catheter having a cutter attached at its distal end to shave off the lesion; and closing an aneurysm, nutritive blood vessel, bleeding part, etc. with a packing delivered by a catheter. Another treatment method involves placing a stent in the lumen with the help of a catheter to keep stenosis open with the help of a catheter. A sent is a cylindrical body whose side wall is of netlike structure. Further, extraction of excess fluid from the living body with the help of a catheter is another example of use.

The treatment and testing with a catheter are usually accomplished by percutaneously inserting a catheter into a blood vessel having a lesion through the lumen of an introducer sheath which is attached to a catheter introducer and punctured into the patient's arm or leg.

Japanese Patent Laid-open No. Hei 08-168532 discloses an introducer assembly which has an introducer sheath and a dilator which are previously integrated with each other so as to reduce work associated with assembling on the site of treatment and examination. The disadvantage of previously integrating an introducer sheath and a dilator with each other is that the resulting assembly in which the dilator tube passes through the hemostatic valve attached to the introducer sheath remains in such a state until it is actually used. The dilator tube passing through the hemostatic valve exerts a compressive force on the hemostatic valve for a rather long period of time. As a result, the hemostatic valve undergoes permanent set after a lapse in time. The resulting hemostatic valve would not completely arrest the flow of blood after the dilator tube has been pulled out. In the case of the introducer assembly disclosed in Japanese Patent Laid-open No. Hei 08-168532, this problem is addressed by forming the dilator tube in such a way that the part in its lengthwise direction which remains in contact with the hemostatic valve is smaller in outside diameter than any other parts. This structure protects the hemostatic valve from the compressive force acting on it for a long period of time, thereby allowing the hemostatic valve to fully function after the dilator tube has been pulled out.

However, making the dilator tube partly smaller in outside diameter suffers the disadvantage that the dilator tube receives a concentrated stress at the part where the diameter changes and hence tends to easily break. As a result, the dilator tube does not fully function as the core of the sheath tube which is the inherent function of the dilator tube.

SUMMARY

The examples of the introducer assembly disclosed here have an introducer sheath and a dilator which are previously integrated with each other in a manner allowing the hemostatic valve to remain functional for an extended period of time while also allowing the dilator tube to function smoothly.

According to one aspect, an introducer assembly comprises: an introducer sheath comprised of a sheath tube possessing a proximal end, a sheath hub attached to the proximal end of the sheath tube and possessing a proximal end portion, and a hemostatic valve attached to the proximal end portion of the sheath hub, the hemostatic valve possessing a through passage for a catheter to pass through; a dilator comprised of a dilator tube and a dilator hub, the dilator tube possessing a proximal end, the dilator hub being attached to the proximal end of the dilator tube; and a cap positioned between the sheath hub and the dilator hub, the cap possessing a through-hole. The dilator tube passes through the through-hole of the cap and passes through the through passage of the hemostatic valve, and the cap is positioned in a first position in which an engaging member on the cap and the sheath hub are spaced from one another, with the cap being axially movable in a distal direction to a second position in which the engaging member on the cap and the sheath hub engage one another to hold the cap at the second position. A deforming member is positioned between the hemostatic valve and the cap to press the hemostatic valve as the cap is moved to the second position to apply a compressive force to the hemostatic valve that causes closure of the passage in the hemostatic valve.

The introducer assembly is configured so that as the cap is moved to the second position, the deforming member presses the hemostatic valve and applies a compressive force to the hemostatic valve in such a direction as to close the passage. Therefore, the hemostatic valve may be left open and the dilator tube is left passing through the hemostatic valve with the hemostatic valve receiving only a small burden. And, during use, the hemostatic valve fully exhibits its hemostatic function even after the dilator tube has been pulled out. The dilator tube also exhibits its inherent function as the core of the sheath tube because the dilator tube does not need to be reduced in diameter over a portion of its length. Therefore, the introducer assembly disclosed here, in which the introducer sheath and dilator are previously integrated with each other, permits the hemostatic valve to exhibit its hemostatic function for an extended period of time. Moreover, the introducer assembly does not adversely affect the inherent function of the dilator tube.

According to another aspect, an introducer assembly comprises: an introducer sheath comprised of a sheath tube possessing a proximal end, a sheath hub attached to the proximal end of the sheath tube and possessing a proximal end portion and an axis extending in an axial direction, and a hemostatic valve attached to the proximal end portion of the sheath hub, the hemostatic valve possessing a through passage for a catheter to pass through; a dilator comprised of a dilator tube and a dilator hub, the dilator tube possessing a proximal end and a distal end, the dilator hub being attached to the proximal end of the dilator tube; with the dilator tube passing through the through passage of the hemostatic valve, and the dilator being movable in a proximal direction relative to the introducer sheath so that the dilator tube is removed from the through passage of the hemostatic valve; and a deforming member positioned between the sheath hub and the hemostatic valve. The deforming member is movable in a moving direction intersecting the axial direction of the sheath hub, after the dilator tube is removed from the through passage of the hemostatic valve as a result of the dilator being moved in the proximal direction relative to the introducer sheath, to press the hemostatic valve in a manner applying a compressive force to the hemostatic valve which closes the passage. An engaging member is positioned to be engaged by the sheath hub so that with the sheath hub in engagement with the engagement member the engaging member continues to press the hemostatic valve in a manner applying the compressive force to the hemostatic valve which closes the passage.

The introducer assembly is thus constructed so that as the deforming member, which is arranged between the sheath hub and the hemostatic valve, is moved in the direction intersecting the axial direction of the sheath hub to press the hemostatic valve, a compressive force is applied to the hemostatic valve in such a direction as to close the passage. Therefore, the hemostatic valve may be left open and the dilator tube is left passing through the hemostatic valve with the hemostatic valve receiving only a small burden. And, during use, the hemostatic valve fully exhibits its hemostatic function even after the dilator tube has been pulled out. The dilator tube is able to fully exhibit its inherent function as the core of the sheath tube because the dilator tube does not need to be reduced in diameter over a portion of its length. Therefore, the introducer assembly according to the present invention, in which the introducer sheath and dilator are previously integrated with each other, permits the hemostatic valve to exhibit its hemostatic function for a long period of time. Moreover, the introducer assembly does not adversely affect the inherent function of the dilator tube.

According to another aspect, an introducer assembly comprises an introducer sheath comprised of a sheath tube possessing a proximal end, a sheath hub attached to the proximal end of the sheath tube and possessing a tapering interior part tapering in a narrowing manner toward the sheath tube, and a hemostatic valve positioned in the tapering interior part and possessing a through passage for a catheter to pass through; a dilator comprised of a dilator tube possessing a proximal end and a dilator hub attached to the proximal end of the dilator tube, the dilator tube also possessing a distal end; and a cap possessing a through-hole and positioned between the sheath hub and the dilator hub. The dilator tube passes through the through-hole of the cap and passes through the through passage of the hemostatic valve, and the cap is positioned in a first position in which an engaging member on the cap and the sheath hub are spaced from one another, with the cap being axially movable in a distal direction to a second position in which the engaging member on the cap and the sheath hub engage one another to hold the cap at the second position. A deforming member is positioned between the hemostatic valve and the cap to move the hemostatic valve in the distal direction toward a distal end of the tapering interior part as the cap is axially moved toward the second position, with movement of the hemostatic valve in the distal direction toward the distal end of the tapering part applying a compressive force to the hemostatic valve in a direction closing the passage.

The introducer assembly is configured so that as the cap is moved to the second position, the deforming member moves the hemostatic valve toward the distal end of the tapering part, thereby applying a compressive force to the hemostatic valve in such a direction as to close the passage. Therefore, the hemostatic valve may be left open and the dilator tube is left passing through the hemostatic valve with the hemostatic valve receiving only a small burden. And, during use, the hemostatic valve fully exhibits its hemostatic function even after the dilator tube has been pulled out. Moreover, the dilator tube fully exhibits its inherent function as the core of the sheath tube because the dilator tube does not need to be reduced in diameter over a portion of its length. Therefore, the introducer assembly according to the present invention, in which the introducer sheath and dilator are previously integrated with each other, permits the hemostatic valve to exhibit its hemostatic function for a long period of time. Moreover, the introducer assembly does not adversely affect the inherent function of the dilator tube.

BRIEF DESCRIPTION OF DRAWINGS

FIG. 5(A) is a perspective view showing a hemostatic valve, FIG. 5(B) is a front view showing the hemostatic valve, FIG. 5(C) is a sectional view taken along the line 5C-5C in FIG. 5(B), and FIG. 5(D) is a rear view showing the hemostatic valve.

FIGS. 6(A), 6(B) and 6(C) are sectional views illustrating a passage of the hemostatic valve.

FIG. 7(A) is a perspective view showing a dilator hub, and FIG. 7(B) is a sectional view showing the dilator hub.

FIG. 8(A) is a perspective view showing the cap, and FIG. 8(B) is a sectional view showing the cap.

FIGS. 15(A) and 15(B) are sectional views illustrating the passage through the hemostatic valve pertaining to the modified example.

FIG. 21(A) is a plan view showing a hemostatic valve and a sheath hub which are not yet given a compressive force, and FIG. 21(B) is a perspective view showing the hemostatic valve which is not yet given a compressive force.

FIG. 22(A) is a plan view showing the hemostatic valve and the sheath hub which have been given a compressive force, and FIG. 22(B) is a perspective view showing the hemostatic valve which has been given a compressive force.

FIG. 27(A) is an enlarged view of that part of FIG. 24 which is encircled by the broken line 27A, and FIG. 27(B) is an enlarged view of that part of FIG. 25 which is encircled by the broken line 27B.

FIG. 38(A) is a perspective view showing the cap provided with a pressing member pertaining to a modified example of the pressing member, and FIG. 38(B) is a schematic sectional view illustrating how the hemostatic valve is pressed by the pressing member pertaining to the modified example.

DETAILED DESCRIPTION

Figure 1:
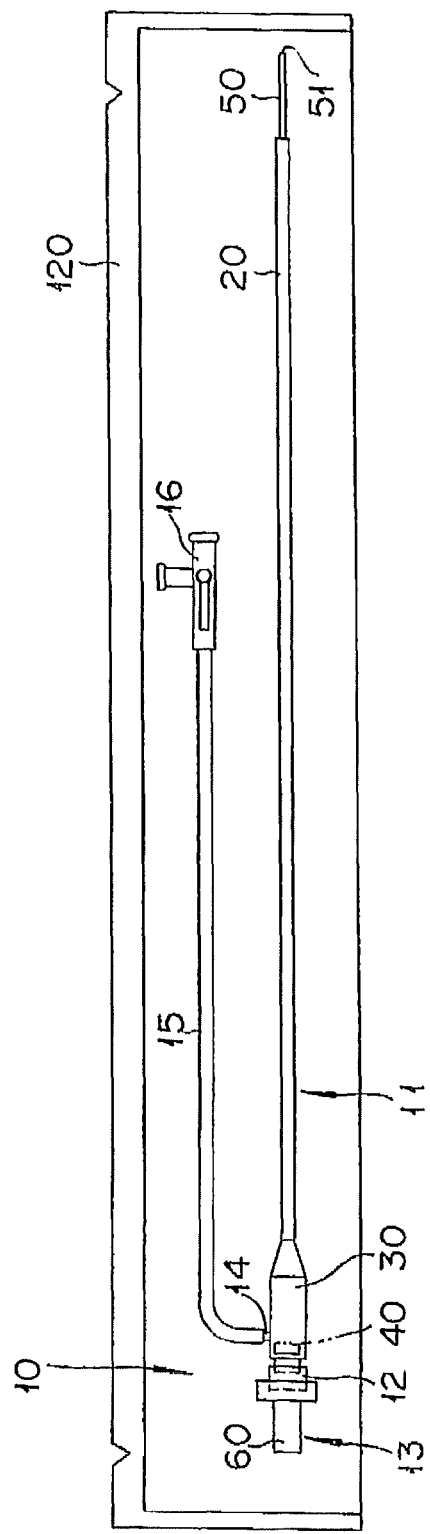
FIG. 1 is a plan view showing an introducer assembly pertaining to the first embodiment of the present invention which is packaged in a packaging film.

Set forth next, with reference to the accompanying drawing figures, is a description of a first embodiment of an introducer assembly, disclosed by way of example, in accordance with the disclosure here. In the drawings, the identical elements are referenced by the identical symbols to avoid duplicative explanations. The dimensions in the drawings may be exaggerated for the sake of explanation and may this differ from the actual dimensions.

An introducer assembly 10 is a device that permits one to secure an access route to the body cavity. In the following description, the term "proximal end" refers to that part of the device which is intended for operation by hand, and the term "distal end" refers to that part of the device which is inserted into the body cavity.

Figure 2:
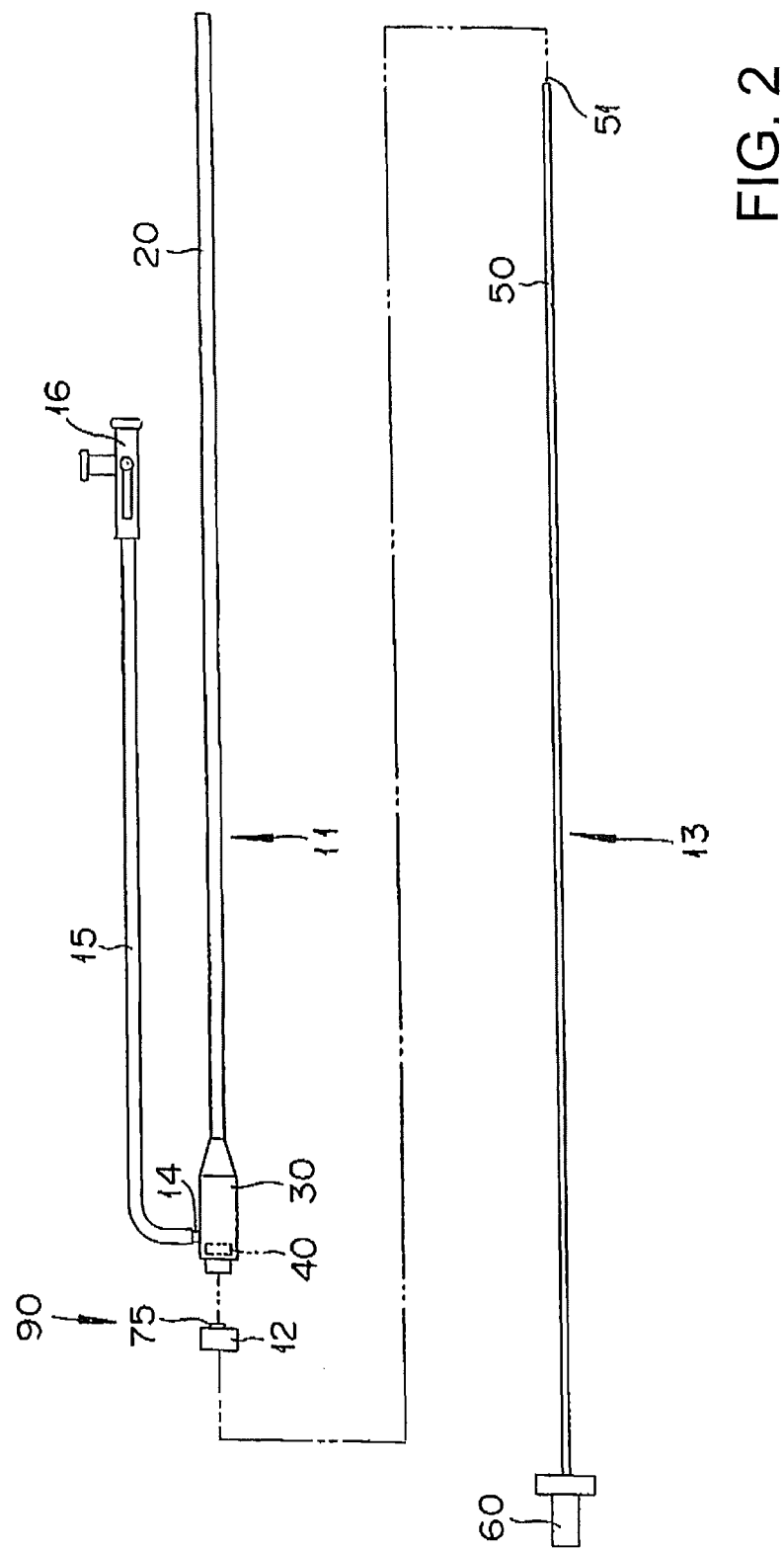
FIG. 2 is a plan view showing the introducer assembly which has been taken apart to an introducer sheath, a cap, and a dilator.
Figure 3:
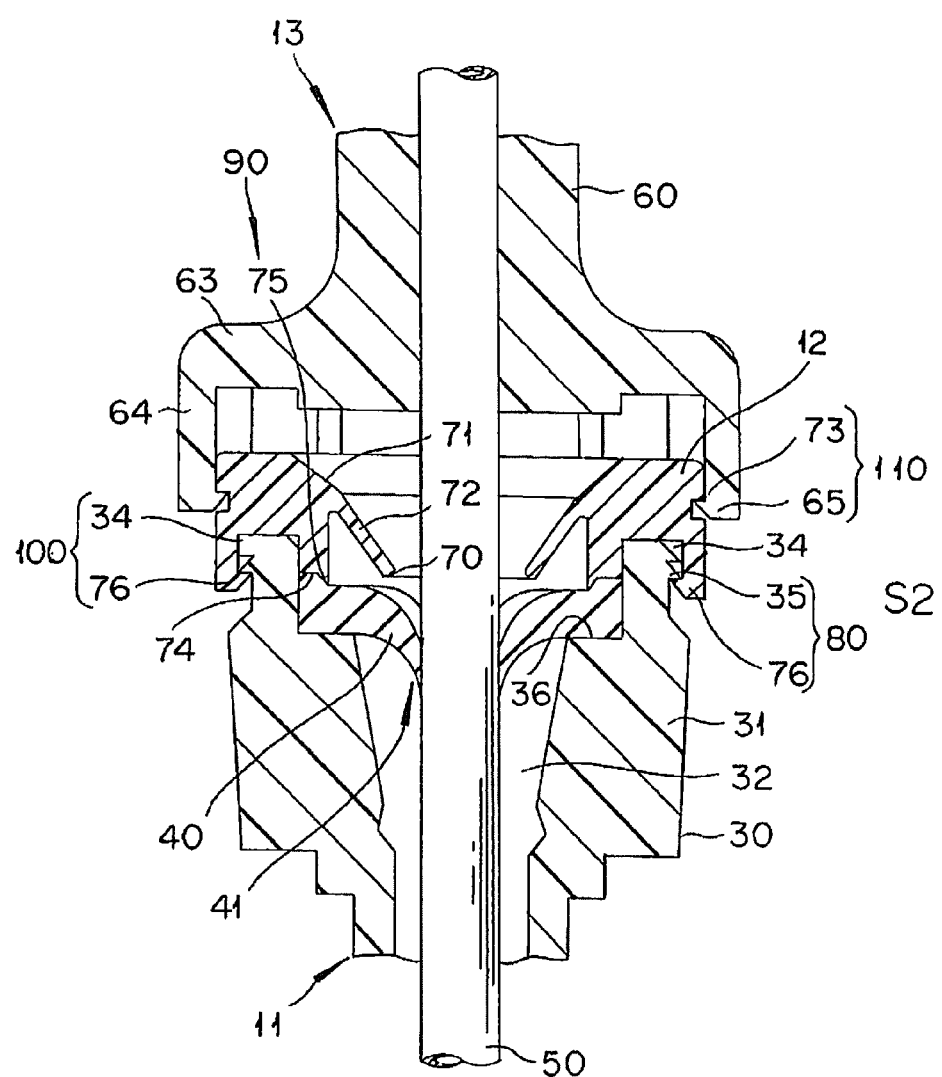
FIG. 3 is a sectional view showing an important part of the introducer assembly in which the cap has been moved to a second position where it engages with a sheath hub.

Referring to FIGS. 1-3, the introducer assembly 10 generally includes an introducer sheath 11, a cap 12, and a dilator 13. According to the introducer assembly 10 of the present embodiment, the introducer sheath 11 and the dilator 13 are previously integrated with each other to form an integrated part, and the entire assembly is packaged in a packaging film 120 (constituting an example of a packaging member). The introducer sheath 11 is composed of a sheath tube 20, a sheath hub 30 to which is attached the proximal end of the sheath tube 20, and a hemostatic valve 40 which is attached to proximal end of the sheath hub 30 and has a passage 41 for passage of the catheter. The dilator 13 has a dilator tube 50 and a dilator hub 60 attached to the proximal end of the dilator tube 50. The cap 12 has a through-hole 70 that permits the dilator tube 50 to pass through. The cap 12 is arranged between the sheath hub 30 and the dilator hub 60 in such a way that it is movable from the first position S1 (shown in FIG. 9) to the second position S2 (shown in FIGS. 3 and 10). The first position S1 is the position (disengaged state) in which the cap 12 is away from (spaced from) the sheath hub 30, and the second position S2 is the position (engaged state) where the cap 12 engages or contacts the sheath hub 30 when the cap 12 is pushed in the forward or distal direction toward the proximal end of the sheath hub 30.

The introducer assembly 10 further has an engaging member 80 and a deforming member 90. The engaging member 80 is formed on or mounted on the sheath hub 30 and the cap 12 to permit the cap 12 to engage the sheath hub 30, with the cap 12 held at the second position S2. The deforming member 90 is arranged between the hemostatic valve 40 and the cap 12, so that it presses the hemostatic valve 40, thereby applying a compressive force to the hemostatic valve 40 in such a direction as to close the passage 41 when the cap 12 is moved toward the second position S2. The passage 41 denotes the part which permits the dilator tube 50 to pass through (i.e., the part through which the dilator tube 50 passes) and which is capable of closing and opening. According to this embodiment, the deforming member 90 projects from the underside of the cap 12 (see "a pressing ring 75 as the pressing member" described later).

The introducer assembly 10 has the introducer sheath 11 and the dilator 13 previously integrated with each other, with the dilator tube 50 passing through the through-hole 70 of the cap 12 and the passage 41 of the hemostatic valve 40 and with the cap 12 held at the first position S1.

The following is a more detailed description of the introducer assembly 10. The introducer sheath 11 is sized and configured to be placed in the body cavity so that it permits a catheter, guide wire, plug, etc. to be introduced into the body cavity.

The sheath tube 20 is percutaneously introduced into the body cavity. The sheath tube 20 is formed from a polymeric material or a mixture of polymeric materials. Typical examples include polyolefin such as polyethylene, polypropylene, polybutene, ethylene-propylene copolymer, ethylene-vinyl acetate copolymer, ionomer, and mixture thereof, polyolefin elastomer, crosslinked polyolefin, polyvinyl chloride, polyamide, polyamide elastomer, polyester, polyester elastomer, polyurethane, polyurethane elastomer, fluoroplastics, polycarbonate, polystyrene, polyacetal, polyimide, and polyether imide.

The sheath hub 30 has a side port 14 which fluidly communicates with the sheath tube 20. To the side port 14 is fluid-tightly connected one end of a flexible tube 15 made of polyvinyl chloride. The other end of the tube 15 is attached to a three-way stopcock 16. For the purpose of priming, a liquid such as physiological saline is introduced into the introducer sheath 11 through one port of the three-way stopcock 16 and the tube 15.

Figure 4:
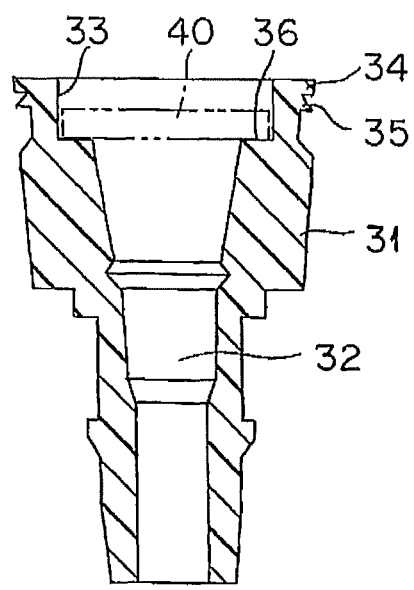
FIG. 4 is a sectional view showing the sheath hub.

As shown in FIG. 4, the sheath hub 30 is comprised of a sheath hub 31, a center hole 32 extending throughout the sheath hub 31, a holder 33 at the proximal end of the center hole 32 which holds the hemostatic valve 40, a first stepped part 34 on the outer circumference of the hub at the proximal end, and a second stepped part 35 also on the outer circumference of the hub at a position closer to the distal end than the first stepped part 34. The holder 33 has an inside diameter larger than that of the center hole 32. The holder 33 also has a ledge forming a supporting surface 36 in contact with the axial end of the hemostatic valve 40.

The sheath hub 30 should preferably be made of hard resin or the like, although not specifically restricted in this regard. Typical examples of hard resin include polyolefin such as polyethylene and polypropylene, polyamide, polycarbonate, and polystyrene.

As shown in FIGS. 5(A), 5(B), 5(C), and 5(D), the hemostatic valve 40 is a substantially film type member (discoid type or disc-shaped) made of an elastic material, and it is fluid-tightly fixed to the sheath hub 30. The hemostatic valve 40 has two axially facing sides, one referred to as the "surface" which faces the cap 12 and the other referred to as the "back side surface." The surface of the hemostatic valve 40 is oriented in the upward direction in FIG. 5(A) and in the front direction in FIG. 5(B).

The surface of the hemostatic valve 40 has a concave part 42 at the center of the valve. The center of the concave part 42 includes a first slit 43 which opens only to the axially facing surface. The concave part 42 functions as a guide for the tip of the dilator tube 50 or the catheter being inserted. The concave part 42 also serves to reduce the resistance to insertion. The back side surface of the hemostatic valve 40 includes a second slit 44 which also opens only to the axially facing back side surface. The first slit 43 and the second slit 44 cross or intersect each other so that their intersection serves as the passage 41 of the hemostatic valve 40. In other words, the passage 41 of the hemostatic valve 40 results by virtue of the overlap of the first and second slits 43, 44, with the former opening to the side of the hemostatic valve 40 which faces the cap 12 and the latter opening to the side of the hemostatic valve 40 which is opposite to or faces away from the cap 12. Each of the first and second slits 43, 44 exhibits the groove-like shape with a prescribed width (for example, about 0.5 mm). Consequently, the passage 41 of the hemostatic valve 40 has the small opening 45 before the dilator tube 50 is inserted into the passage 41 and the hemostatic valve 40 is pressed by the deforming member 90 (or while the hemostatic valve 40 is in an unloaded state).

The hemostatic valve 40 may be formed from any elastic material and is not limited to a specific material. Examples of materials which can be sued to form the hemostatic valve 40 include silicone rubber, latex rubber, butyl rubber, and isoprene rubber.

As shown in the cross-section of FIG. 6(A), the passage 41 of the hemostatic valve 40 has a small opening 45 before the dilator tube 50 is inserted into the passage 41 and the hemostatic valve 40 is pressed by the deforming member 90 or while the hemostatic valve 40 is in an unloaded state.

As shown in FIG. 6(B), the passage 41 of the hemostatic valve 40 is expanded and deformed by the dilator tube 50 as the dilator tube 50 is inserted into the passage 41. According to this embodiment, the passage 41 has the small opening 45, so that it deforms less than a passage having no small opening when the dilator tube 50 is inserted. Moreover, the concave part 42 also helps reduce deformation when the dilator tube 50 is inserted. Therefore, the passage 41 is restored to its initial shape shown in FIG. 6(A) owing to its elastic recovery force after the dilator tube 50 which has been inserted as described above is pulled out.

FIG. 6(C) is an exaggerated diagram illustrating how the hemostatic valve 40 deforms under pressure by the deforming member 90. Upon compression on at least its surface by the deforming member 90, the hemostatic valve 40 bends along the first slit 43, thereby closing the small opening 45 in its surface, making the passage 41 closed. In this way, the deforming member 90 presses the hemostatic valve 40, thereby applying a compressive force to the hemostatic valve 40 in such a direction as to close the passage 41. Thus, the hemostatic valve 40 prevents fluid such as blood from leaking from the proximal end of the dilator huh 60. In order for the hemostatic valve 40 to be deformed as described above, the hemostatic valve 40 takes on an ellipsoidal shape, having the short axis Sa and the long axis La, and the first slit 43 is formed along the short axis Sa as shown in FIG. 5(B). After deformation, the hemostatic valve 40 takes on a substantially circular shape in a plan view, which provides a uniform clearance in the circumferential direction between the outer peripheral edge part of the hemostatic valve 40 and the inner periphery of the housing 33 of the sheath hub 30. This helps provide keep good sealing.

The dilator 13 serves to help prevent the sheath tube 20 from sharply bending when the introducer sheath 11 is inserted into the blood vessel or to expand the perforation in the skin.

The dilator tube 50 passes through the sheath tube 20 such that a distal end part 51 of the dilator tube 50 exposes itself beyond the distal end of the sheath tube 20 as shown in FIG. 1. The dilator tube 50 may be configured to be held in the sheath tube 20 without the distal end part 51 of the dilator tube 50 exposing itself beyond the distal end of the sheath tube 20 until the cap 12 is pushed in.

The dilator tube 50 may be formed from a polymeric material or a mixture of polymeric materials. Examples of materials which can be sued to fabricate the dilator tube 50 include polyolefin such as polyethylene, polypropylene, polybutene, ethylene-propylene copolymer, ethylene-vinyl acetate copolymer, ionomer, and mixture thereof, polyolefin elastomer, crosslinked polyolefin, polyvinyl chloride, polyamide, polyamide elastomer, polyester, polyester elastomer, polyurethane, polyurethane elastomer, fluoroplastics, polycarbonate, polystyrene, polyacetal, polyimide, and polyether imide.

As shown in FIGS. 7(A) and 7(B), the dilator hub 60 is composed of a dilator hub 61, a center hole 62 formed in the dilator hub 61, and a flange 63 at the distal end of the dilator hub 61. The flange 63 is larger in outer diameter than the cap 12. In addition, the flange 63 has a plurality of arms 64 (four arms around the periphery, for instance) extending axially from the flange 63 toward the distal end. The individual arms 64 are capable of elastic deformation in the radially outward direction. A claw 65 is positioned at the distal end of each arm and projects radially inward.

The dilator hub 60 may be formed from any hard plastic material and is not limited to a specific material. Examples of materials for the dilator hub 60 include polyolefin such as polyethylene and polypropylene, polyamide, polycarbonate, and polystyrene.

As shown in FIGS. 8(A) and 8(B), the cap 12 possesses an approximately discoid shape. The cap 12 is so attached as to cover the proximal end of the sheath hub 30 as shown in FIG. 3. The cap 12 has two sides, one referred to as the "surface" which axially faces the dilator hub 60) and the other referred to as the "back side surface" which faces axially opposite to the surface.

The cap 12 is composed of an inclined surface 71 on the surface of the cap, a guiding part 72 which taperingly extends toward the distal end of the cap from the inclined surface 71, the centrally located through-hole 70 at the distal end of the guiding part 72, an annular groove 73 formed in the outer circumferential surface, a pressing surface 74 (radially extending pressing surface) which holds a peripheral part of the hemostatic valve 40 between the cap 12 and the supporting surface 36 of the sheath hub 30, and a pressing ring 75 projecting axially further toward the distal end from the pressing surface 74. At the distal end of the peripheral wall is formed an engaging claw 76 which projects radially inward. The inclined surface 71 and the guiding part 72 guide the distal end of the dilator tube 50 to the through-hole 70 when the dilator tube 50 and the catheter are passed through. The annular groove 73 detachably fits into the claw 65 on the arm 64 of the dilator hub 60 as shown in FIG. 3.

The cap 12 may be formed from any hard plastic material and is not restricted to a specific material. Examples of materials which can be used to fabricate the cap 12 include hard resins as polyolefin such as polyethylene and polypropylene, polyamide, polycarbonate, and polystyrene.

As shown in FIG. 3, according to this embodiment, the engaging member 80 is composed of the second stepped part 35 formed on the sheath hub 30 and the engaging claw 76 formed on the cap 12. The engaging claw 76 engages the second stepped part 35 so that the cap 12 engages the sheath hub 30 to be held at the second position S2. The engaging member 80 thus engages the cap 12 and the sheath hub 30 to hold the cap 12 at the second position S2.

In addition, according to this embodiment, the deforming member 90 has the pressing ring 75 (which corresponds to the pressing part) which projects axially from the end surface facing the hemostatic valve 40 of the cap 12. The pressing ring 75 functions as the deforming member 90 and is arranged between the hemostatic valve 40 and the cap 12. As the cap 12 is moved to the second position S2, the pressing ring 75 presses the hemostatic valve 40, thereby applying a compressive force in a direction closing the passage 41.

The introducer assembly 10 should preferably have the holding member 100 which holds the cap 12 at the first position S1 as the cap 12 is temporarily fixed to the sheath hub 30 or the dilator hub 60. This helps prevent the cap 12 from moving to the second position S2 until the introducer assembly 10 is put to use, so that the hemostatic valve 40 retains its hemostatic performance for a long period of time without the hemostatic valve 40 being deformed by continued compression. The holding member 100 according to this embodiment allows the cap 12 to be temporarily fixed to the sheath hub 30, and it is composed of the first stepped part 34 on the sheath hub 30 and the engaging claw 76 on the cap 12.

The introducer assembly 10 has a connecting member 110 which detachably connects the dilator hub 60 to the cap 12. The connecting member 110 according to this embodiment is composed of the annular groove 73 formed in the outer circumferential surface of the cap 12 and the claw 65 formed on the dilator hub 60. The connecting member 110 (composed of the annular groove 73 and the claw 65) connects the dilator hub 60 to the cap 12 with a force smaller than the force applied by the engaging member 80 (composed of the second stepped part 35 and the engaging claw 76) to hold the cap 12 at the second position S2. This permits the dilator 13 alone to be relatively easily removed after the cap 12 has been pushed to the second position S2.

The cap 12 is held at the first position S1 in such a state that gaps exist between the sheath 30, the cap 12, and the dilator hub 60. These gaps permit sterilization to be performed satisfactorily even when they are previously integrated with one another.

The following is a description of how the introducer assembly 10 operates or is used.

Figure 9:
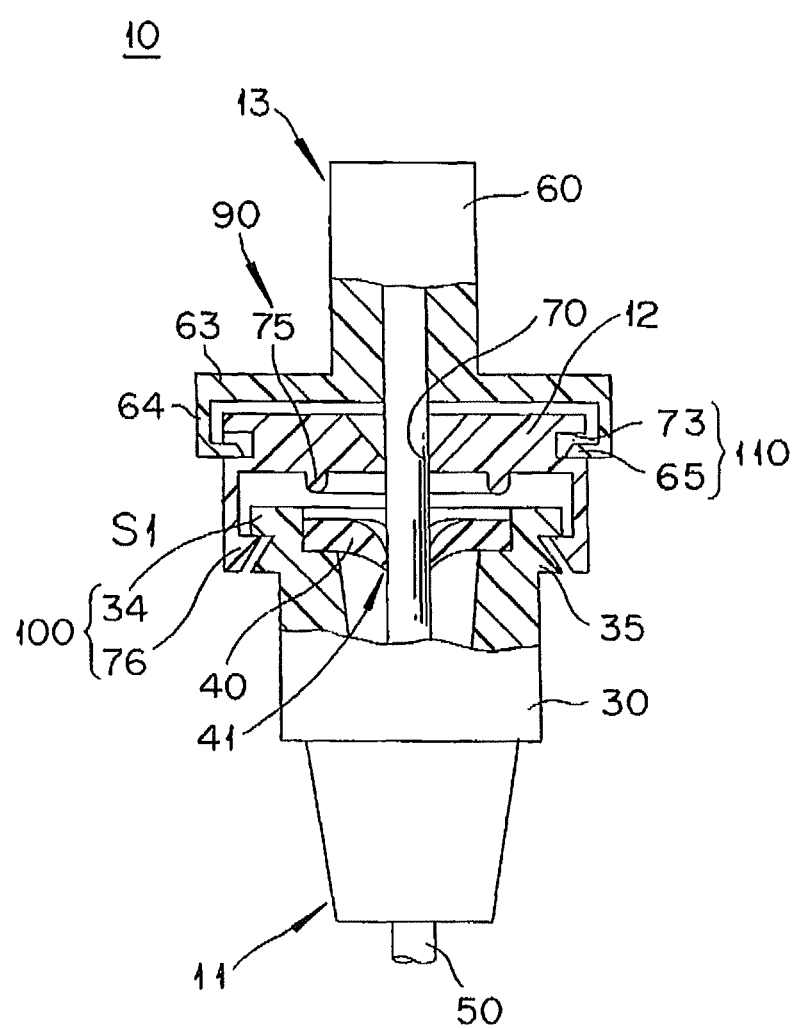
FIG. 9 is a schematic sectional view illustrating how the introducer assembly works, showing the state with the cap held at a first position away from the sheath hub and the dilator hub temporarily fixed to the cap.

As shown in FIG. 9, the introducer assembly 10 is constructed such that the dilator 13 is inserted into the introducer sheath 11 so that they are previously integrated when the cap 12 is held at the first position S1, with the dilator tube 50 passing through the through-hole 70 of the cap 12 and the passage 41 of the hemostatic valve 40. The cap 12 is temporarily fixed to the sheath hub 30 by the holding member 100 (composed of the first stepped part 34 and the engaging claw 76). The dilator hub 60 is temporarily fixed to the cap 12 by the connecting member 110 (composed of the annular ring 73 and the claw 65). The pressing ring 75 functioning as the deforming member 90 does not compress the hemostatic valve 40, so that the hemostatic valve 40 does not receive any compressive force in a direction closing the passage 41.

Figure 10:
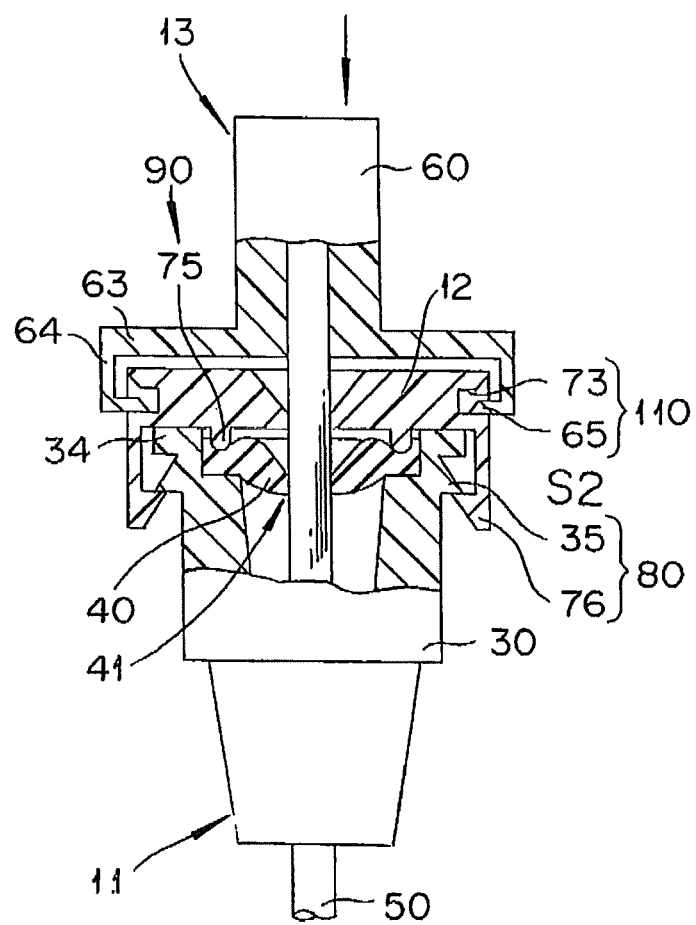
FIG. 10 is a schematic sectional view showing the introducer assembly which has changed from that shown in FIG. 9 in that the cap has moved to the second position where it engages with the sheath hub.

As shown in FIG. 10, the dilator 13 is pushed downward from the position shown in FIG. 9 so that the cap 12 pushed by the dilator 13 is also pushed downward. The downward movement of the cap 12 causes the engaging claw 76 which has been engaged with the first stepped part 34 to move beyond the second stepped part 35 to engage with the second stepped part 35. Thus the cap 12 engages with the sheath hub 30 so that it is held at the second position S2. The pressing ring 75 presses the hemostatic valve 40, thereby applying a force to the hemostatic valve 40 in such a direction as to close the passage 41.

Figure 11:
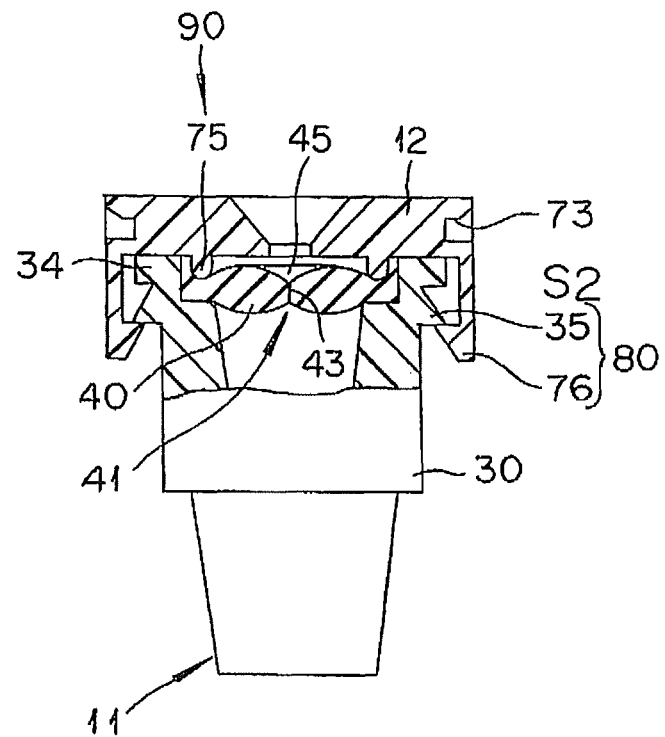
FIG. 11 is a schematic sectional view showing the cap-sheath hub assembly which has changed from that shown in FIG. 10 in that the dilator has been pulled out.

As shown in FIG. 11, the dilator 13 (i.e., the dilator hub 60 and the dilator tube 50) is then pulled out upward from the state shown in FIG. 10. Because the connecting member 110 which is composed of the annular groove 73 and the claw 65 temporarily fixes the dilator hub 60 to the cap 12 with a force which is smaller than the force applied by the engaging member 80 which is composed of the second stepped part 35 and the claw 76 to hold the cap 12 at the second position S2, the dilator 13 alone is readily removed after the cap 12 has been pushed to the second position S2. The pressing ring 75 presses the hemostatic valve 40, so that the hemostatic valve 40 receives a compressive force in a direction that closes the passage 41. In this way, the hemostatic valve 40 is pressed from its surface side by the pressing ring 75 so that it bends along the first slit 43 and the small opening 45 which has been previously open is closed at least in the surface side and the passage 41 becomes closed. Thus, the hemostatic valve 40 prevents the body fluid such as blood from leaking from the proximal end of the dilator hub 60.

The following is a brief description of the procedure for inserting a catheter by using the sheath introducer.

The first step is to make a hole at a desired position in the skin by using a needle, and the guide wire is inserted into the blood vessel, for example, through this hole. The guide wire is passed through the lumen of the introducer sheath 11 from the distal end of the introducer sheath 11. Then, the introducer sheath 11 is inserted into the blood vessel along the guide wire. At the time of insertion, the distal end part 51 of the dilator tube 50 expands the hole in the skin. Thus, the distal end of the introducer sheath 11 can be inserted into the blood vessel. After the introducer sheath 11 has been inserted into the blood vessel, the guide wire and the dilator 13 are pulled out, with the introducer sheath 11 left alone. In this way the introducer sheath 11 functions as a passage that connects the blood vessel to the outside of the body. This sheath permits the catheter or any other instrument to be inserted into the blood vessel.

As described above, according to the present embodiment, as the cap 12 is moved to the second position S2, the pressing ring 75 presses the hemostatic valve 40 and applies a compressive force to the hemostatic valve 40 in such a direction as to close the passage 41. Therefore, the hemostatic valve 40 may be left open and the dilator tube 50 is left in position passing through the hemostatic valve 40 until the introducer assembly 10 is put to use, with the hemostatic valve 40 receiving only a small burden. Furthermore, during use, the hemostatic valve 40 fully exhibits its hemostatic performance even after the dilator tube 50 has been pulled out. Moreover, the dilator tube 50 exhibits its inherent function as the core of the sheath tube 20 because the dilator tube 50 does not need to be reduced in diameter over a portion of its length. Therefore, the introducer assembly 10, in which the introducer sheath 11 and dilator 13 are previously integrated with each other, permits the hemostatic valve 40 to exhibit its hemostatic performance for an extended period of time. Moreover, the introducer assembly 10 does not interfere with the inherent function of the dilator tube 50.

The introducer assembly 10 having the introducer sheath 11 and the dilator 13 which are previously integrated with each other in shipping eliminates the necessity of assembling the parts at the working site for treatment and hence saves time for operation.

The fact that there is no need for assembling at the working site thoroughly eliminates the possibility of the dilator 13 bending at its distal end and the hemostatic valve 40 being damaged when the dilator 13 is inserted. The absence of the possibility of bending at the distal end and leaking from the hemostatic valve 40 leads to reduced invasiveness for the patient.

The introducer assembly 10 composed of the introducer sheath 11 and the dilator 13 which are previously integrated with each other is packaged in the packaging film 120 as shown in FIG. 1. Packaging the integrated introducer sheath 11 and dilator 13 in this way allows a smaller tray to be as compared to packaging the introducer sheath and the dilator in an un-integrated (i.e., separate) manner. This leads to space savings and material savings, which minimizes the energy loss that occurs in the manufacturing factory, the hospital, and the earth. The integrated introducer assembly 10 which is air-tightly sealed in the packaging film 120 is suitably protected from contamination during distribution before use.

Figure 12:
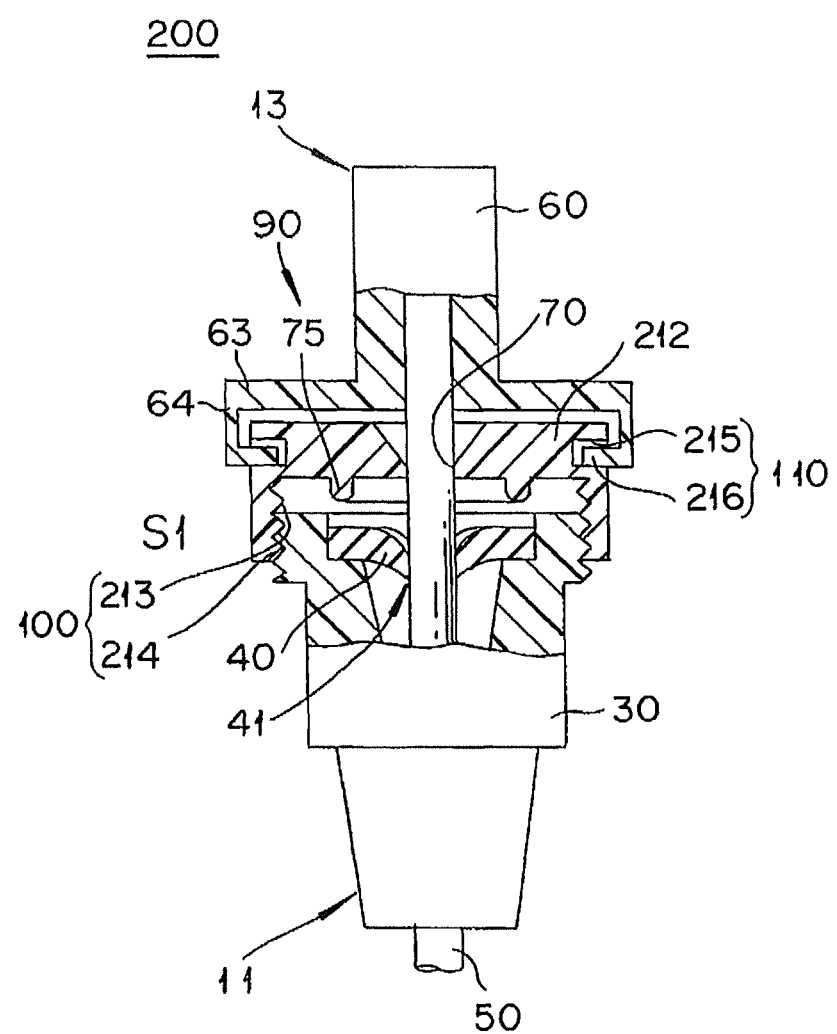
FIG. 12 is a schematic sectional view illustrating how the introducer assembly pertaining to a modification of the first embodiment works, with the cap held at the first position away from the sheath hub and the dilator hub temporarily fixed to the cap.
Figure 13:
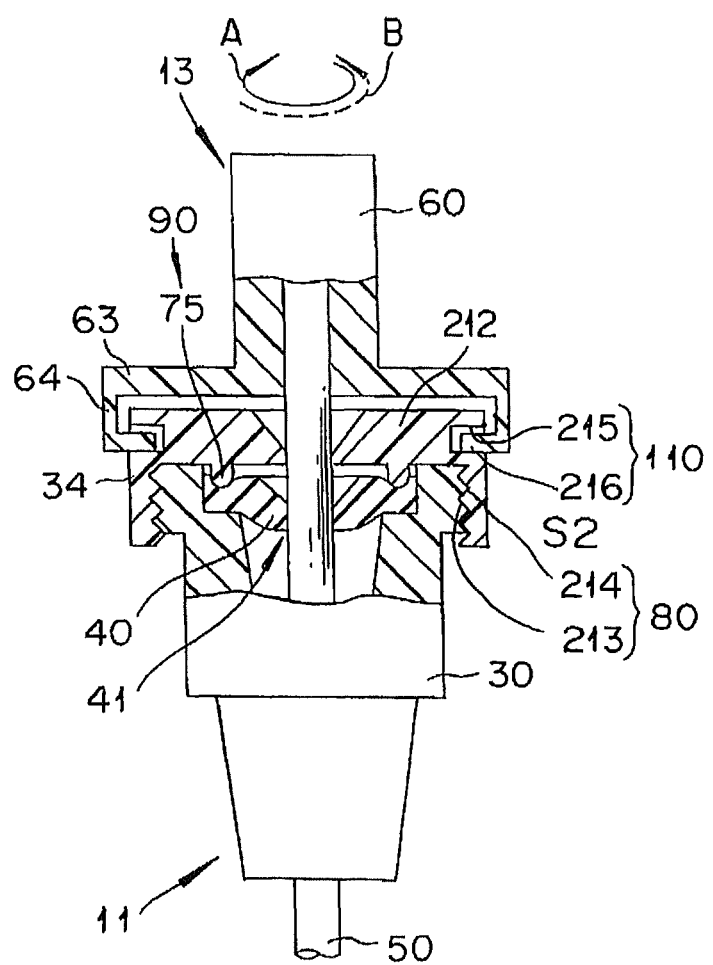
FIG. 13 is a schematic sectional view showing the introducer assembly which has changed from that shown in FIG. 12 in that the cap has moved to the second position where it engages with the sheath hub.

FIGS. 12 and 13 illustrate an introducer assembly 200 according to a modification of the first embodiment. The members in FIGS. 12 and 13 which are common to those in FIGS. 1 to 11 are identified by the same reference numerals and a detailed description of such features is not repeated here.

The introducer assembly 10 described above is constructed in such a way that the cap 12 is pushed toward the proximal end surface of the sheath hub 30 so that the cap 12 moves from the first position S1 which is away from the sheath hub 30 to the second position S2 at which it engages with the sheath hub 30. But the mechanism to move the cap 12 from the first position S1 to the second position S2 is not limited to that of the pressing type described above. The mechanism to move the cap 12 from the first position S1 to the second position S2 may be of a screw type as in the case of the introducer assembly 200 shown in FIGS. 12 and 13.

In other words, a cap 212 of the introducer assembly 200 freely moves from the first position S1 at which it is away from the sheath hub 30 (as shown in FIG. 12) to the second position S2 at which it engages with the sheath hub 30 (as shown in FIG. 13) as it is screwed toward the proximal end surface of the sheath hub 30. The cap 212 has a first screw part 213 on the inner periphery of the outer wall of the cap 212 and a second screw part 214 which meshes with the first screw part 213 on the outer peripheral edge part at the proximal end surface of the sheath hub 30.

The engaging member 80 to hold the cap 212 at the second position S2 and the engaging member 100 to hold the cap 212 at the first position S1 and temporarily fix the cap 212 to the sheath hub 30 are each comprised of the first screw part 213 of the cap 212 and the second screw part 214 of the sheath hub 30. To be more specific, the holding member 100 is composed of the lower end of the first screw part 213 in the figure and the upper end of the second screw part 214 in the figure, while the first screw part 213 and the second screw part 214 loosely mesh with each other as shown in FIG. 12. On the other hand, the engaging member 80 is composed of the screw parts 213, 214 in the region where the first and second screw parts 213 and 214 mesh with each other while the first screw part 213 and the second screw part 214 firmly mesh with each other as shown in FIG. 13.

The deforming member 90 is a projection formed on the lower surface of the cap 212 as in the case of the introducer assembly 10 explained above. FIGS. 12 and 13 illustrate this' projection 75 serving as a pressing ring or pressing part.

The connecting member 110 that detachably connects the dilator hub 60 to the cap 212 is composed of a groove 215 in the outer peripheral edge part of the cap 212 and a claw 216 on the distal end of the arm 64 of the dilator hub 60. The groove 215 and the claw 216 are so constructed as to turn the cap 212 and screw it into the sheath hub 30 as the dilator hub 60 is turned in the direction of the arrow A shown in FIG. 13. They are also so constructed as to disengage the dilator hub 60 from the cap 212 as the dilator hub 60 is turned in the opposite direction (direction indicated by arrow B in FIG. 13). For example, the groove 215 should have a stopper surface that comes into contact with the claw 216 when the dilator hub 60 is turned in the direction of the arrow A and also have a guide surface that permits the claw 216 to escape from the groove 215 when the dilator hub 60 is tuned in the direction of the arrow B. The foregoing structure may be modified such that the dilator hub 60 is disengaged from the cap 212, owing to the elasticity of the arm 64, when it is pulled in the axial direction.

A provision is made so that the force required by the connecting member 110 (composed of the groove 215 and the claw 216) to connect the dilator hub 60 to the cap 212 is smaller than the force required by the engaging member 80 (composed of the first screw part 213 and the second screw part 214) to hold the cap 212 at the second position S2. This provision permits one to relatively easily remove the dilator 13 alone (i.e., separate the dilator 13 from the rest of the assembly) after the cap 212 has been moved to the second position S2.

To use the introducer assembly 200, the dilator hub 60 is turned, thereby turning the cap 212 simultaneously, to screw the cap 212 into the sheath huh 30 and move the cap 212 from the first position S1 (shown in FIG. 12) to the second position S2 (shown in FIG. 13). The axially moved cap 212 causes the pressing ring 75 to press the hemostatic valve 40, thereby applying a compressive force to the hemostatic valve 40 in such a direction as to close the passage 41. As the dilator hub 60 is turned in the opposite direction as shown in FIG. 13, the dilator 13 alone can be easily removed from the cap 212. The pressing ring 75 presses the hemostatic valve 40, and the hemostatic valve 40 receives a compressive force in a direction closing the passage 41. Thus, the hemostatic valve 40 prevents the body fluid such as blood from leaking from the proximal end of the dilator hub 60.

Figure 14:
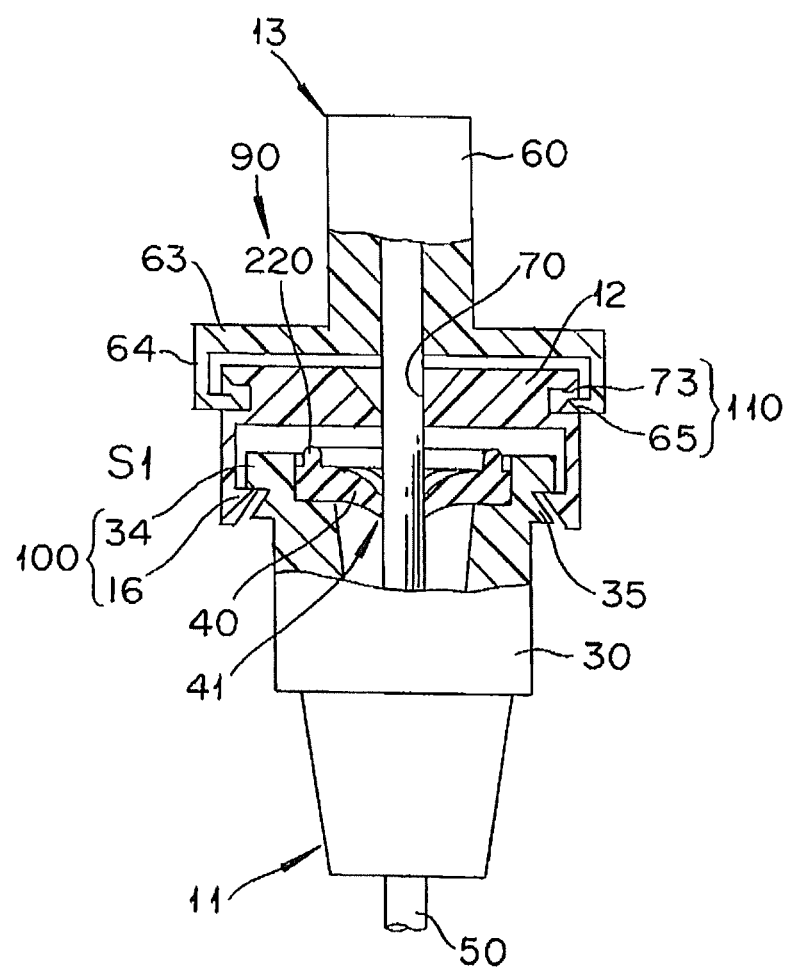
FIG. 14 is a schematic sectional view showing a modified example of a deforming member.

The introducer assembly disclosed here is not limited to the embodiments described above. For example, the introducer assembly is not limited to the deforming member 90 being the pressing ring 75 (pressing member) axially projecting from the end surface facing the hemostatic valve 40 of the cap 12. The deforming member 90 may be modified as required so long as it is arranged between the hemostatic valve 40 and the cap 12 and it presses the hemostatic valve 40, thereby applying a compressive force to the hemostatic valve 40 in such a direction as to close the passage 41 as the cap 12 is moved to the second position S2. An example of such modification is shown in FIG. 14, in which the deforming member 90 is an axially extending projection 220 formed on the end surface of the hemostatic valve 40 facing the cap 12. The projection 220 should preferably be formed integrally with the hemostatic valve 40 at the time of its molding. Alternatively, a projection member may be molded separately and attached to the hemostatic valve 40 later. It is also possible that that the pressing member/pressing part 75 can be independent of both the cap 12 and the hemostatic valve 40. For example, the independent pressing member/pressing part 75 can be arranged between the cap 12 and the hemostatic valve 40.

The hemostatic valve 40 is not specifically restricted in its structure. It may have a Y-shaped slit in a single layer or multiple layers, or it may be a duckbill valve having an X-shaped or I-shaped slit. Any other known valves may also be used.

The hemostatic valve 40 is not limited to the one which has the concave part 42 on its surface and also has the passage 41 at the bottom of the concave part 42. For example, a hemostatic valve 340 shown in FIG. 15(A) can be used. This hemostatic valve 340 has an inclined part 346 which tapers toward the cap 12. In the illustrated case, a passage 341 exists at a top part 347 of the inclined part 346. Because of the inclined part 346, the hemostatic valve 340 has a trapezoidal cross section. At the top part 347 is a recess 348 which serves as a guide surface for guiding the distal end of the dilator tube 50. At the center of the recess 348 is a first slit 343 that reaches only the surface (i.e., the first slit 343 does not reach or open to the back side surface). On the back side surface is a second slit 344 which reaches only the back side surface (i.e., the second slit 344 does not reach or open to the surface). The passage 341 is formed by arranging the first slit 343 and the second slit 344 in such a way that they cross each other at right angles. As in the case of the passage 41 in the valve described above, the passage 341 also has a small opening 345 which remains open when the dilator tube 50 has not yet been inserted and does not yet pass through the passage 341 and the hemostatic valve 340 is not yet pressed by the deforming member 90 and hence is free of load.

FIG. 15(B) is an exaggerated illustration showing the hemostatic valve 340 pressed by the deforming member 90 to be deformed. The hemostatic valve 340 is likely to concentrate the stress toward the central part of the passage 341 because an inclined part 346 bulging out toward the cap 12 in a convex manner is pushed down from the surface by the deforming member 90 that applies a downward compressive force. This deformation causes the surrounding of the passage 341 to swell upward, thereby closing the passage 341 rather easily. Therefore, the hemostatic valve 340 closes the passage 341 more tightly than the above-described hemostatic valve 40, thereby improving leakage resistance. In this way, it is possible to more effectively prevent the body fluid such as blood from leaking from the proximal end of the dilator hub 60.

Figure 16:
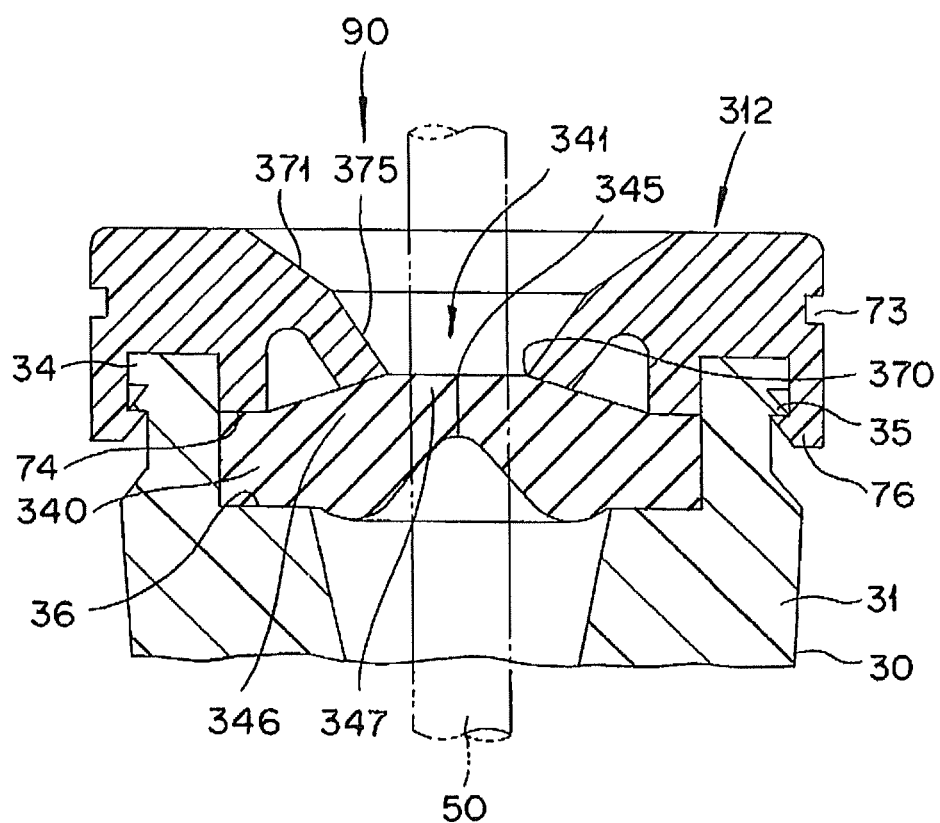
FIG. 16 is a schematic sectional view showing a modified example of a pressing part as the deforming member.

The deforming member 90 may be a pressing part projecting from that side of the cap 12 which faces the hemostatic valve. In the case of the foregoing embodiment, the pressing ring 75 functions as the pressing part. The pressing part may be modified as follows if the hemostatic valve 340 has the inclined part 346. In this case, the cap 312 shown in FIG. 16 has a tapered pressing guide 375 extending toward the incline part 346 of the hemostatic valve 340. The pressing guide 375 works in such a way that its distal end (or the lower end shown in the figure) comes into contact with the inclined part 346 as if it circularly surrounds the top part 347. The distal end of the pressing guide 375 may have an inclined surface or arched surface conforming to the surface of the inclined part 346. The pressing guide 375 works in such a way that its distal end presses the inclined part 346, thereby applying a compressive force to the hemostatic valve 340 in such a direction as to close the passage 341. The pressing guide 375 discussed above may be employed for the pressing part.

The pressing guide 375 continuously extends from an inclined surface 371 formed on the surface. The inclined surface 371 and the pressing guide 375 guide the distal end of the dilator tube 50 or the like to a through-hole 370 when the dilator tube 50 and the catheter are to be inserted. Therefore, the pressing guide 375 serves as both the guide 72 of the cap 12 and the pressing ring 75 described above.

The foregoing illustrates the pressing guide 375 which comes into contact with the inclined part 346 as if it circularly surrounds the vicinity of the top part 347. But the disclosure here is not limited to such a construction. The pressing part may be arranged parallel to the first slit 343 in the surface of the hemostatic valve 340 so that it applies compressive forces toward both sides of the first slit 343. The pressing part of this structure has the aligning mechanism which makes the pressing part parallel to the first slit 343 so that it applies a compressive force to the hemostatic valve 340, thereby closing the passage 341.

Figure 17:
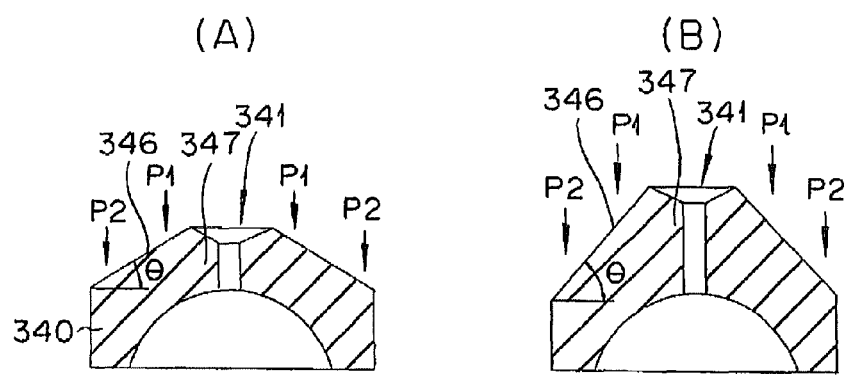
FIGS. 17(A) and 17(B) are diagrams illustrating the position at which a pressing guide presses an inclined part and the angle of inclination of the inclined part.
Figure 18:
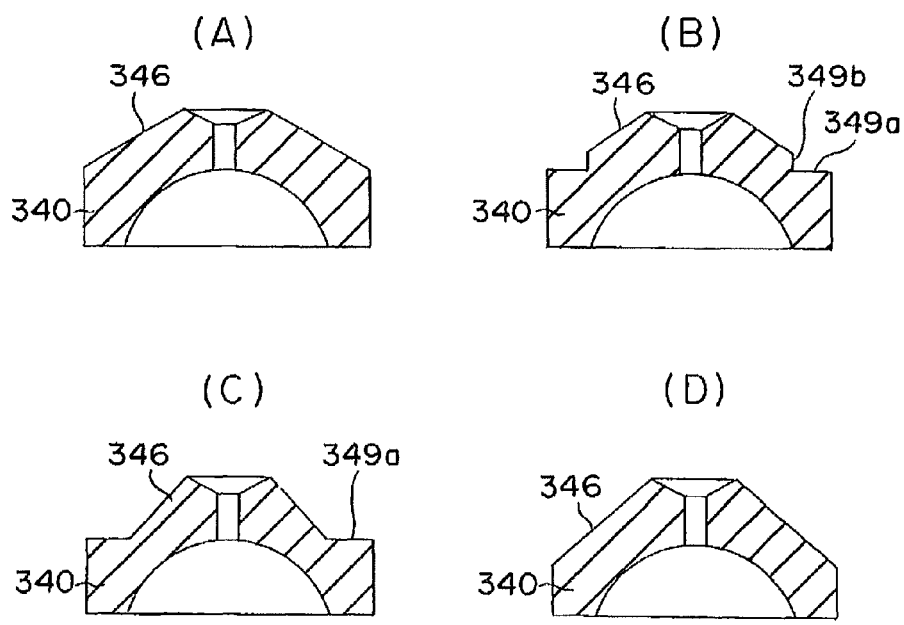
FIGS. 18(A) to 18(D) are sectional views showing a modified example of the shape of the hemostatic valve provided with the inclined part.

As shown in FIGS. 17(A) and 17(B), the pressing guide 375 should press the inclined part 346 at the position P1 which is near the top part 347 rather than the position P2 which is away from the top part 347. This results in a relatively strong force toward the center of the passage 341, thereby effectively closing the passage 341 and improving leakage resistance.

The inclined part 346 should preferably have a relatively large slope angle θ, so that there is obtained a strong force toward the center of the passage 341 and the passage 341 is surrounded by a larger mass. This closes the passage 341 effectively and improves leakage resistance.

The slope angle θ of the inclined part 346 and the position at which the pressing guide 375 presses the inclined part 346 should be properly established considering that the dilator tube 50 and the like smoothly passes through the passage 341 and the hemostatic valve 340 has an adequate size in its axial direction.

FIGS. 18(A) to 18(D) show some examples of the modified shape of the hemostatic valve 340 having the inclined part 346. The modified shapes may include a mountain shape (FIGS. 18(A) and 18(D)), a mountain shape with a radially extending flat part 349a on the outer peripheral part (FIGS. 18(B) and 18(C)), and a mountain shape with an axially extending step 349b between the inclined part 346 and the flat part 349a (FIG. 18(B)). If the flat part 349a is provided on the peripheral part, the hemostatic valve 340 should be held more stably by the pressing surface 74 shown in FIG. 16. According to this embodiment, the passage 341 is arranged at the top part 347 of the inclined part 346 of the hemostatic valve 340. However, the position of the passage is not specifically restricted so long as it is within the hemostatic valve.

A holding member 100 is so constructed as to temporarily fix the cap 12 to the sheath hub 30 by way of the first stepped part 34 and the engaging claw 76 or by way of the first screw part 213 and the second screw part 214. The introduces assembly is not limited to these examples. The holding part 100 may be so modified as to hold the cap 12 at the first position S1 by temporarily fixing the cap 12 to the dilator hub 60. In this case, the holding member 100 functions also as the connecting member 110 and hence the force to connect the dilator hub 60 to the cap 12 by the holding member 100 should be smaller than the force to hold the cap 12 at the second position S2 by the engaging member 80 (such as the second stepped part 35 and engaging claw 76).

The structures for connection between the sheath hub 30 and the cap 12 and between the cap 12 and the dilator hub 60 are not restricted to those illustrated above, but may be modified. In the foregoing case, the connection between the sheath hub 30 and the cap 12 is achieved by way of the first and second stepped parts 34 and 35 which are formed on the periphery of the sheath hub 30 and the engaging claw 76 projecting inward in the radial direction of the cap 12. However, this structure for connection may be modified such that the engaging claw which projects outward in the radial direction of the cap 12 engages the recess formed in the inner periphery of the sheath hub 30.

The structure for temporarily fixing the sheath hub 30, the cap 12, and the dilator hub 60 may optionally have an additional member to prevent them from rotating relative to one another.

Set forth below is a description of a second embodiment representing another example of the introducer assembly disclosed here. In the drawings, identical elements are identified by identical reference numerals and a detailed description of such features is not repeated. The dimensions in the drawings may be exaggerated for the sake of explanation and may thus differ from the actual dimensions.

In the following description, like the description above, the term "proximal end" refers to that part of the device which is intended for operation by hand, and the term "distal end" refers to that part of the device which is inserted into the body cavity.

The introducer assembly 410 will be described generally with reference to FIGS. 19, 20 and 25. The introducer assembly 410 has an introducer sheath 411 and a dilator 413. The introducer sheath 411 and the dilator 413 are previously integrated with each other, and the entire assembly is packaged in the packaging film 120 (constituting an example of a packaging member). The introducer sheath 411 is composed of a sheath tube 420, a sheath hub 430 to which is attached the proximal end of the sheath tube 420, and a hemostatic valve 440 which is attached to proximal end of the sheath hub 430 and has the passage 441 for the catheter. The dilator 413 has a dilator tube 450 and a dilator hub 460 attached to the proximal end of the dilator tube 450.

The introducer assembly 410 further has a deforming member 490 and an engaging member 480 (see FIGS. 21 and 22). The deforming member 490 is arranged between the sheath hub 430 and the hemostatic valve 440, so that it presses the hemostatic valve 440 to close its passage 441 when it is moved in the direction intersecting with the axial direction of the sheath hub 430 (as indicated by the arrows in FIGS. 22 and 25) to press the hemostatic valve 440. The passage 441 denotes the part which permits the dilator tube 450 to pass through and which is capable of closing and opening. The engaging member 480 permits the deforming member 490 to engage with the sheath hub 430, with the hemostatic valve 440 kept pressed.

Figure 24:
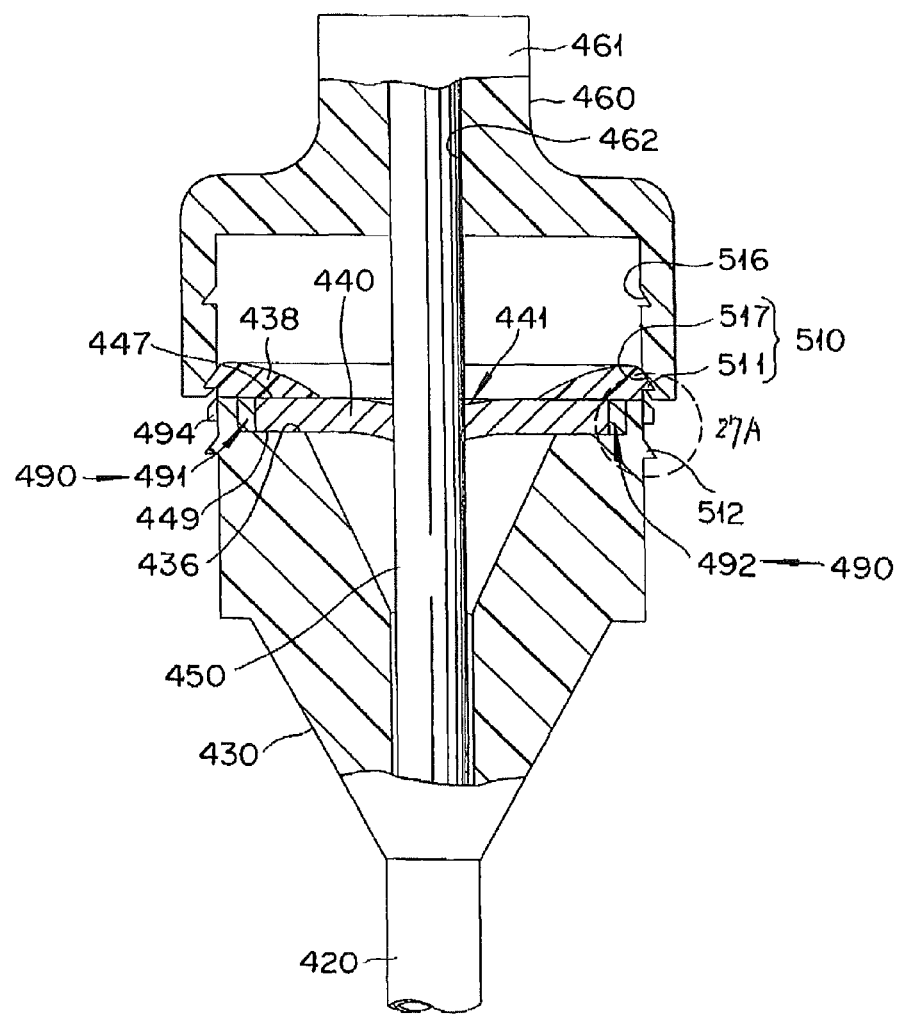
FIG. 24 is a schematic sectional view illustrating how the introducer assembly works, with the introducer sheath and the dilator temporarily fixed.

The introducer assembly 410, which is sealed in a package, has the introducer sheath 411 and the dilator 413 which are previously integrated with each other, in a state before the compressive force is applied, with the dilator tube 450 passing through the passage 441 of the hemostatic valve 440 as shown in FIG. 24. The following is a detailed description of the introducer assembly 410.

The introducer sheath 411 is intended to be placed in the body cavity so that it permits a catheter, guide wire, plug, etc. to be introduced into the body cavity.

The sheath tube 420 is percutaneously introduced into the body cavity.

The sheath tube 420 is formed from a polymeric material or a mixture of polymeric materials such as the following materials listed as examples: polyolefin such as polyethylene, polypropylene, polybutene, ethylene-propylene copolymer, ethylene-vinyl acetate copolymer, ionomer, and mixture thereof, polyolefin elastomer, crosslinked polyolefin, polyvinyl chloride, polyamide, polyamide elastomer, polyester, polyester elastomer, polyurethane, polyurethane elastomer, fluoroplastics, polycarbonate, polystyrene, polyacetal, polyimide, and polyether imide.

The sheath hub 430 has the side port 14 which communicates with the sheath tube 420. To the side port 14 is fluid-tightly connected one end of the flexible tube 15 made of polyvinyl chloride. To the other end of the tube 15 is attached the three-way stopcock 16. For the purpose of priming, a liquid such as physiological saline is introduced into the introducer sheath 411 through one port of the three-way stopcock 16 and the tube 15.

Figure 23:
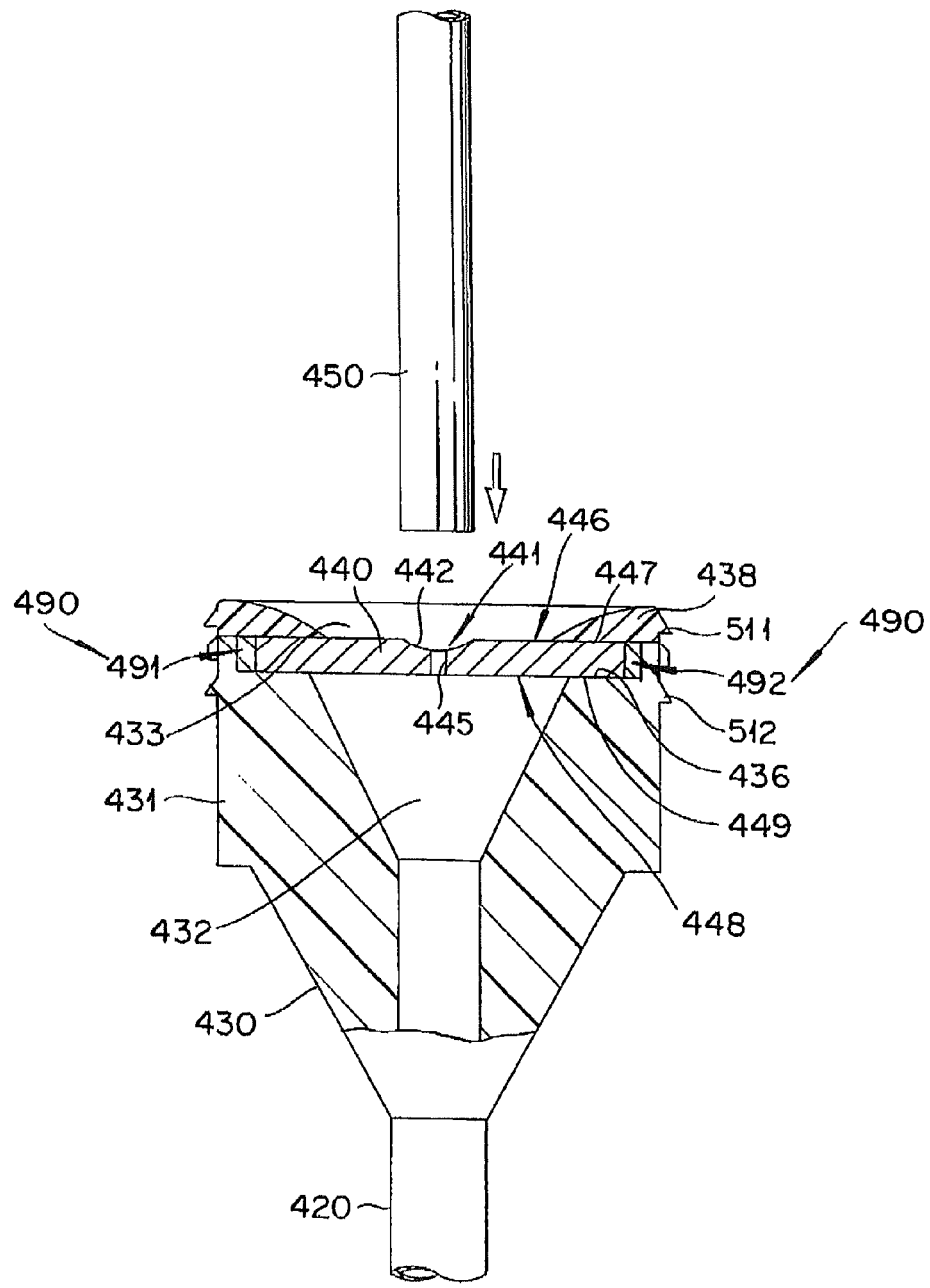
FIG. 23 is a schematic sectional view illustrating how the introducer assembly works, with the introducer sheath and the dilator not yet integrated with each other.

As shown in FIG. 23, the sheath hub 430 is made up of a sheath hub 431, a center hole 432 in the sheath hub 431, and a holder 433 at the proximal end of the center hole 432 which accommodates the hemostatic valve 440. The holder 433 has a supporting surface 436 which is in contact with an outer peripheral edge part 449 of a back side surface 448 of the hemostatic valve 440.

The sheath hub 430 has a pinching member 438 which holds the hemostatic valve 440 between the sheath hub 430 and the supporting surface 436 of the sheath hub 430. That is, the hemostatic valve 440 is held between the supporting surface 436 of the sheath hub 430 and the pinching member 438. The pinching member 438 takes on a frame-like shape, possesses a center hole, and is arranged in such a way that it comes into contact with an outer peripheral edge part 447 of a surface 446 of the hemostatic valve 440. The pinching member 438 is fixed to the sheath hub 430 in such a way that it holds the hemostatic valve 440 between the sheath hub 430 and the supporting surface 436. A fixing method may be adopted by fusion bonding, for example.

The pinching member 438 has an outwardly extending first projection 511 on its outer wall or outer surface. The sheath hub 431 has an outwardly extending second projection 512 on its outer wall or outer surface which is positioned closer to the distal end than the first projection 511 of the pinching member 438. The first projection 511 and the second projection 512 are to be used in combination with a first recess 516 and a second recess 517 which are formed in the inner wall or inner surface of the dilator hub 460. They function as a connecting member 530 for connection between the introducer sheath 411 and the dilator 413 as shown in FIGS. 25 and 27(B).

The sheath hub 430 and the pinching member 438 should preferably be made of hard material such as hard resin, although the specific material is not limited. Examples of materials which can be used to fabricate the sheath hub 430 include hard resin include polyolefin such as polyethylene and polypropylene, polyamide, polycarbonate, polystyrene, and the like.

As shown in FIGS. 21 and 22, the hemostatic valve 440 is a rectangular plat-shaped member made of an elastic material, and is fluid-tightly fixed to the sheath hub 430. The hemostatic valve 440 has two sides, one referred to as the "back side surface" 448 which faces the sheath tube 420 and the other referred to as the "surface" 446 which is the opposite side. In FIGS. 23 to 26, the surface 446 of the hemostatic valve 440 faces upward.

The hemostatic valve 440 has a groove 442 formed in the surface 446 of the hemostatic valve 440. The groove 442 extends in the direction perpendicular to the direction in which the deforming member 490 moves (in other words, it extends in the direction of the short side of the hemostatic valve 440). The groove 442 has a concave cross section (parallel to the lengthwise direction of the hemostatic valve 440 or in the direction in which the deforming member 490 moves). Moreover, the hemostatic valve 440 has the small opening 445 which is open under no-load condition when the hemostatic valve 440 is not yet pressed by the deforming member 490 before the dilator tuber 450 is passed through the passage 441.

The passage 441 of the hemostatic valve 440 undergoes deformation when it is expanded by the dilator tube 450 passing though it as illustrated in FIG. 24. Because the passage 441 has the small opening 445 which is open, it undergoes less deformation when the dilator tube 450 passes through it than would be the case if the small opening was not open. In addition, the groove 442 helps reduce the amount of deformation due to passage of the dilator tube 450. Therefore, for example, the passage 441 is restored to its original shape by its elastic restoring force after holding the state in that the compressive force is applied to the hemostatic valve 440 at first and then releasing the above described state.

FIGS. 21(B) and 22(B) schematically show before and after the hemostatic valve 440 deforms when pressed by the deforming member 490. Upon pressing inward by the deforming member 490, the hemostatic member 440 bends around the recessed groove 442 and entirely deforms, so that the entire shape of the hemostatic valve 440 curves outward projectingly toward the back side surface 448 side. As a result, the surface 446 deforms in such a way that the small opening 445 closes and hence the passage 441 closes. The groove 442 helps the hemostatic valve 440 to bend so as to relatively easily close the hemostatic valve 440 as a starting point of bending and also functions as a guide surface for guiding the distal end of the dilator tube 450 and the like, when the dilator tube 450 and the catheter are inserted, thereby reducing its resistance at the time of insertion.

The hemostatic valve 440 may be formed from any elastic material without specific restrictions. Its typical examples include silicone rubber, latex rubber, butyl rubber, and isoprene rubber.

The hemostatic valve 440 may be circular or ellipsoidal. However, a square one is desirable because it can be obtained by cutting a sheet-like piece in a square shape for using the hemostatic valve 440, and this permits a more effective use of material than circular and ellipsoidal ones. As a result, yield may be improved.

The deforming member 490 is composed of a first pressing member 491 and a second pressing member 492, which are so arranged in pairs as to hold the hemostatic valve 440 between them. Each of the first pressing member 491 and the second pressing member 492 has a pushing piece 493 which is arranged within the sheath hub 430 and a pushing member 494 which is formed integrally with the pushing piece 493 and whose end is arranged outside the sheath hub 430.

The engaging member 480 is composed of an engaging groove 481 which is formed in the sheath hub 430 and an engaging projection 482 which is formed on the deforming member 490 and is capable of engaging with and disengaging from the engaging groove 481. The engaging projection 482 is formed integrally with the pushing member 494 of the deforming member 490.

The first pressing member 491 and the second pressing member 492 move toward each other so as to press the side surfaces of the outer periphery of the hemostatic valve 440, thereby applying a compressive force to the hemostatic valve 440 in such a direction as to close the passage 441. The mutual approaching movement of the first pressing member 491 and the second pressing member 492 causes the engaging projection 482 to engage with the engaging groove 482, so that the first pressing member 491 and the second pressing member 492 engage the sheath hub 430.

The first pressing member 491 and the second pressing member 492 should preferably be made of hard material such as hard resin, although the specific material is no restricted. Typical examples of hard resin include polyolefin such as polyethylene and polypropylene, polyimide, polycarbonate, polystyrene, and the like.

The engaging projection 482 may be formed by resin molding integrally with the first pressing member 491 and the second pressing member 492 or may be formed by attaching a separately formed bead or ring which functions as an engaging projection. According to this embodiment, from a point of view of simple manufacturing process, a method of molding integrally with the first pressing member 491 and the second pressing member 492 is preferably employed.

The dilator 413 serves to prevent the sheath tube 420 from sharply bending when the introducer sheath 411 is inserted into the blood vessel or to expand the perforation in the skin.

Figure 19:
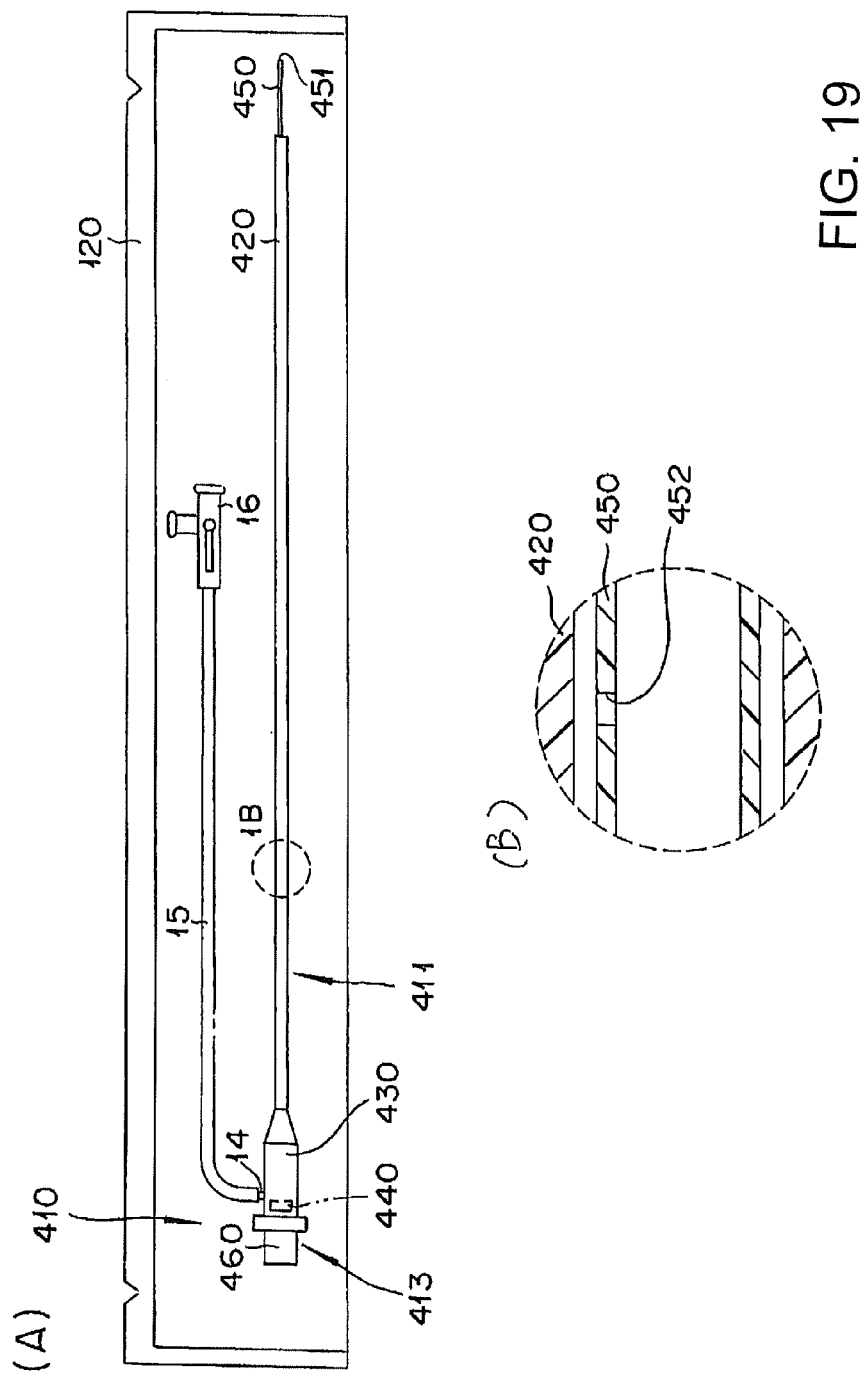
FIG. 19(A) is a plan view showing an introducer assembly pertaining to a second embodiment which is packaged in a packaging film.
FIG. 19(B) is an enlarged sectional view of that part of FIG. 19(A) which is encircled by the broken line 19B.
Figure 20:
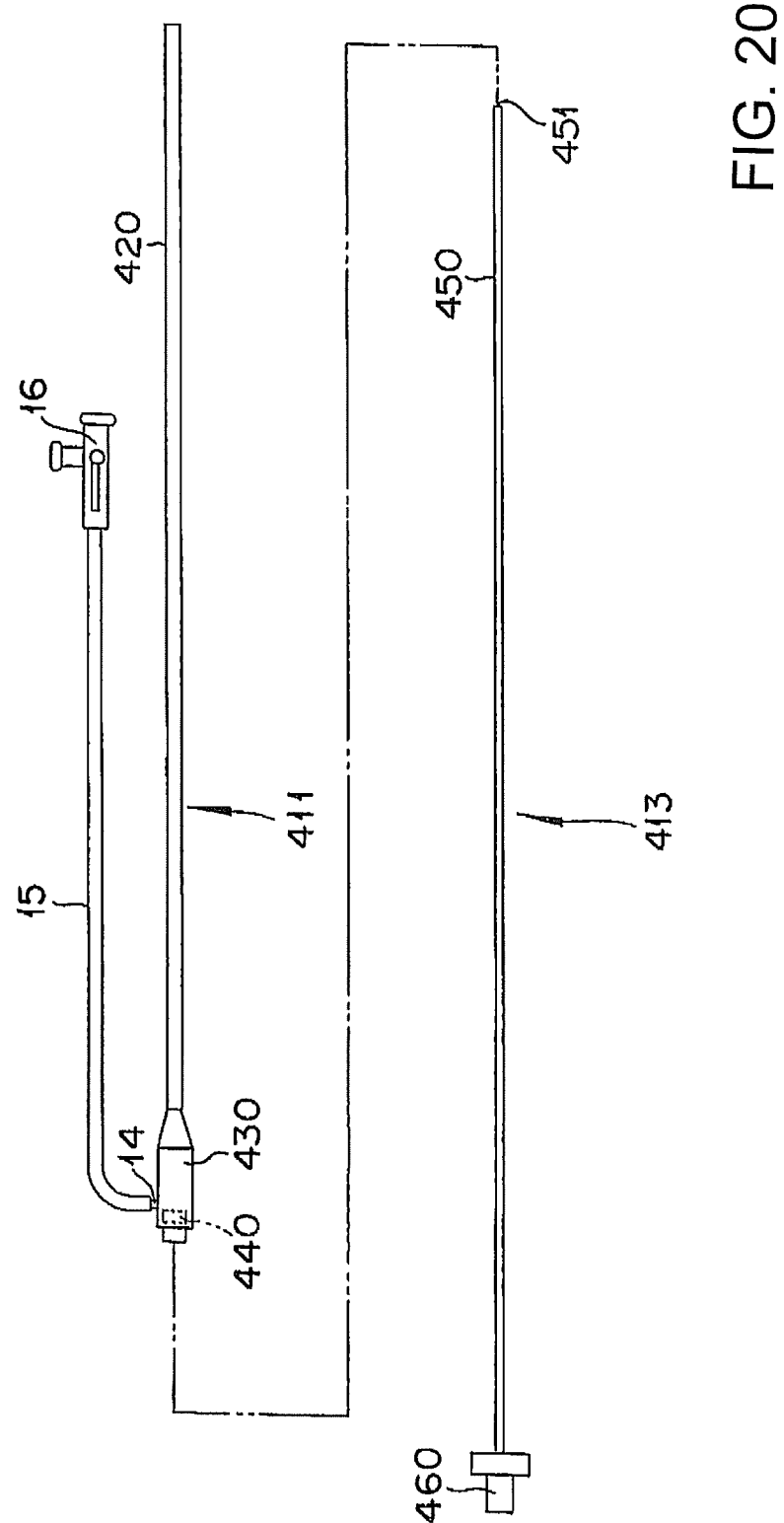
FIG. 20 is a plan view showing the introducer assembly which has been taken apart to an introducer sheath and a dilator.

The dilator tube 450 passes through the sheath tube 420 such that a distal end 451 of the dilator tube 450 exposes itself distally beyond the distal end of the sheath tube 420, as shown in FIG. 19. The dilator tube 450 may be held in the sheath tube 420 without the distal end 451 of the dilator tube 450 exposing itself beyond the distal end of the sheath tube 420 until a compressive force is applied to the hemostatic valve 440.

The dilator tube 450 has the opening 452 shown in FIG. 19(B) which permits a fluid to be supplied to the introducer sheath 411 to flow into the dilator tube 450 when the introducer sheath 411 and the dilator 413 are integrated with each other. When the introducer sheath 411 and the dilator 413 are integrated with each other, there exists a small clearance between the sheath huh 430 and the dilator tube 450 and between the sheath tube 420 and the dilator tube 450. Therefore, physiological saline to be supplied to the introducer sheath 411 for priming or EOG for sterilization to be supplied to the introducer sheath 411 will flow into the sheath hub 430 through an opening 452 formed in the dilator tube 450. This is the reason why priming and sterilization for the dilator tube 450 can be relatively smoothly accomplished even though the introducer sheath 411 and the dilator 413 are previously integrated with each other.

No specific restrictions are imposed on the number of openings 452 for fluid to flow into the dilator tube 450. There should preferably exist at least two openings to be capable of accelerating a relatively smooth circulation of fluid. The dimensions and shape of the opening are not specifically restricted.

The dilator tube 450 may be formed from a polymeric material or a mixture of polymeric materials such as the following materials which are listed as examples: polyolefin such as polyethylene, polypropylene, polybutene, ethylene-propylene copolymer, ethylene-vinyl acetate copolymer, ionomer, and mixture thereof, polyolefin elastomer, crosslinked polyolefin, polyvinyl chloride, polyamide, polyamide elastomer, polyester, polyester elastomer, polyurethane, polyurethane elastomer, fluoroplastics, polycarbonate, polystyrene, polyacetal, polyimide, and polyether imide.

As shown in FIG. 24, a dilator hub 460 has a dilator hub 461, a center hole 462 formed in the dilator hub 461, and the first recess part 516 formed in the inner wall of the dilator hub 461, and the second recess part 517 positioned distally of the distal end of the first concave part 516.

The dilator hub 460 may be formed from hard material such as hard resin. The specific type of hard resin is not limited, though typical examples of hard resin include polyolefin such as polyethylene and polypropylene, polyamide, polycarbonate, polystyrene, and the like.

The introducer assembly 410 has a holding member 510 which permits the introducer sheath 411 and the dilator 413 to be integrated before application of a compressive force when the dilator hub 460 is temporarily fixed to the sheath hub 430. The holding member 510 keeps the hemostatic valve 440 undeformed due to compression until the introducer assembly 410 is put to use, so that the integrated state is maintained during distribution. The holding member 510 is composed of the first projection part 511 which is formed on the pinching member 438 attached to the sheath hub 430 and the second recess part 517 formed in the dilator hub 460 as seen in FIG. 27(A). The first projection part 511 fits into the second recess part 517 so that the sheath hub 430 is temporarily fixed for connection to the dilator hub 460.

Figure 25:
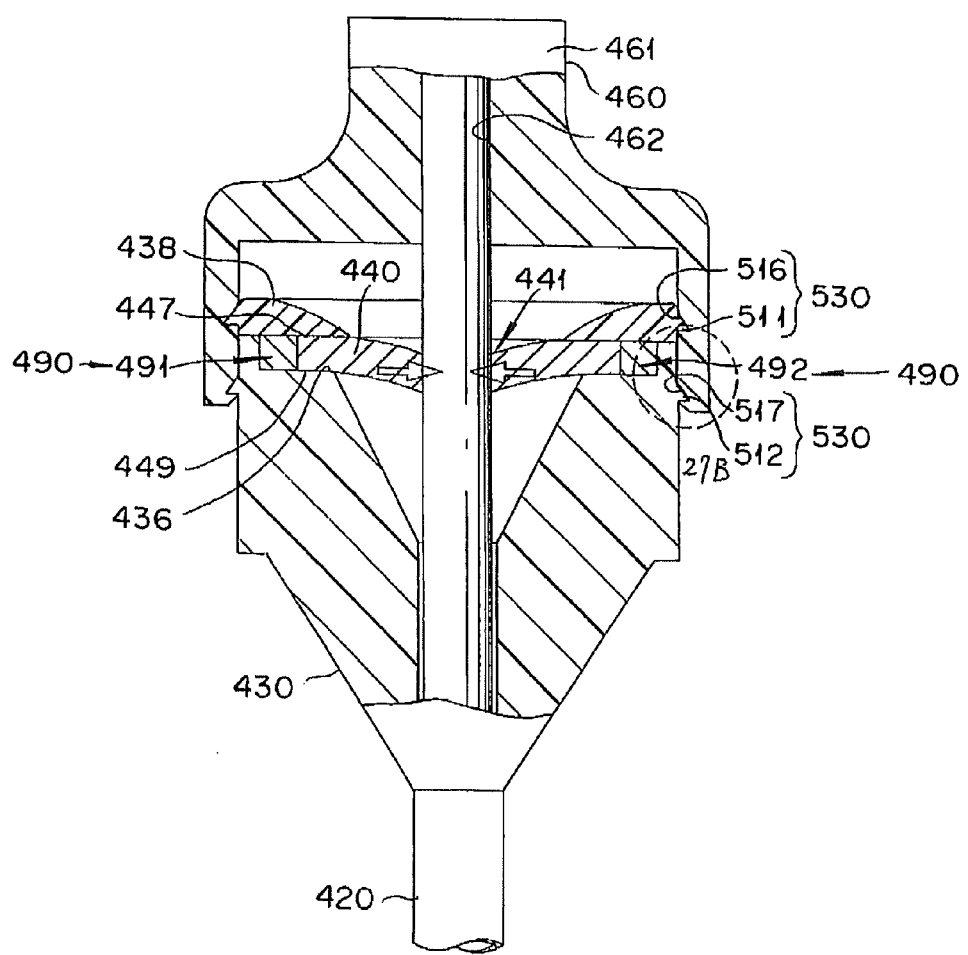
FIG. 25 is a schematic sectional view showing the introducer assembly which has changed from that shown in FIG. 24, with the dilator hub pushed into the sheath hub.

The introducer assembly 410 has the connecting member 530 which detachably connects the dilator hub 460 to the sheath hub 430 as the dilator hub 460 moves relative to the sheath hub 430 (see FIGS. 25 and 27(B)). According to this embodiment, the connecting member 530 is comprised of the first and second projections 511 and 512 formed on the sheath hub 430 and the first and second recesses 516 and 517 formed on the dilator hub 460. The first projection 511 and the second projection 512 are approximately identical in shape, and the first recess 516 and the second recess 517 are also approximately identical in shape. This structure permits the dilator hub 460 to be connected to the sheath hub 430 as the assembly shifts from the state in which the introducer sheath 411 is temporarily fixed to the dilator 413 by the first projection 511 and the second recess 517 to the state in which the dilator hub 460 is moved further toward the distal end so that the first projection 511 fits into the first recess 516 and the second projection fits into the second recess 517. As the dilator hub 460 is moved relative to the sheath hub 430, the pushing member 494 which is arranged outside the sheath hub 430 is pushed toward the inside of the sheath hub 430, so that the first pressing member 491 and the second pressing member 492 approach each other, thereby applying a compressive force to the hemostatic valve 440. At this time, the first pressing member 491 and the second pressing member 492 are engaged with the sheath hub 430 by the engaging member 480.

The first and second projections 511 and 512 and the first and second recesses 516 and the 517 are not specifically restricted in their shape so long as they are capable of maintaining the connected state of the sheath hub 430 and the dilator hub 460. They should preferably have the shape which permits relatively smooth connection and disconnection as the dilator hub 460 moves relative to the sheath hub 430. According to this embodiment, the connecting member 530 is composed of the recess and the rib-shaped projection which permits relatively easy fitting into and disengagement from the recess.

At the distal end of the dilator hub 460 is a guide surface 513, shown in FIG. 27, which has a slope angle approximately equal to that of the inclined surface of the first and second projections 511 and 512 and that of the inclined surface of the pushing member 494. The guide surface 513 permits the dilator hub 460 to slidingly move relative to the sheath hub 430 for connection and also permits the pushing member 494 to be relatively smoothly pushed into the sheath hub 430 in concert with the sliding movement when the dilator hub 460 is connected.

The following is a description of how the introducer assembly 410 operates or is used.

As shown in FIG. 23, the dilator hub 460 is temporarily fixed to the sheath hub 430 before a compressive force is applied to the hemostatic valve 440 in such a direction as to close the passage 441. The dilator 413 is moved toward the introducer sheath 411 so that the dilator tube 450 passes through the passage 441 of the hemostatic valve 440. This procedure is rather easy to perform because the groove 442 of the hemostatic valve 440 guides the dilator tube 450 being inserted.

As shown in FIG. 24, the dilator hub 450 is temporarily fixed to the sheath hub 430 by the holding member 510 (the first projection 511 and the second recess 517). Thus, the introducer sheath 411 and the dilator 413 are previously integrated with each other, and the resulting assembly is ready for distribution. That is, the introducer sheath 411 and the dilator 413 in the previously integrated condition (i.e., the condition in which the dilator hub 450 is temporarily fixed to the sheath hub 430 by the holding member 510) is packaged in the packaging film 120.

In the temporarily fixed state, the first pressing member 491 and the second pressing member 492 both constituting the deforming member 490 do not yet compress the hemostatic valve 440 and so no compressive force is yet applied to the hemostatic valve 440 to close the passage 441.

As shown in FIG. 25, the dilator 413 is pushed down from the position shown in FIG. 24, so that the sheath hub 430 is connected to the dilator hub 460 by the connecting member 530 (the first and second projections 511 and 512, and the first and second recesses 516 and 517).

The movement of the dilator hub 460 pushes the pushing member 494 which is arranged outside of the sheath hub 430 into the sheath hub 430. Thus, the first pressing member 491 and the second pressing member 492 come close to each other (move towards one another) in the direction intersecting with the axial direction of the sheath hub 430, thereby pressing the hemostatic valve 440 toward the center axis of the sheath hub 440. A compressive force is applied to the hemostatic valve 440 in such a direction as to close the passage 441.

The engaging member 480 causes the first and second pressing members 491 and 492 to engage with the sheath hub 430, thereby keeping the hemostatic valve 440 pressed.

Figure 26:
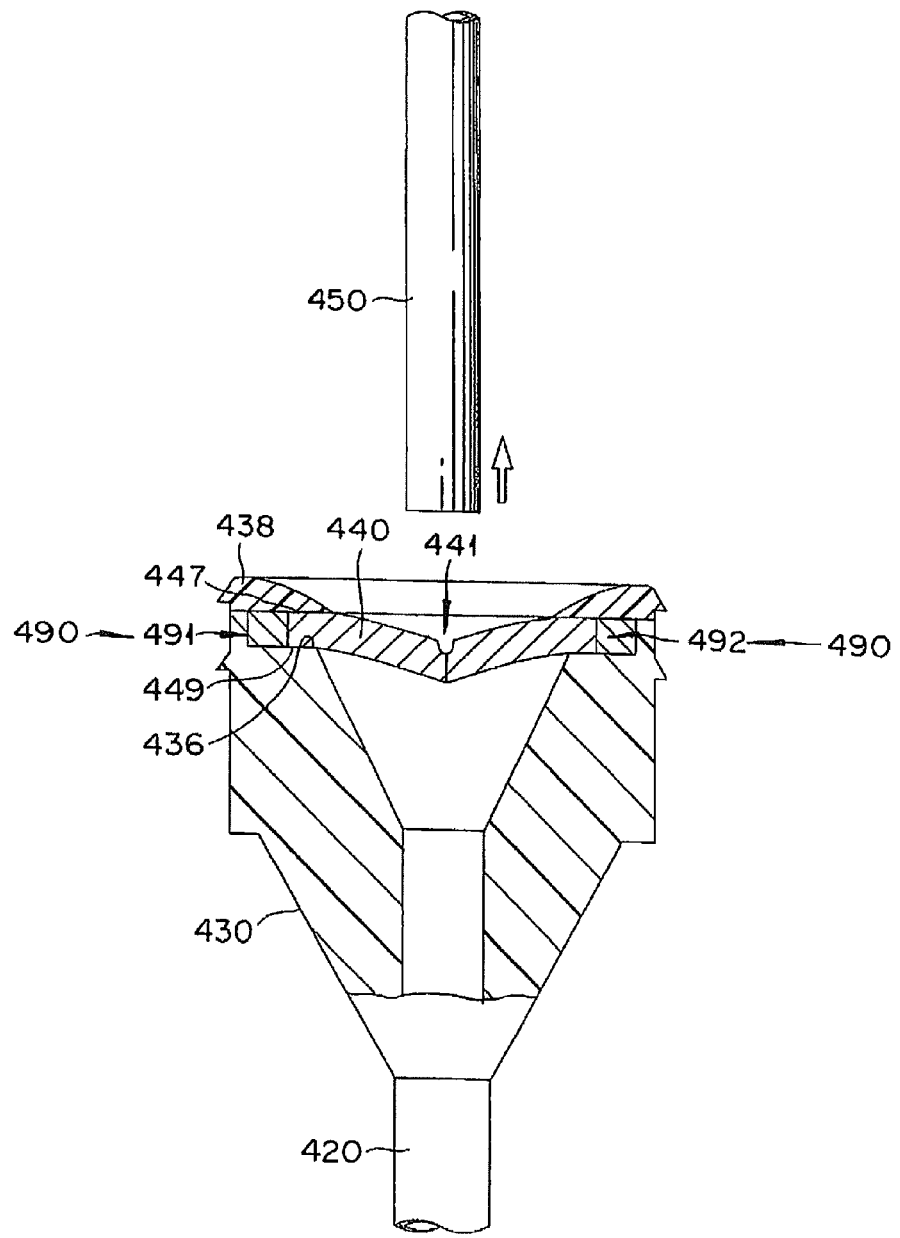
FIG. 26 is a schematic sectional view showing the introducer sheath which has changed from that shown in FIG. 25, with the dilator pulled out.

As shown in FIG. 26, the dilator tube 450 is pulled out from the passage 441 of the hemostatic valve 440. With the dilator tube 450 pulled out, the engaging member 480 continues to apply a compressive force to the hemostatic valve 440 in such a direction as to close the passage 441. Thus, the passage 441 is kept closed and the hemostatic valve 440 prevents the leakage of fluid such as blood from the proximal end of the dilator hub 460.

The groove 442 permits the hemostatic valve 440 to deform rather easily and hence the small opening 445 in the hemostatic valve 440 is reliably closed.

The hemostatic valve 440 has the outer peripheral edge part 447 of its surface 446 and the outer peripheral edge part 449 of its back side surface 448 held between the pinching member 438 and the supporting surface 436 of the sheath hub 460. Therefore, the hemostatic valve 440 keeps its projecting shape bulging toward the back side surface 448 side thereof. There is no possibility of the hemostatic valve 440 becoming deformed bulging toward the surface 446 side or being displaced.

The following is a brief description of the procedure for inserting a catheter by using the introducer sheath 411.

The first step is to make a hole at a desired position in the skin by using an introducer needle, and the guide wire is inserted into the blood vessel, for example, through the hole. The guide wire is passed through the lumen of the introducer sheath 411 from the distal end of the introducer sheath 411. Then, the introducer sheath 411 is inserted into the blood vessel along the guide wire. At the time of insertion, the distal end 451 of the dilator tube 450 expands the hole in the skin. Thus, the distal end of the introducer sheath 411 can be inserted into the blood vessel. After the introducer sheath 411 has been inserted into the blood vessel, the guide wire and the dilator 413 are pulled out, with the introducer sheath 411 left alone. In this way the introducer sheath 411 functions as a passage that connects the blood vessel to the outside of the body. Thus, the introducer sheath 411 permits the catheter or any other instrument to be inserted into the blood vessel.

As mentioned above, this embodiment produces the following effects. As the deforming member 490 which is arranged between the sheath hub 430 and the hemostatic valve 440 is moved in the direction intersecting the axial direction of the sheath hub 430 (radially inward direction) and presses the hemostatic valve 440, a compressive force is applied to the hemostatic valve 440 in such a direction as to close the passage 441. Therefore, the hemostatic valve 440 is left open and the dilator tube 450 is left passing through the hemostatic valve 440 before use, with the hemostatic valve 440 receiving only a small burden. And, during use, the hemostatic valve 440 fully exhibits its hemostatic function even after the dilator tube 450 has been pulled out. Moreover, the dilator tube 450 exhibits its inherent function as the core of the sheath tube 420 because the dilator tube 450 does not need to be reduced in diameter over a portion of its length. Therefore, the introducer assembly 410, in which the introducer sheath 411 and dilator 413 are previously integrated with each other, permits the hemostatic valve 440 to exhibit its hemostatic function for a long period of time. Moreover, the introducer assembly 410 does not adversely affect the inherent function of the dilator tube 450.

The introducer assembly 410 having the introducer sheath 411 and the dilator 413 previously integrated with each other eliminates the necessity of assembling the parts at the working site for treatment and hence saves time for operation.

The fact that there is no need for assembling at the working site thoroughly eliminates the possibility of the dilator 413 bending at its distal end and the hemostatic valve 440 being damaged when the dilator 413 is inserted. The absence of the possibility of bending at the distal end and leaking from the hemostatic valve 440 leads to reduced invasiveness for the patient.

The introducer assembly 410, which is composed of the introducer sheath 411 and the dilator 413 which are previously integrated with each other, is packaged in the packaging film 120 as shown in FIG. 19. Packaging the integrated introducer sheath 411 and dilator 413 in this way allows a smaller tray to be as compared to packaging the introducer sheath and the dilator in an un-integrated (i.e., separate) manner. This leads to space savings and material savings, which minimizes the energy loss that otherwise occurs in the manufacturing factory and the hospital, and further on the earth. The integrated introducer assembly 410 which is air-tightly sealed in the packaging film 120 is adequately protected from contamination during distribution before use.

The hemostatic valve 440 is constructed such that its side surfaces of the outer periphery are pressed as the first pressing member 491 and the second pressing member 492 arranged in pairs as to hold the hemostatic valve 440 between them are moved toward each other so that it is deformed toward the central axis of the sheath hub 440. In this way the passage 441 of the hemostatic valve 440 is adequately closed.

The hemostatic valve 440 has the groove 442 formed in the surface 446 of the hemostatic valve 440, so that it is fairly easily deformed by bending at the groove 442. This structure helps reliably close the passage 441 formed in the hemostatic valve 440.

The hemostatic valve 440 has the outer peripheral edge part 447 of the surface 446 thereof and the outer peripheral edge part 449 of the back side surface 448 thereof held between the pinching member 438 and the sheath hub 430, which prevents it from deforming (bulging toward the surface 446 of the hemostatic valve 440) and displacing. This protects the operator (using the dilator 413) from anomalous hand feeling due to deformation and displacement of the hemostatic valve 440.

A simple operation to move the dilator hub 460 relative to the sheath hub 430 is enough to connect the dilator hub 460 to the sheath hub 430 and to apply a compressive force to the hemostatic valve 440. This helps improve the handleability of the introducer assembly 410 for the user's convenience.

The introducer sheath 411 and the dilator 413, which are previously integrated with each other, permit the dilator tube 450 to undergo priming and sterilization relatively smoothly because the dilator tube 450 is supplied with physiological saline or FOG which is fed into the introducer sheath 411 through the opening 452 formed in the wall of the dilator tube 450.

Figure 28:
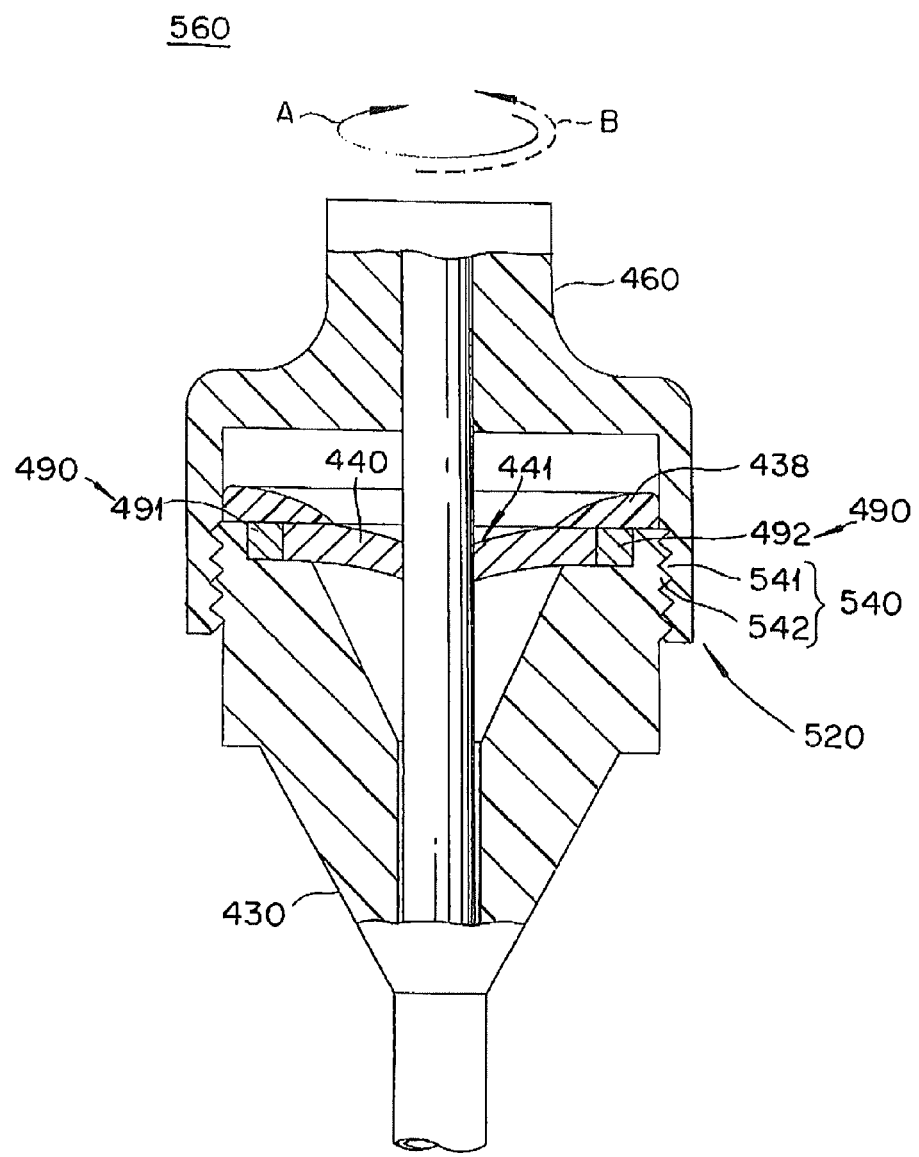
FIG. 28 is a schematic sectional view illustrating a modified example of a holding member and a connecting member.

FIG. 28 is a schematic sectional view illustrating an example of a modified version of the holding member and the connecting member. The features in FIG. 28 which are common to those in FIGS. 19 to 27 are identified by the same reference numerals and a detailed description of such features is not repeated.

According to the introducer assembly 410 described above, the holding member 510 which temporarily fixes the sheath hub 430 and the dilator hub 460 to each other and the connecting member 530 which detachably connects both members 430 and 460 to each other are of fitting type which is composed of the first and second projections 511 and 512 and the first and second recesses 516 and 517. However, according to this embodiment, the mechanism for temporary fixing and detachable connecting the sheath hub 430 and the dilator hub 460 is not restricted to that of fitting type. It may be of screw type which is employed in an introducer assembly 560 shown in FIG. 28.

In the modified case, a holding member 520 and a connecting member 540 are composed of a first screw part 541 which is formed on the inner wall surface at the distal end of the dilator hub 460 and a second screw part 542 meshing with the first screw part 541, which is formed on the outer wall surface of the sheath hub 430. The first screw part 541 and the second screw part 542 constitute the connecting member 540 when they firmly mesh with each other. Also, the lower end portion of the first screw part 541 and the upper portion of the distal end of the second screw part 542 constitute the holding member 520 when they loosely mesh with each other.

The first screw part 541 and the second screw part 542 mesh with each other in such a way that the dilator hub 460 screws into the sheath hub 430 as the dilator hub 460 is turned in the direction of arrow A in FIG. 28, and the dilator hub 460 unscrews from the sheath hub 430 as the dilator hub 460 is turned in the opposite direction of arrow B.

The screw mechanism as in the modified case facilitates connection between the dilator hub 460 and the sheath hub 430 and application of a compressive force to the hemostatic valve 440 by the simple operation of screwing or moving the dilator hub 460 into the sheath hub 430.

Application of a compressive force to the hemostatic valve 440 is not restricted to the one which involves connection between the dilator hub 460 and the sheath hub 430 by the connecting members 520 and 540. The same effect as described above will be obtained if the operator who handles the introducer assembly presses the pressing member directly by hand, thereby pressing the hemostatic valve.

Pressing of the hemostatic valve 440 may be accomplished in any other way than moving the two members such as the first pressing member 491 and the second pressing member 492. Any way of pressing may be employed so long as it permits movement in the direction intersecting the axial direction of the sheath hub (radially inward direction), thereby applying a compressive force to the hemostatic valve 440. Thus, possible modifications will include pressing by a single deforming member and pressing by two or more pressing members in pairs.

Although the hemostatic valve 440 in square shape has been demonstrated in this embodiment, the shape is not specifically restricted to square. Circle and ellipse are also acceptable. It is also possible to form the dilator hub having a circular shape in accordance with the outer shape of the hemostatic valve, thereby assuring rather easy handling.

The following is a description of a third embodiment of the introducer assembly, referring to the accompanying drawings. As in earlier embodiments, features which are the same as in earlier embodiments are identified by the same reference numerals and a detailed description of such features is not repeated. The dimensions in the drawings may be exaggerated for the sake of explanation and different from the actual ones.

The introducer assembly 610 provides an access route to the body cavity. In the following description, the term "proximal end" refers to that part of the device which is intended for operation by hand, and the term "distal end" refers to that part of the device which is inserted into the body cavity.

The introducer assembly 610 will be generally described with reference to FIGS. 29, 30, and 34. The introducer assembly 610 has an introducer sheath 611, a cap 612, and a dilator 613. According to the introducer assembly 610 of this embodiment, the introducer sheath 611 and the dilator 613 are previously integrated with each other, and the entire assembly is packaged in the packaging film 120 (constituting an example of a packaging member). The introducer sheath 611 is composed of a sheath tube 620, a sheath hub 630 to which is attached the proximal end of the sheath tube 620, which has the tapering part 634 which tapers toward the distal end of the sheath tube 620, and a hemostatic valve 640 which is held by the tapered part 634 of the sheath hub 630 and has a passage 641 for the catheter to pass through. The dilator 613 has a dilator tube 650 and a dilator hub 660 attached to the proximal end of the dilator tube 650. The cap 612 has a through-hole 670 that permits the dilator tube 650 to pass through. The cap 612 is arranged between the sheath hub 630 and the dilator hub 660 in such a way that it is movable from a first position S1 (shown in FIG. 33) to a second position S2 (shown in FIG. 34). The first position S1 is the position which is away from the sheath hub 630 and the second position S2 is the position where the cap 612 engages the sheath hub 630 when it is pushed from the proximal end side of the sheath hub 630.

The introducer assembly 610 further has an engaging member 680 and a deforming member 690. The engaging member 680 is formed on the sheath hub 630 and the cap 612, so that it permits the cap 612 to engage with the sheath hub 630, with the cap 612 held at the second position S2 illustrated in FIG. 34. The deforming member 690 is arranged between the hemostatic valve 640 and the cap 612, so that it applies the compressive force to the hemostatic valve 640 to close its passage 641 when the cap 612 is moved toward the second position S2 and the hemostatic valve 640 is moved to the distal end or the tapering part 634. The passage 641 denotes the part which permits the dilator tube 650 to pass through and which is capable of closing and opening.

Figure 33:
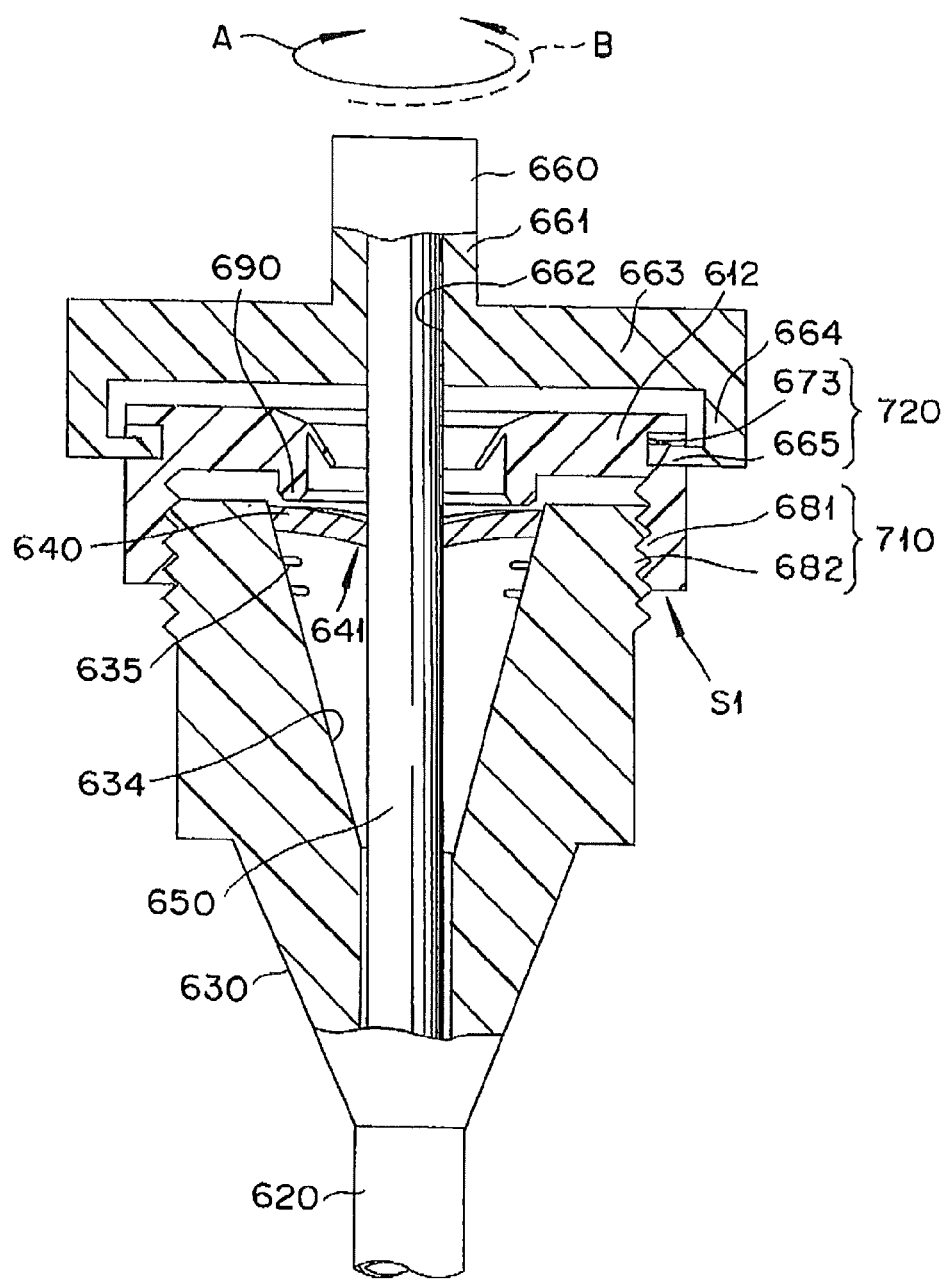
FIG. 33 is a schematic sectional view illustrating how the introducer assembly works, with the cap held at a first position away from the sheath hub and the dilator hub temporarily fixed to the cap.

The introducer assembly 610 which is sealed in an air-tight package as shown in FIG. 33 has the introducer sheath 611 and the dilator 613 previously integrated with each other, with the dilator tube 650 passed through the through-hole 670 of the cap 612 and the passage 641 of the hemostatic valve 640 and with the cap 612 held at the first position S1. The following is a detailed description of the introducer assembly 610.

The introducer sheath 611 is intended to be placed in the body cavity so that it permits, for example, a catheter, guide wire, plug, etc. to be introduced into the body cavity.

The sheath tube 620 is percutaneously introduced into the body cavity.

The sheath tube 620 is formed from a polymeric material or a mixture of polymeric materials. Examples of typical materials include polyolefin such as polyethylene, polypropylene, polybutene, ethylene-propylene copolymer, ethylene-vinyl acetate copolymer, ionomer, and mixture thereof, polyolefin elastomer, crosslinked polyolefin, polyvinyl chloride, polyamide, polyamide elastomer, polyester, polyester elastomer, polyurethane, polyurethane elastomer, fluoroplastics, polycarbonate, polystyrene, polyacetal, polyimide, and polyether imide.

The sheath hub 630 has the side port 14 which communicates with the sheath tube 620. To the side port 14 is fluid-tightly connected one end of the flexible tube 15 made of polyvinyl chloride for example. To the other end of the tube 15 is attached the three-way stopcock 16. For the purpose of priming, a liquid such as physiological saline is introduced into the introducer sheath 611 through one port of the three-way stopcock 16 and the tube 15.

Figure 32:
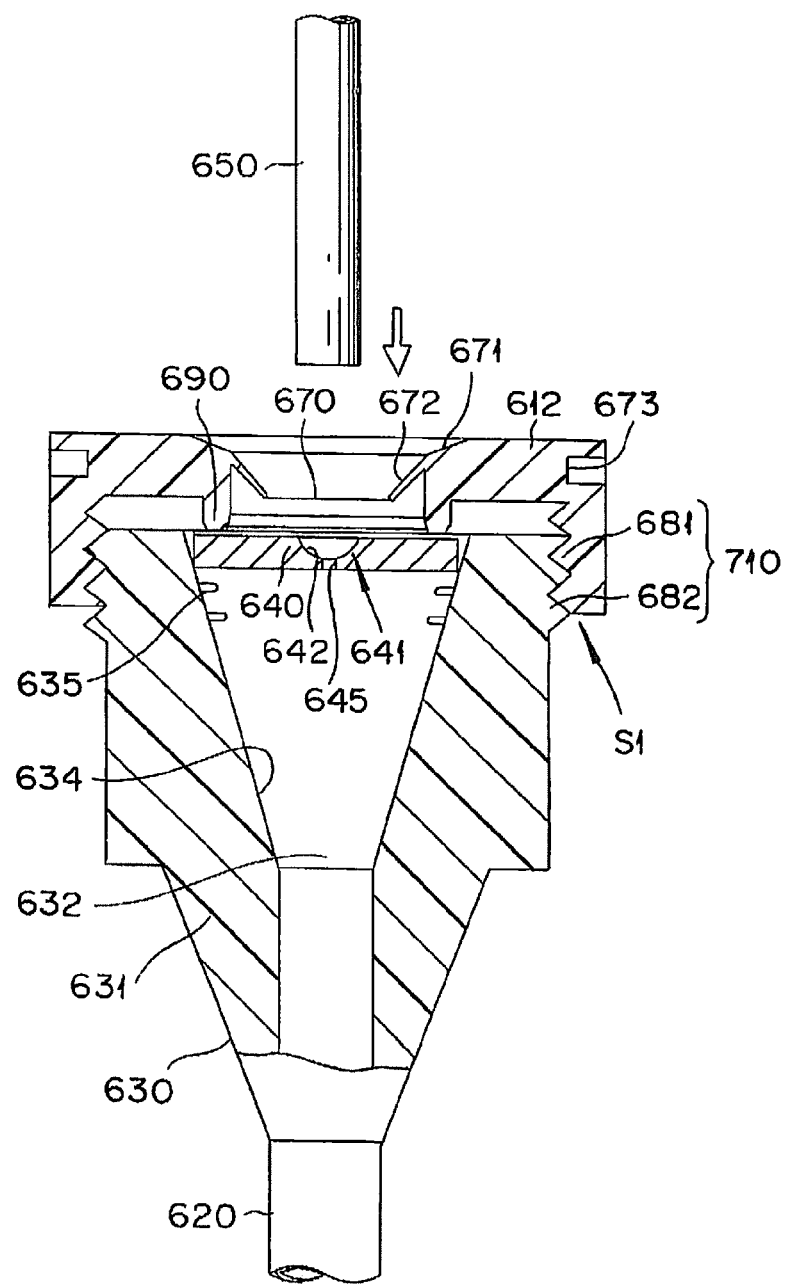
FIG. 32 is a schematic sectional view of a cap-sheath hub assembly illustrating how the introducer assembly works, with the dilator hub not yet temporarily fixed to the cap.

As shown in FIG. 32, the sheath hub 630 is made up of a sheath hub 631, a center hole 632 formed in the sheath hub 631, the tapering part 634 to hold the hemostatic valve 640, a regulating member 635 which is formed on the tapering part 634 and which regulates the movement of the hemostatic valve 640 toward the distal end of the tapering part 634, and a second screw part 682 which is formed on the outer peripheral edge part at the proximal end of the sheath hub 631.

Figure 31:
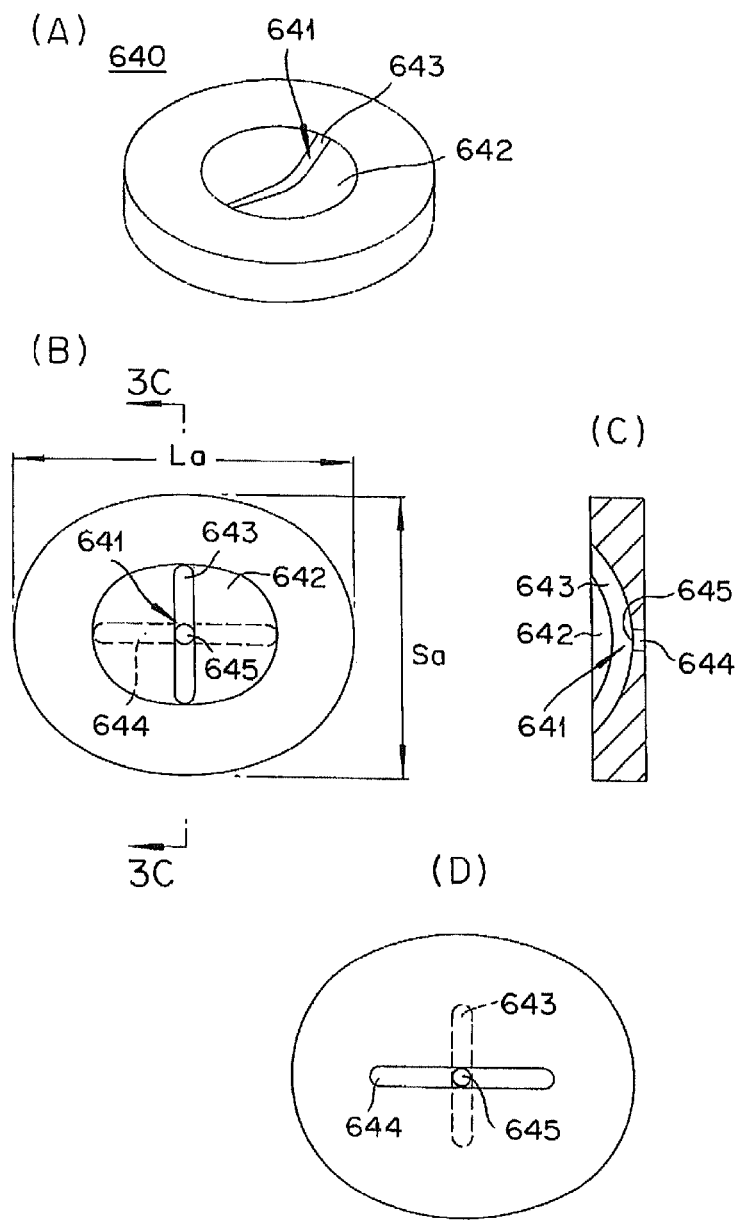
FIG. 31(A) is a perspective view showing the hemostatic valve.
FIG. 31(B) is a front view showing the hemostatic valve.
FIG. 31(C) is a sectional view taken along the line 31C-31C in FIG. 31(B)
FIG. 31(D) is a rear view showing the hemostatic valve.

The tapering part 634 is constructed such that its inside diameter gradually decreases from its proximal end to its distal end and the inside diameter at its distal end is equal to that of the center hole 632. The tapering part 634 has an approximately circular cross section in the direction intersecting with the axial direction of the sheath hub 630. And, it holds the hemostatic valve 640 which has an ellipsoidal shape, fitted thereto (see FIG. 31(B)). The hemostatic valve 640, to which a compressive force is not applied, is held at the proximal end of the tapering part 634.

The regulating member 635 is formed integrally with the sheath hub 630, and is composed of annular projections that partly reduce the inside diameter of the tapering part 634. In this embodiment, there exist two regulating members 635 in the tapering part 634.

The sheath hub 630 should preferably be made of hard resin or the like, although is not specifically restricted. Typical examples of hard resin which can be sued in this regard include polyolefin such as polyethylene and polypropylene, polyamide, polycarbonate, and polystyrene.

As shown in FIGS. 31(A) to 31(D), the hemostatic valve 640 is composed of an elastic member of approximately ellipsoidal (discoid shape or disc-shaped) film. The hemostatic valve 640 has two sides, one referred to as the "surface" which faces the cap 612 and the other referred to as the "back side surface." The surface of the hemostatic valve 640 is oriented in the upward direction in FIG. 31(A) and in the front direction in FIG. 31(B). The hemostatic valve 640 is identical in structure with the hemostatic valve 40 used in the first embodiment described above.

The surface of the hemostatic valve 640 has a concave part 642 at the center of the surface. At the center of the concave part 642 is formed a first slit 643 which opens only to the surface (i.e., the first slit 643 does not open to the back side surface). The concave part 642 functions as a guide for the tip of the dilator tube 650 or the catheter being inserted. It also serves to reduce the resistance to insertion. In the back side surface of the hemostatic valve 640 is formed a second slit 644 which opens only in the back side surface (i.e., the second slit 644 does not open to the surface). The first slit 643 and the second slit 644 cross each other so that their intersection serves as the passage 641 of the hemostatic valve 640. In other words, the passage 641 of the hemostatic valve 640 results as the slits 643 and 644 overlap each other, with the former being formed in that side of the hemostatic valve 640 which faces the cap 612 and the latter being formed in that side of the hemostatic valve 640 which is opposite to the cap 612. Each of the first and second slits 643 and 644 takes on the groove-like shape with a prescribed width (for example, about 0.5 mm). Consequently, the passage 641 of the hemostatic valve 640 has a small opening 645 before the dilator tube 650 is inserted into the passage 641 and the hemostatic valve 640 is pressed by the deforming member 690 or while the hemostatic valve 650 is in an unloaded state shown in FIG. 32.

The hemostatic valve 640 may have any dimensions suitable for it to be fitted into the tapering part 634 of the sheath hub 630. The hemostatic valve 640 may be formed from any elastic material and is not limited to a specific material. Examples of materials which can be used to fabricate the hemostatic valve 640 include silicone rubber, latex rubber, butyl rubber, and isoprene rubber.

As shown in FIG. 33, the passage 641 of the hemostatic valve 640 is expanded and deformed by the dilator tube 650 as the dilator tube 650 is inserted into the passage. According to this embodiment, the passage 641 has the small opening 645, so that it deforms less than a passage having no opening when the dilator tube 650 is inserted. Moreover, the concave part 642 also helps reduce deformation when the dilator tube 650 is inserted. Therefore, the passage 641 is restored to its initial shape shown in FIG. 32 owing to its elastic recovery force after the dilator tube 650 is pulled out, with the compressive force removed in such a direction as to close the passage 641.

Figure 35:
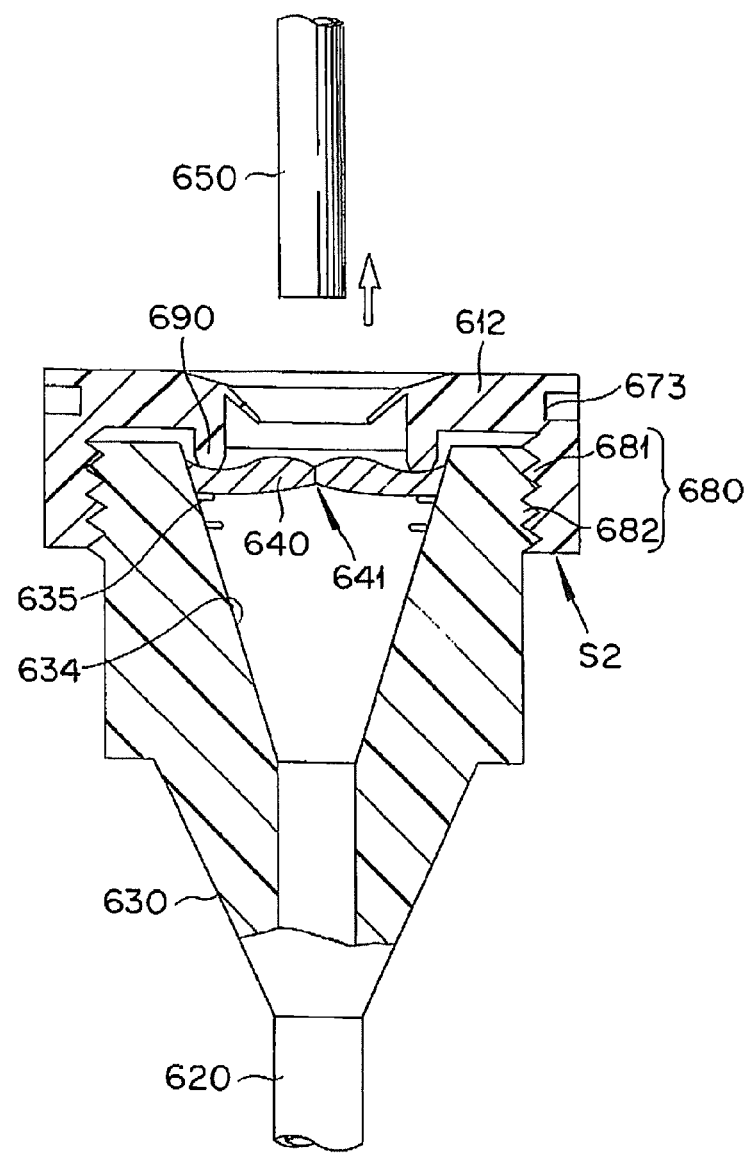
FIG. 35 is a schematic sectional view showing the cap-sheath hub assembly which has changed from that shown in FIG. 34, with the dilator pulled out.

As shown in FIG. 35, upon pressing onto its back side surface by the deforming member 690, the hemostatic valve 640 moves along the inner wall of the tapering part 634 and bends at the first slit 643. As a result, the hemostatic valve 640 changes at least in its surface in such a way that the small opening 645 closes and the passage 641 becomes closed. For deformation as described above, the hemostatic valve 640 (which is approximately ellipsoidal with a short axis Sa and a long axis La) has the first slit 643 formed along the short axis Sa (see FIG. 31(B)). After deformation, the hemostatic valve 640 becomes approximately circular in its plan view, so that there exists a circumferentially uniform clearance between the outer peripheral edge part of the hemostatic valve 640 and the inner wall of the tapering part 634 of the sheath hub 630, thereby helping to ensure excellent sealability.

The dilator 613 serves to prevent the sheath tube 620 from sharply bending when the introducer sheath 611 is inserted into the blood vessel or to expand the perforation in the skin.

Figure 29:
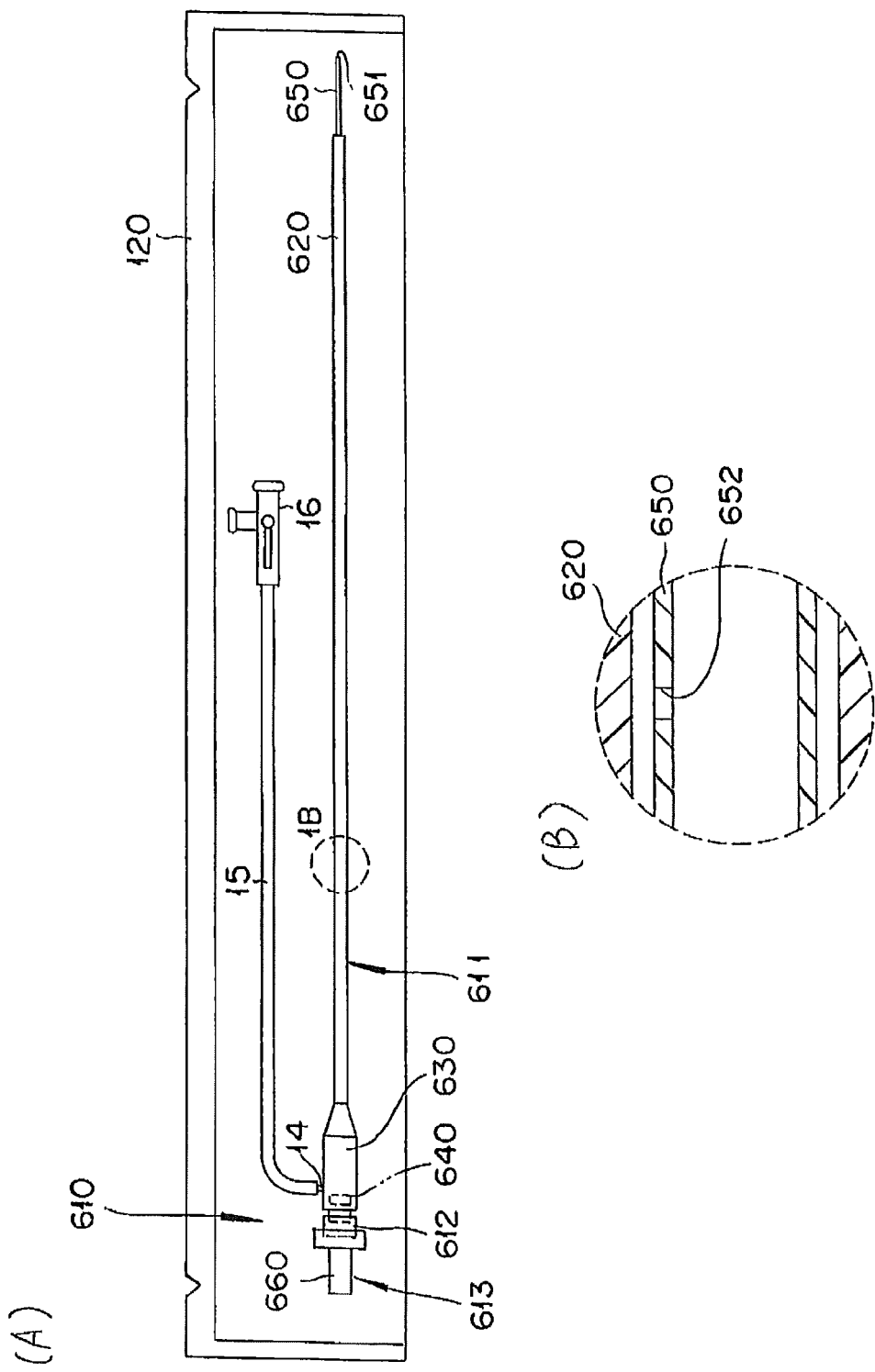
FIG. 29(A) is a plan view showing the introducer assembly pertaining to the third embodiment which is packaged in a packaging film.
FIG. 29(B) is an enlarged sectional view of that part of FIG. 29(A) which is encircled by the broken line 29B.
Figure 30:
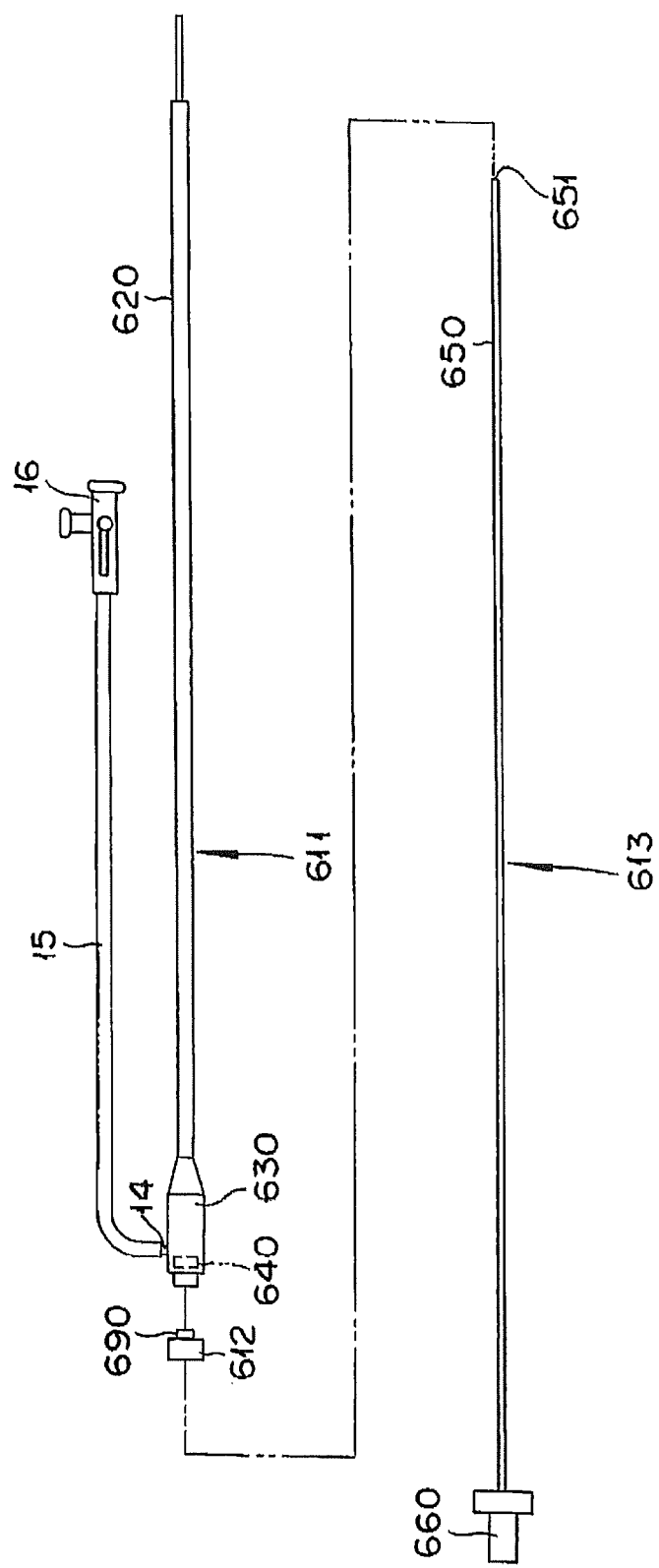
FIG. 30 is a plan view showing the introducer assembly which has been taken apart to the introducer sheath, the cap, and the dilator.

The dilator tube 650 passes through the sheath tube 620 such that a distal end 651 of the dilator tube 650 exposes itself distally beyond the distal end of the sheath tube 620, as shown in FIG. 29. The dilator tube 650 may be held in the sheath tube 620 without the distal end 651 of the dilator tube 650 exposing distally beyond the distal end of the sheath tube 620 until the cap 612 is pushed in.

The dilator tube 650 has an opening 652, shown in FIG. 29(B), which permits a fluid to be supplied to the introducer sheath 611 to flow into the dilator tube 650 when the introducer sheath 611 and the dilator 613 are integrated with each other. When the introducer sheath 611 and the dilator 613 are integrated with each other, there exists a small clearance between the sheath hub 630 and the dilator tube 650 and between the sheath tube 620 and the dilator tube 650. Therefore, physiological saline to be supplied to the introducer sheath 611 for priming or BOG to be supplied to the introducer sheath 611 for sterilization will pass the sheath hub 630 through the opening 652 formed in the dilator tube 650 and flow into the dilator tube 650. This is the reason why priming and sterilization for the dilator tube 650 can be accomplished rather smoothly even though the introducer sheath 611 and the dilator 613 are previously integrated with each other.

No specific restrictions are imposed on the number of openings 652 for fluid to flow into the dilator tube 650. There should preferably exist at least two openings or more for prompting a relatively smooth distribution of fluid. The dimensions and shape of the opening are not specifically restricted.

The dilator tube 650 may be formed from a polymeric material or a mixture of polymeric materials. Examples of typical materials include polyolefin such as polyethylene, polypropylene, polybutene, ethylene-propylene copolymer, ethylene-vinyl acetate copolymer, ionomer, and mixture thereof, polyolefin elastomer, crosslinked polyolefin, polyvinyl chloride, polyamide, polyamide elastomer, polyester, polyester elastomer, polyurethane, polyurethane elastomer, fluoroplastics, polycarbonate, polystyrene, polyacetal, polyimide, and polyether imide.

As shown in FIG. 33, the dilator hub 660 is composed of a dilator hub 661, a center hole 662 formed in the dilator hub 661, and a flange 663 formed at the distal end of the dilator hub 661. The flange 663 is larger in diameter than the cap 612. In addition, the flange 663 has a plurality of arms 664 axially extending toward the distal end. This disclosed embodiment includes four arms circumferentially spaced around the periphery. The individual arms 664 are capable of elastic deformation in the radial direction. Each arm 664 has at its distal end a claw 665 projecting in the radially inward direction.

The dilator hub 660 may be formed from any hard plastic material without specific restrictions. Examples of suitable materials include polyolefin such as polyethylene and polypropylene, polyamide, polycarbonate, and polystyrene.

As shown in FIGS. 32 and 33, the cap 612 takes on or possesses an approximately discoid shape. The cap 612 is so attached as to cover the proximal end of the sheath hub 630. The cap 612 has two sides, one referred to as the "surface" (which faces the dilator hub 660) and the other referred to as the "back side surface" (which is opposite to the surface).

The cap 612 is composed of an inclined surface 671 formed on the surface of the cap, a guiding part 672 which taperingly extends toward the distal end from the inclined surface 671, the through-hole 670 formed at the distal end of the guiding part 672, an annular groove 673 formed in the outer circumferential surface, and the deforming member 690 which presses the outer peripheral edge part of the hemostatic valve 640, thereby moving the hemostatic valve 640 toward the distal end of the tapering part 634. The cap 612 has on the inner periphery of its outer wall a first screw part 681 which meshes with the second screw part 682 formed on the sheath hub 630. The inclined surface 671 and the guiding part 672 guide the distal end of the dilator tube 650 to the through-hole 670 when the dilator tube 650 and the catheter are passed through. The annular groove 673 is able to detachably receive the claw 665 on the arm 664 of the dilator hub 660 as shown in FIG. 33.

The cap 612 may be formed from any hard plastic material and is not limited to a specific material. Examples of materials from which to fabricate the cap 612 include polyolefin such as polyethylene and polypropylene, polyamide, polycarbonate, and polystyrene.

Figure 34:
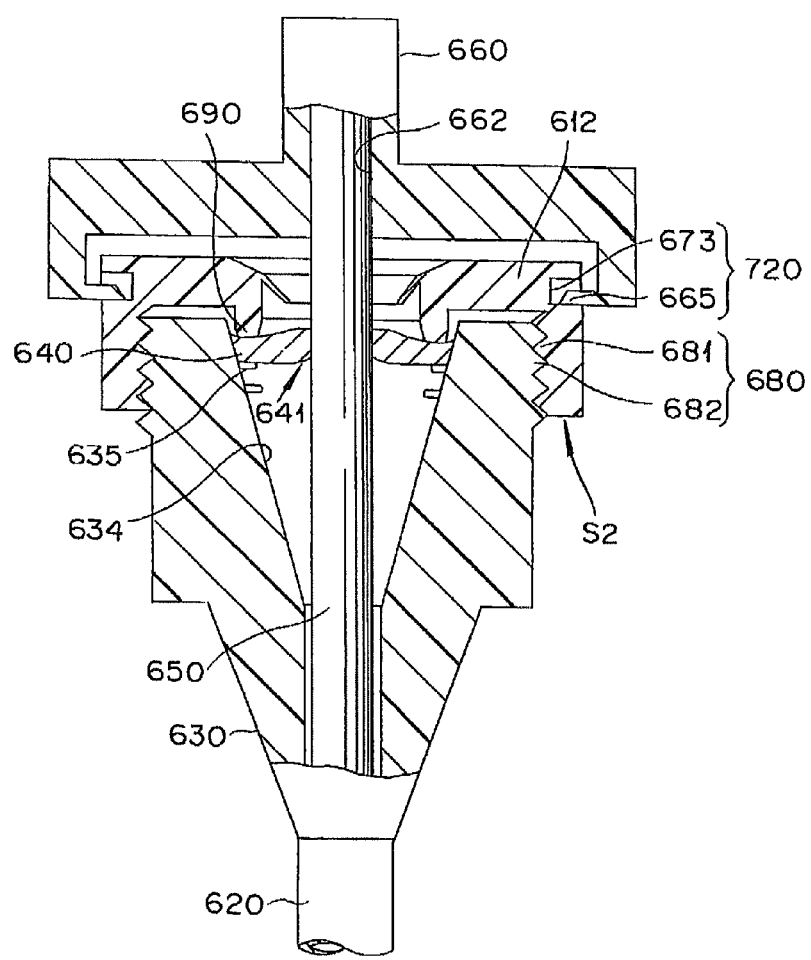
FIG. 34 is a schematic sectional view showing the introducer assembly which has changed from that shown in FIG. 33 in that the cap has moved to a second position where it engages with the sheath hub.

As shown in FIG. 34, the engaging member 680, which holds the cap 612 at the second position S2, is composed of the first screw part 681 formed on the cap 612 and the second screw part 682 formed on the sheath hub 630. When the first screw part 681 and the second screw part 682 firmly mesh with each other, that screwed area in which the first screw part 681 and the second screw part 682 are in contact with each other constitutes the engaging member 680. The cap 612 engages the sheath hub 630 so that it is held at the second position S2 as it is screwed into the sheath hub 630.

As shown in FIG. 32, the introducer assembly 610 should preferably have the holding member 710 which holds the cap 612 at the first position S1 as the cap 612 is temporarily fixed to the sheath hub 630 or the dilator hub 660. This helps prevents the cap 612 from moving to the second position S2 until the introducer assembly 610 is put to use so that the hemostatic valve 640 retains its hemostatic performance for a long period of time without the hemostatic valve 640 being deformed by compression. The holding member 710 is intended to temporarily fix the cap 612 to the sheath hub 630, and it is composed of the first screw part 681 formed on the cap 612 and the second screw part 682 formed on the sheath hub 630. When the first screw part 681 and the second screw part 682 loosely mesh with each other, the lower portion of the first screw part 681 and the upper portion of the second screw part 682 constitute the holding member 710.

The deforming member 690 is a pressing ring projecting from that end surface of the cap 612 which faces the hemostatic valve 640. The pressing ring as the deforming member 690 is arranged between the hemostatic valve 640 and the cap 612. As the cap 612 moves to the second position S2, the pressing ring presses the surface of the hemostatic valve 640, so that the hemostatic valve 640 moves while pushing the inner wall of the tapering part 634 of the sheath hub 630. This movement applies a compressive force to the hemostatic valve 640 in such a direction as to close the passage 641.

As shown in FIG. 33, the introducer assembly 610 has a connecting member 720 which detachably connects the dilator hub 660 to the cap 612. The connecting member 720 is composed of the annular groove 673 formed in the cap 612 and the claw 665 formed on the dilator hub 660. The annular groove 673 and the claw 665 are formed in such a way that the dilator hub 660 is screwed into the sheath hub 630 when the dilator hub 660 is turned together with the cap 612 in the direction of arrow A in FIG. 33 and the dilator hub 660 is unscrewed from the cap 612 when the dilator hub 660 is turned in the opposite direction of arrow B shown in FIG. 33. The annular groove 673 may be so formed as to have a stopper surface which comes into contact with the claw 665 when the dilator hub 660 is turned in the direction of arrow A and a guide surface which escapes from the annular groove 673 when the dilator hub 660 is turned in the direction of arrow B. The connecting member 720 may also be designed such that the dilator hub 660 is disengaged from the cap 612 when pulled in its axial direction by using the elasticity of the arm 664.

The connecting member 720 (composed of the annular groove 673 and the claw 665) connects the dilator hub 660 to the cap 612 with a force which is smaller than that necessary for the engaging member 680 (composed of the first screw part 681 and the second screw part 682) to hold the cap 612 at the second position S2. This facilitates the relatively easy removal of the dilator 613 after the movement of the cap 612 to the second position S2.

The following is a description of how the introducer assembly 610 operates or is used.

As shown in FIG. 32, the cap 612 is temporarily fixed to the sheath hub 630 and then a compressive force is applied to the hemostatic valve 640 in such a direction as to close the passage 641.

The dilator 613 is moved close to the cap 612 and the sheath hub 630 which have been temporarily fixed together, so that the dilator tube 650 is passed through the through-hole 670 of the cap 612 and the passage 641 of the hemostatic valve 640.

As shown in FIG. 33, the dilator tube 650 is inserted into the introducer sheath 611, with the cap 612 held at the first position S1. The cap 612 remains temporarily fixed to the sheath hub 630 by the holding member 710 (composed of the first screw part 681 and the second screw part 682). The dilator hub 660 remains temporarily fixed to the cap 612 by the connecting member 720 (composed of the annular groove 673 and the claw 665). The pressing ring as the deforming member 690 does not yet press the hemostatic valve 640 toward the distal end of the tapering part 634, with the hemostatic valve 640 not receiving a compressive force in such a direction as to close the passage 641.

As shown in FIG. 34, which changes from FIG. 33, the dilator hub 660 is turned to turn the cap 612 at the same time, so that the cap 612 is screwed into the sheath hub 630 or the cap 612 is moved from the first position S1 to the second position S2. With the cap 612 moved, the deforming member 690 presses the outer peripheral edge part of the hemostatic valve 640, thereby moving the hemostatic valve 640 toward the distal end of the tapering part 634 of the sheath hub 630. The hemostatic valve 640 moves while pushing itself toward the inner wall of the tapering part 634. The hemostatic valve 640 receives a pressing force applied by the deforming member 690 as well as a pressing force produced by the hemostatic valve 640 pushing itself toward the inner wall of the tapered part 634. These pressing forces are compressive forces directed to close the passage 641. The cap 612 engages with the sheath hub 630, so that it remains at the second position S2.

The regulating member 635, which is formed on the tapering part 634 of the sheath hub 630, supports the outer peripheral edge part of back side surface of the hemostatic valve 640 while the hemostatic valve 640 moves along the inner wall of the tapering part 634. The movement of the hemostatic valve 640 is regulated because the hemostatic valve 640 has the outer peripheral edge part of both of the surface and the back side surface held between the deforming member 690 and the regulating member 635. This mechanism inhibits or prevents the hemostatic valve 640 from being displaced by the compressive force applied to the valve.

As shown in FIG. 35, which changes from FIG. 34, the dilator 613 is pulled upward. Since the connecting member 720 (composed of the annular groove 673 and the claw 665) temporarily fixes the dilator hub 660 to the cap 612 with a force which is smaller than that necessary for the engaging member 680 (composed of the first screw part 681 and the second screw part 682) to hold the cap 612 at the second position S2, the dilator 613 alone can be rather easily pulled out after the cap 612 has been pushed to the second position S2.

The deforming member 690 continues to keep the hemostatic valve 640 pressed by virtue of the engaging member 680, so that the hemostatic valve 640 continues to receive a compressive force in such a direction as to close the passage 641. The passage 641 of the hemostatic valve 640 remains closed by pressing the surface of the hemostatic valve 640 by the deforming member 690 and also by the compressive deformation which results from the hemostatic valve 640 pushing the inner wall of the tapering part 634. In this way, the hemostatic valve 640 properly prevents the fluid such as blood from leaking from the proximal end of the dilator hub 660.

The following is a brief description of the procedure for inserting a catheter by using the introducer sheath.

The first step is to make a hole at a desired position in the skin by using an introducer needle, and the guide wire is inserted into the blood vessel for example, through the hole. The guide wire is passed through the lumen of the introducer sheath 611 from the distal end of the introducer sheath 611. Then, the introducer sheath 611 is inserted into the blood vessel along the guide wire. At the time of insertion, the distal end 651 of the dilator tube 650 expands the hole in the skin. Thus, the distal end of the introducer sheath 611 can be inserted into the blood vessel. After the introducer sheath 611 has been inserted into the blood vessel, the guide wire and the dilator 613 are pulled out, with the introducer sheath 611 left alone. In this way the introducer sheath 611 functions as a passage that connects the blood vessel to the outside of the body. So, the introducer sheath 611 permits the catheter or any other instrument to be inserted into the blood vessel through the sheath.

The amount of compressive force to be applied to the hemostatic valve 640 varies depending on how far the cap 612 is screwed into the sheath hub 630, or it can be adjusted by varying the amount of axial movement of the cap 612. In the case where insertion of the dilator tube 650 and the catheter is to be followed by insertion of another dilator tube and catheter having a larger diameter, the object is achieved by reducing the amount of screwing, thereby reducing the amount of compressive force to be applied to the hemostatic valve 640. This procedure reduces the force to close the passage 641, thereby allowing the insertion of the dilator tube and catheter having a large diameter. Since each of the regulating members 635 functions as an indicator for the amount of movement of the hemostatic valve 640, it is possible to adjust in multiple steps the amount of screwing of the cap 612 and the amount of compressive force to be applied to the hemostatic valve 640. This facilitates relatively easy adjustment of compressive force depending on the diameter of the catheter to be inserted.

As mentioned above, this embodiment produces the following effects. As the cap 612 is moved to the second position S2, the deforming member 690 moves the hemostatic valve 640 toward the distal end of the tapering part 634, thereby applying a compressive force to the hemostatic valve 640 in such a direction as to close the passage 641. Therefore, the hemostatic valve 640 may be left open and the dilator tube 650 is left passing through the hemostatic valve 640 until the introducer assembly 610 is put to use, with the hemostatic valve 640 receiving only a small burden. And, during use, the hemostatic valve 640 fully exhibits its hemostatic function even after the dilator tube 650 has been pulled out. Moreover, the dilator tube 650 exhibits its inherent function as the core of the sheath tube 620 because the dilator tube 650 does not need to be reduced in diameter over a portion of its length. Therefore, the introducer assembly 610, in which the introducer sheath 611 and dilator 613 are previously integrated with each other, permits the hemostatic valve 640 to exhibit its hemostatic function for an extended period of time. Moreover, the introducer assembly 610 does not adversely affect the inherent function of the dilator tube 650.

The introducer assembly 610 having the introducer sheath 611 and the dilator 613 previously integrated with each other eliminates the necessity of assembling the parts at the working site for treatment and hence saves time for operation.

The fact that there is no need for assembling at the working site helps eliminate the possibility of the dilator 613 bending at its distal end and the hemostatic valve 640 being damaged when the dilator 613 is inserted. The absence of the possibility of bending at the distal end and leaking from the hemostatic valve 640 leads to reduced invasiveness for the patient.

The introducer assembly 610, which is composed of the introducer sheath 611 and the dilator 613 which are previously integrated with each other, is packaged in the packaging film 120 shown in FIG. 29. Packaging the integrated introducer sheath 11 and dilator 13 in this way allows a smaller tray to be as compared to packaging the introducer sheath 611 and the dilator 613 in an un-integrated (i.e., separate) manner. This leads to space savings and material savings, which minimizes the energy loss that otherwise occurs in the manufacturing factory and the hospital, and further on the earth. The integrated introducer assembly 610 which is air-tightly sealed in the packaging film 120 is adequately protected from contamination during distribution before use.

The fact that the outer peripheral edge part of both the surface and the back side surface of the hemostatic valve 640 is held by the deforming member 690 and the regulating member 635 prevents the displacement of the hemostatic valve 640. This helps prevent the introducer assembly 610 from becoming poor in handleability due to displacement of the hemostatic valve 640 during the operation using the introducer assembly 610.

The introducer sheath 611 and the dilator 613, which are previously integrated with each other, permit the dilator tube 650 to undergo priming and sterilization rather smoothly because the dilator tube 650 is supplied with physiological saline or EOG which is fed into the introducer sheath 611 through the opening 652 formed in the dilator tube 650.

The embodiment described above according to this embodiment includes the deforming member 690 formed integrally with the cap 612. In this case the deforming member only needs to be constructed such that the cap moves the hemostatic valve toward the distal end of the tapering part of the sheath hub. Therefore, the foregoing structure may be modified such that the cap pushes the projection formed integrally with the hemostatic valve as it moves, and this pushing action moves the hemostatic valve.

Figure 36:
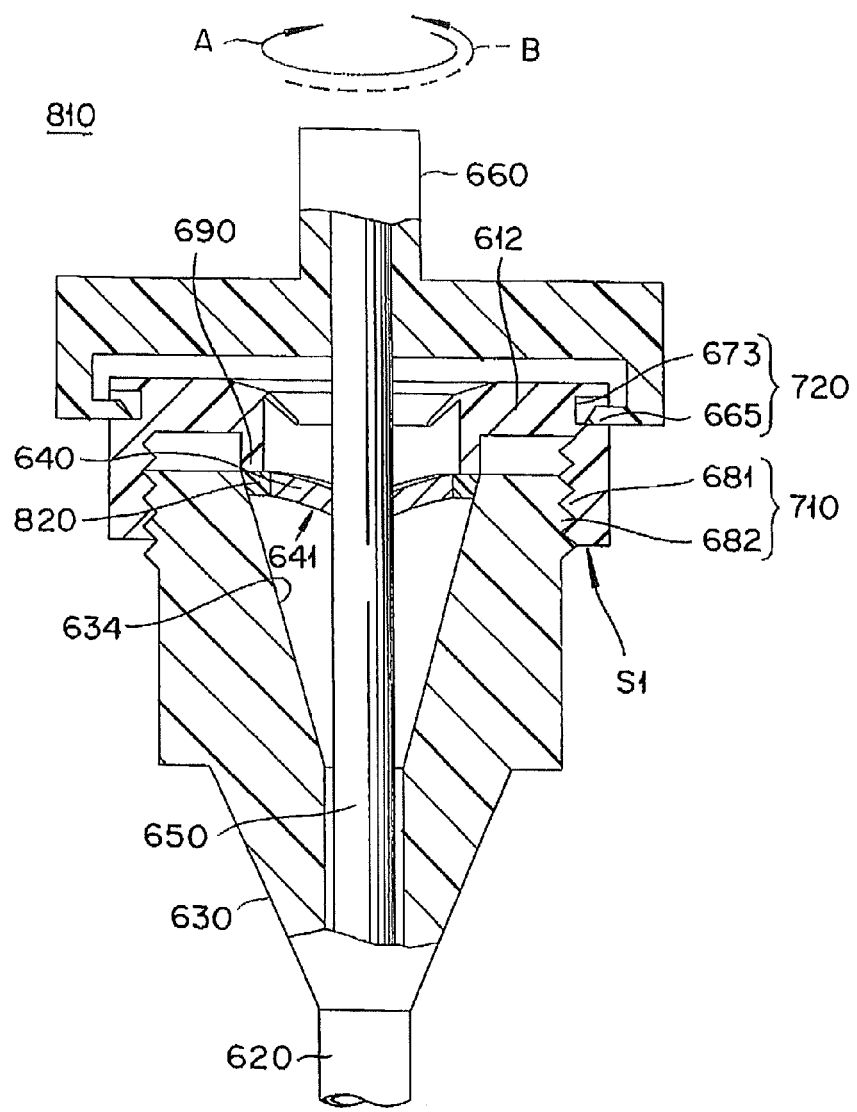
FIG. 36 is a schematic sectional view illustrating how the introducer assembly pertaining to a modification of the third embodiment works, with the cap held at the first position away from the sheath hub and the dilator hub temporarily fixed to the cap.
Figure 37:
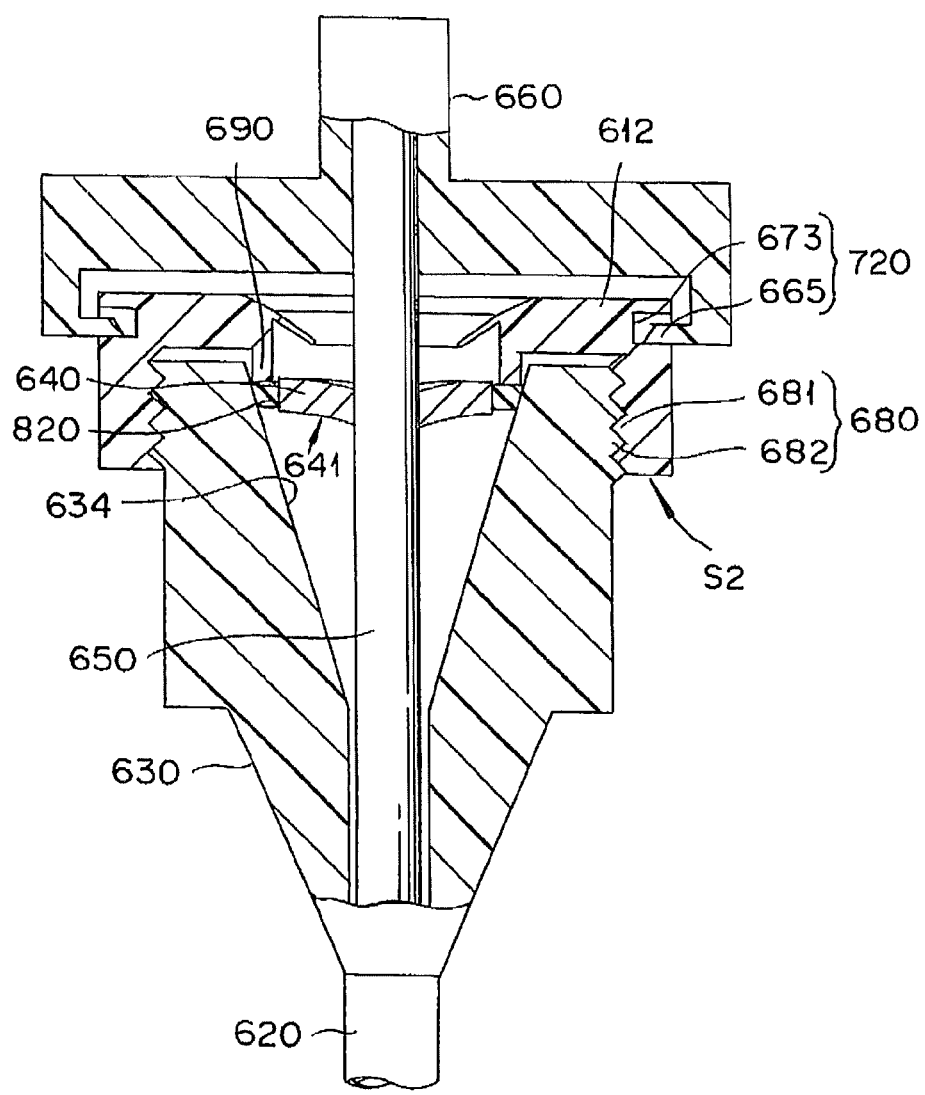
FIG. 37 is a schematic sectional view showing the introducer assembly which has changed from that shown in FIG. 36 in that the cap has moved to the second position where it engages with the sheath hub.

FIGS. 36 and 37 illustrate an introducer assembly 810 embodying a modification of the third embodiment described above. Illustrated features which are the same as features in earlier embodiments are identified by common reference numerals, and a detail discussion of such features is not repeated.

This modified embodiment includes a pressing member 820 which presses the hemostatic valve 640 in the direction intersecting the axial direction of the sheath hub 643 (radially inward direction) between the side surface of the outer periphery of the hemostatic valve 640 and the tapering part 634 of the sheath hub 630. The pressing member 820 applies a pressing force to the hemostatic valve 640 as it is moved toward the distal end of the tapering part 634 by the deforming member 690. The existence of this pressing member 820 differentiates the modified embodiment from above-described embodiment. The following is a more detailed description of this modified embodiment.

The deforming member 690 is the arm which axially projects toward the distal end of the tapering part 634 of the sheath hub 630. The arm as the deforming member 690 is formed integrally with the cap 612.

The pressing member 820 may be formed from any elastic material without specific restrictions. Typical examples of materials include silicone rubber, latex rubber, butyl rubber, and isoprene rubber. In this embodiment, the pressing member 820 is a known O-ring made of an elastic material.

The following is a description of how the introducer assembly 810 of this embodiment operates or is used.

Referring to FIG. 36, the cap 612 is temporarily fixed to the sheath hub 630 by the holding member 710, and the dilator hub 660 is temporarily fixed to the cap 612 by the connecting member 720. The elastic member 820 as the pressing member is arranged between the side surface of the outer periphery of the hemostatic valve 640 and the tapering part 634 of the sheath hub 630. The deforming member 690 does not yet move the hemostatic valve 640 and the elastic member 820 toward the distal end of the tapering part 634, so that a compressive force is not yet applied to the hemostatic valve 640 in such a direction as to close the passage 641.

Referring to FIG. 37, from the state shown in FIG. 36, the cap 612 is screwed into the sheath hub 630 by rotating the cap 12, so that the cap 612 is axially moved from the first position S1 to the second position S2. In connection with this axial movement of the cap 612, the deforming member 690 presses the elastic member 820, thereby moving the elastic member 820 and the hemostatic valve 640 toward the distal end of the tapering part 634. The elastic member 820 moves along the inner wall of the tapering part 634 and deforms by compression in the direction intersecting the axial direction of the sheath hub 630 (radially inward direction). The deformation by compression of the elastic member 820 applies a pressing force to the side surface of the outer periphery of the hemostatic valve 640. The pressing force acts on the hemostatic valve 640 as a compressive force in such a direction as to close the passage 641. This action closes the passage 641 of the hemostatic valve 640, thereby preventing leakage of body fluid such as blood from the proximal end of the dilator hub 660.

As mentioned above, the action of deforming by compression the elastic member 820 which is arranged between the side surface of the outer periphery of the hemostatic valve 640 and the tapering part 634 of the sheath hub 630 presses the hemostatic valve 640 in the direction intersecting the axial direction of the sheath hub 630. As a result, a compressive force can be acted on the hemostatic valve 640 to close the passage 641 from the side of the outer periphery of the hemostatic valve 640. This results in an effective application of a compressive force toward the axial direction of the hemostatic valve 640, which ensures the closing of the passage 641 and allows the hemostatic valve 640 to fully exhibit its hemostatic function.

In the modified example, the deforming member 690 and the pressing member 820 are formed separately. This structure may be modified as explained in the following section by forming the deforming member and the pressing member integrally. Also, the outer shape of the elastic member constituting the pressing member is not specifically restricted so long as the elastic member is capable of applying a pressing force to the side surface of the outer periphery of the hemostatic valve. Any other shape than that shown in the figures may be acceptable.

Figure 39:
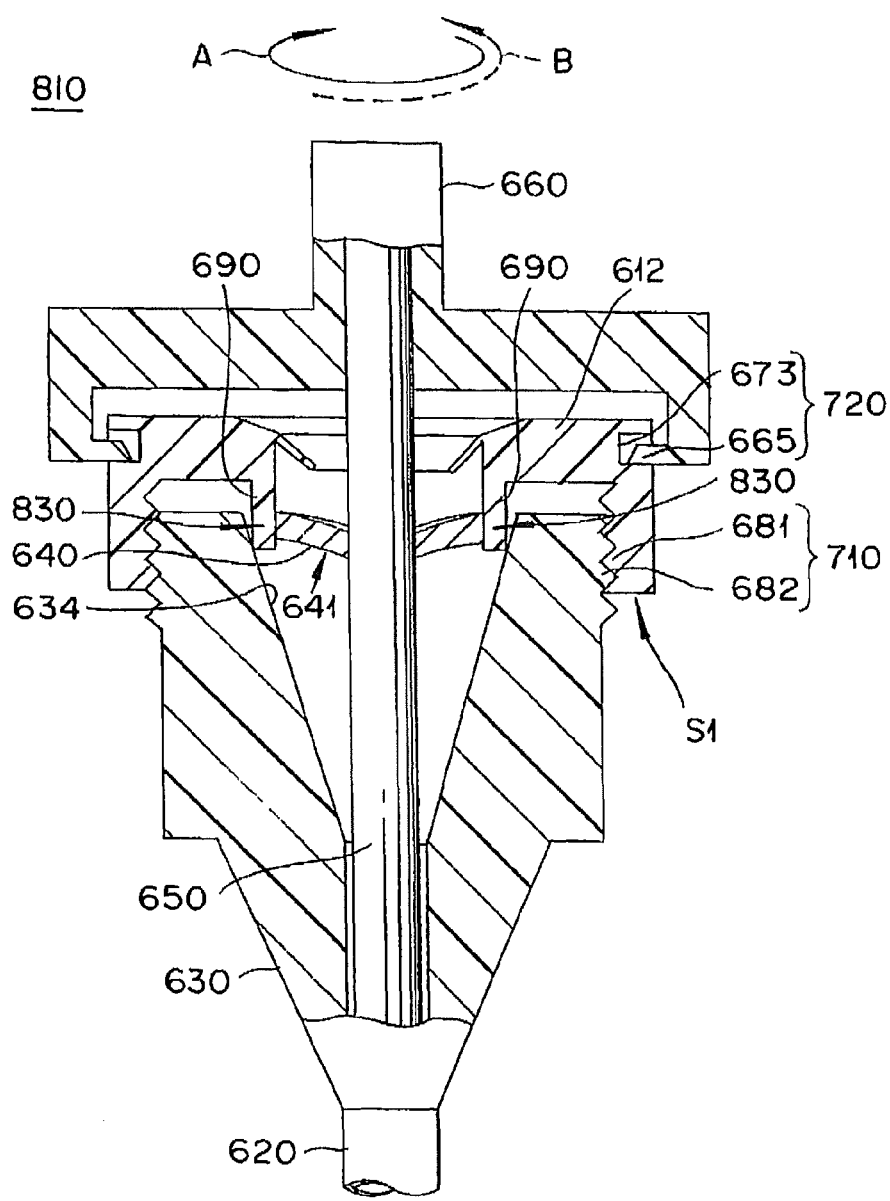
FIG. 39 is a schematic sectional view of the introducer assembly illustrating how the pressing member pertaining to the modified example works, with the cap held at the first position away from the sheath hub and the dilator hub temporarily fixed to the cap.
Figure 40:
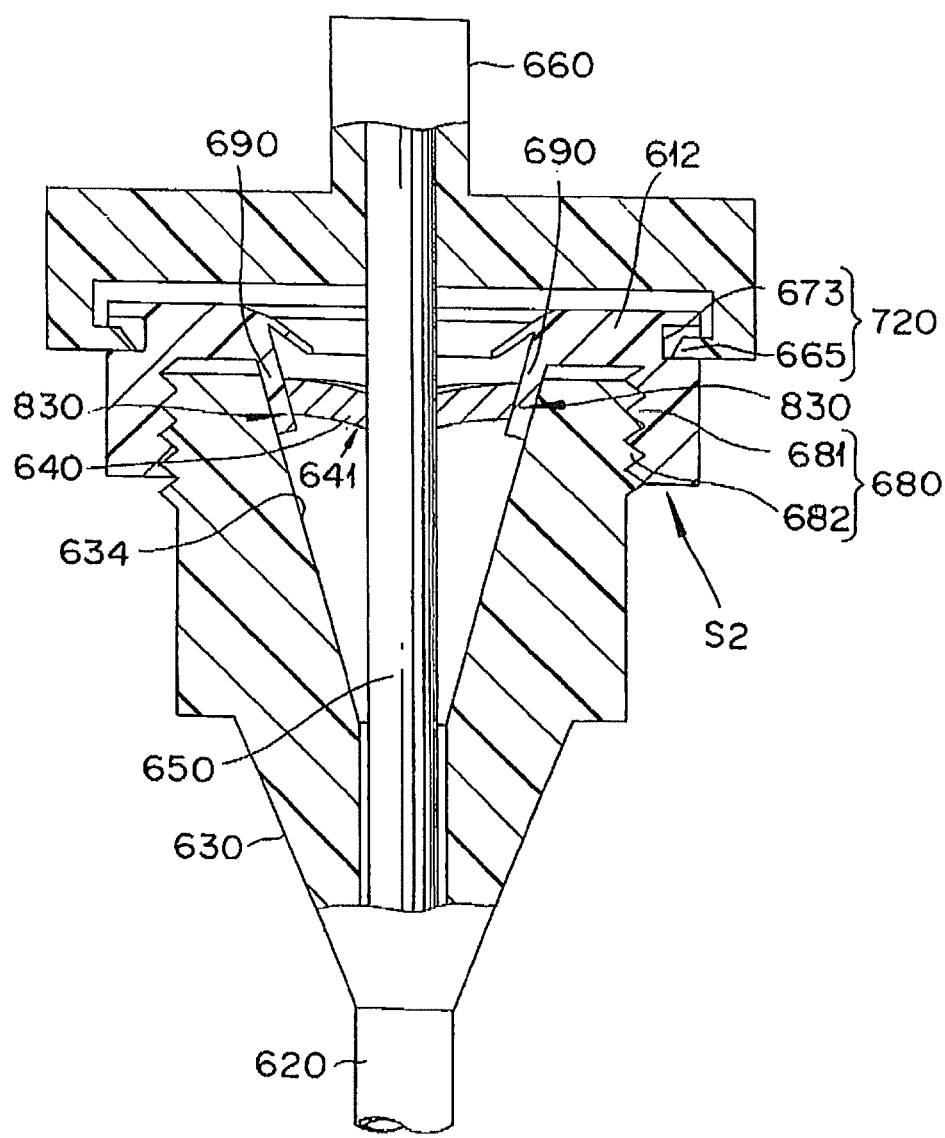
FIG. 40 is a schematic sectional view showing the introducer assembly which has changed from that shown in FIG. 39 in that the cap has moved to the second position where it engages with the sheath hub.

In the modified example, the pressing member is replaced by the elastic member arranged between the side surface of the outer periphery of the hemostatic valve 640 and the tapering part 634 of the sheath hub 630. The disclosure here is not limited to this structure. That is, the pressing member may be properly changed so long as it is arranged between the side surface of the outer periphery of the hemostatic valve 640 and the tapering part 634 of the sheath hub 630 and is capable of pressing the hemostatic valve 640 in the direction intersecting the axial direction of the sheath hub 630. For example, as shown in FIGS. 38 to 40, the pressing member 830 may be in the form of a pinching member 830 having parts arranged in pairs to hold between them the hemostatic valve 640 in the direction intersecting the axial direction of the sheath hub 630. The pinching member 830 presses the hemostatic valve 640 as it moves toward the distal end of the sheath hub 630. The following is a more detailed description of an example of this modification of the pressing member.

As shown in FIG. 38, the pinching member 830 as the pressing member is comprised of an integrally formed deforming member 690 and a cap 674. A plurality of circumferentially spaced apart slits is formed in the deforming member 690. The slits 675 permit the distal end of the deforming member 690 to undergo elastic deformation along the inner wall of the tapering part 634. According to this modified example, that part of the deforming member 690 which is capable of elastic deformation constitutes the pinching member 830. In other words, the deforming member 690, which moves the hemostatic valve 640 to the distal end of the tapering part 634 of the sheath hub 630, also functions as the pinching member 830 which pinches the hemostatic valve 640 in the direction intersecting the axial direction of the sheath hub 630. There are three pairs of pieces (six pieces) forming the pinching member 830 which hold the throughhole 670 of the cap 612, and they are arranged at equal intervals in the circumferential direction of the cap proper 674.

The following is a description of how the introducer assembly 810 according to the modification example operates or is used.

Referring to FIG. 39, the cap 612 is temporarily fixed to the sheath hub 630 by the holding member 710 and the dilator hub 660 is temporarily fixed to the cap 612 by the connecting member 720. The pinching member 830 as the pressing member is arranged between the side surface of the outer periphery of the hemostatic valve 640 and the tapering part 634 of the sheath hub 630. The hemostatic valve 640 is pinched between the paired pinching members 830 facing each other. The deforming member 690 does not yet move the hemostatic valve 640 and the pinching member 830 toward the distal end of the tapering part 634, so that a compressive force is not yet applied to the hemostatic valve 640 in such a direction as to close the passage 641.

Referring to FIG. 40, from the stage shown in FIG. 39, the cap 612 is screwed into the sheath hub 630 so that the cap 612 is moved from the first position S1 to the second position S2. The pinching member 830 moves together with the deforming member 690 and undergoes elastic deformation along the inner wall of the tapering part 634. The hemostatic valve 640, which is pinched by the pinching members 830, is moved to the distal end of the tapering part 634. As a result, the pinching members 830, which are arranged in pairs, move towards each other and come closer to each other, thereby pressing the hemostatic valve 640 in the direction intersecting the axial direction of the sheath hub 630 as indicated by the arrows in FIG. 38(B). Thus, the hemostatic valve 640 receives a compressive force in such a direction as to close the passage 641. This action closes the passage 641 of the hemostatic valve 640, thereby preventing leakage of body fluid such as blood from the proximal end of the dilator hub 660.

The modified embodiment in which the pressing member 830 is modified as mentioned above is also able to apply a compressive force to close the passage 641 mainly onto the side surface of the outer periphery of the hemostatic valve 640. This modification permits an effective application of a compressive force toward the center axial direction of the hemostatic valve 640, which helps ensure the closing of the passage 641 and allows the hemostatic valve 640 to improve its hemostatic function.

The pinching member as the pressing member is not specifically restricted in outer shape, the number of pairs, and length which may be properly changed, so long as it is capable of applying a pressing force to the hemostatic valve in the direction intersecting with the axial direction of the sheath hub.

In the third embodiment described above, the engaging member and the holding member have the structure of screw type which is composed of the first screw part and the second screw part. This structure may be changed into that of the fitting type in which the dilator is moved relative to the introducer sheath so that the two members are connected with and disconnected from each other. The connection structure of a fitting type structure may rather easily be realized by a groove-like recess and a projection that fits into the recess which are formed on the sheath hub and the dilator hub.

The regulating member formed on the tapering part of the sheath hub is not specifically restricted in number and outer shape, and it may be modified in any way so long as it is able to help prevent the hemostatic valve from displacement. However, there should preferably be plural regulating members so that the compressive force to be applied to the hemostatic valve is adjusted in multiple steps as demonstrated in this embodiment. Further, the regulating member may be provided in any embodiment which has the pressing member but does not have the regulating member. In this case, the regulating member may be utilized as a stopper to regulate the movement of the elastic member as the pressing member and the pinching member as the pressing member, thereby adjusting in multiple steps the compressive force to be applied to the hemostatic valve.

The description above describes various examples of the introducer assembly disclosed here. But these disclosed embodiments are not intended to be limitative as the embodiments may be variously changed and modified within the scope defined in the claims.

For example, the first embodiment may be modified such that the dilator tube 50 possessed by the introducer sheath 10 has an opening which functions in the same way as the opening (452, 652) for fluid passage which is formed in the dilator tube possessed by the introducer sheath as shown in the second and third embodiments. Such an opening allows priming and sterilization for the dilator tube 50 even in the case where the introducer sheath 11 and the dilator 13 are previously integrated with each other as mentioned in the second and third embodiments.

The detailed description above describes features and aspects of embodiments of an introducer assembly. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An introducer assembly comprising:
an introducer sheath comprised of a sheath tube possessing a proximal end, a sheath hub attached to the proximal end of the sheath tube and possessing a proximal end portion, and a hemostatic valve attached to the proximal end portion of the sheath hub, the hemostatic valve possessing a through passage for a catheter to pass through;

a dilator comprised of a dilator tube and a dilator hub, the dilator tube possessing a proximal end, the dilator hub being attached to the proximal end of the dilator tube;

a cap positioned between the sheath hub and the dilator hub, the cap possessing a through-hole;

the dilator tube passing through the through-hole of the cap and passing through the through passage of the hemostatic valve;

the cap being positioned in a first position in which an engaging member on the cap and the sheath hub are not engaged with one another, the cap being axially movable in a distal direction to a second position in which the engaging member on the cap and the sheath hub engage one another to hold the cap at the second position; and a deforming member positioned between the hemostatic valve and the cap to press the hemostatic valve as the cap is moved to the second position to apply a compressive force to the hemostatic valve that causes closure of the through passage in the hemostatic valve;

wherein the hemostatic valve includes one side surface facing the cap and an opposite side surface, the through passage in the hemostatic valve being comprised of first and second slits which intersect each other, the first slit opening to the one side surface of the hemostatic valve and not opening to the opposite side surface, and the second slit opening to the opposite side surface and not opening to the one side surface; and wherein, when the cap is moved to the second position, the hemostatic valve is pressed from the one side surface facing the cap by the deforming member so that the hemostatic valve bends along the first slit and the passage is closed at least in the one side surface such that the passage becomes closed.

2. The introducer assembly as defined in claim 1, further comprising a holding member which holds the cap at the first position by temporarily fixing the cap to the sheath hub or the dilator hub.

3. The introducer assembly as defined in claim 1, further comprising a connecting member which detachably connects the dilator hub to the cap, the connecting member connecting the dilator hub to the cap with a force smaller than a force of the engaging member that holds the cap at the second position.

4. The introducer assembly as defined in claim 1, wherein the cap possesses an end surface facing an end surface of the hemostatic valve, and the deforming member is either a pressing part projecting from the end surface of the cap or a bulging part projecting from the end surface of the hemostatic valve.

5. The introducer assembly as defined in claim 1, wherein the through passage is an open through hole before the dilator tube is passed through the through passage while the hemostatic valve is under no-load condition which exists before the deforming member presses the hemostatic valve.

6. The introducer assembly as defined in claim 1, wherein the hemostatic valve has an inclined part which projects toward the cap in a sloping manner.

7. The introducer assembly as defined in claim 1, wherein the dilator tube is positioned in the sheath tube with a space existing between an inner peripheral surface of the sheath tube and an outer peripheral surface of the dilator tube, the dilator tube possessing a side wall surrounding an interior of the dilator tube, and a through opening passing through the side wall of the dilator tube intermediate the proximal and distal ends of the dilator tube to communicate the interior of the dilator tube with the space to permit a fluid in the space to flow into the dilator tube, the fluid being supplied to the introducer sheath while the introducer sheath and the dilator are integrated with each other.

8. The introducer assembly as defined in claim 1, further comprising a packaging member in which is packed the introducer assembly while the dilator tube is passing through the through-hole of the cap and through the through passage of the hemostatic valve.

9. The introducer assembly as defined in claim 1, wherein the through passage of the hemostatic valve extends through the hemostatic valve in an axial direction and the deforming member is positioned between the hemostatic valve and the cap to apply a compressive force in the axial direction to the hemostatic valve.

* * * * *